US007456008B2

(12) United States Patent
Lindholm et al.

(10) Patent No.: US 7,456,008 B2
(45) Date of Patent: Nov. 25, 2008

(54) MODIFIED VIRUS COMPRISING ONE OR MORE NON-NATIVE POLYPEPTIDES

(75) Inventors: Leif Lindholm, Göteborg (SE); Anna Karin Nord, Stockholm (SE); Pierre Alain Boulanger, Lyon Cedex (FR)

(73) Assignee: Got-A-Gene AB (SE)

( * ) Notice: Subject to any disclaimer, the term of this patent is extended or adjusted under 35 U.S.C. 154(b) by 0 days.

(21) Appl. No.: 10/333,235

(22) PCT Filed: Jul. 19, 2001

(86) PCT No.: PCT/GB01/03252

§ 371 (c)(1),
(2), (4) Date: Oct. 6, 2003

(87) PCT Pub. No.: WO02/08263

PCT Pub. Date: Jan. 31, 2002

(65) Prior Publication Data

US 2004/0132007 A1  Jul. 8, 2004

(30) Foreign Application Priority Data

Jul. 19, 2000 (GB) .................................. 0017720.4

(51) Int. Cl.
*C12N 7/01* (2006.01)
*C12N 7/02* (2006.01)
*C12N 5/10* (2006.01)
*C12N 15/861* (2006.01)

(52) U.S. Cl. ..................... 435/235.1; 435/239; 435/325; 435/320.1; 424/93.2; 424/199.1; 424/233.1

(58) Field of Classification Search ................ 424/93.2; 435/235.1, 320.1, 456, 91.4, 5
See application file for complete search history.

(56) References Cited

U.S. PATENT DOCUMENTS 5,846,782 A * 12/1998 Wickham et al. .......... 435/69.7
6,057,155 A    5/2000 Wickham et al.

FOREIGN PATENT DOCUMENTS

| WO | WO 94/10323 | 5/1994 |
| WO | WO 95/19374 | 7/1995 |
| WO | WO 97/20051 | 6/1997 |
| WO | WO 99/41359 | 8/1999 |
| WO | WO 00/15823 | 3/2000 |
| WO | WO 00/12738 | 9/2000 |
| WO | WO 01/02431 | 11/2001 |

OTHER PUBLICATIONS

Harvey et al., "Variability of Human Systemic Humoral Immune Responses to Adenovirus Gene Transfer Vectors Administered to Different Organs," Journal of Virology., Aug. 1999, pp. 6729-6742.*

Hoppe et al., "A parallel three stranded alpha helical bundle at the nucleation site of collagen triple-helix formation," 1994 Federation of European Biochemical Societies, Letters 344; pp. 191-195.*

Nord et al., "A combinatorial library of an alpha-helical baterial receptor domain," Protein Eng. Jun. 1995;8(6):601-8.*

Henry et al., "Characterization of the Knob Domain of the Adenovirus Type 5 Fiber Protein Expressed in the *Escherichia coli*," Journal of Virology, vol. 68, No. 8, pp. 5239-5246 (1994).*

Xu et al., "Altered Tropism of an Ovine Adenovirus Carrying the Fiber PRotein Cell Binding Domain of Human Adenovirus Type 5," Virology, 248, pp. 156-163 (1998).*

Semple et al (Cancer Research 38:1345-1355, 1978).*

Hans-Jurgen Hoppe, et al.; A Parallel three stranded a-helical bundle at the nucleation site of collagen triple-helix formation; 1994 Federation of European Biochemical Societies; XP-001061804; pp. 191-195.

TJ Wickham "Millennium Review Targeting adenovirus"; Gene Therapy 2000; XP001055892; pp. 110-114.

Maria K. Magnusson, et al.; "Genetic Retargeting of Adenovirus: Novel Strategy Employing 'Deknobbing' of Fiber"; Journal of Virology, Aug. 2001; pp. 7280-7289; XP-001056142.

Si Michael, et al.; "Addition of a short peptide ligand to the adenovirus fiber protein"; Gene Therapy 1995; pp. 660-668.

Marie-Laure Boudin et al.; "Assembly of Adenovirus Penton Base and Fiber"; Virology 116, pp. 589-604 (1982).

Jozef Hanes, et al.; "In vitro selection and evolution of functional proteins by using ribosome display"; Proc. Natl. Acad. Sci. USA; Vol. 94; pp. 4937-4942, May 1997.

Richard W. Roberts, et al.; "RNA-peptide fusions for the in vitro selection of peptides and proteins"; Proc. Natl. Acad. Sci. USA; vol. 94, pp. 12297-12302; Nov. 1997.

Karin Nord, et al.; "A cominatorial library of an a-helical baterial receptor domain"; Protein Engineering; vol. 8, No. 6; pp. 601-608, 1995.

Thomas J. Wickham, et al.; "Targeted Adenovirus Gene Transfer to Endothelial and Smooth Muscle Cells by Using Bispecfic Antibodies"; Journal of Virology, Oct. 1996; pp. 6831-6838.

Nobuhide Doi, et al.; "Stable: protein-DNA fusion system for screening of combinatorial protein libraries in vitro"; FEBS Letters 457 (1999); pp. 227-230.

(Continued)

*Primary Examiner*—Mary E Mosher
(74) *Attorney, Agent, or Firm*—Cantor Colburn LLP

(57) ABSTRACT

A modified virus including one or more non-native polypeptides, and the use of such viruses in therapy, particularly in the treatment of tumours or other cancerous cells are disclosed. The polypeptides includes one or more framework moieties each containing one or more binding moieties, and is capable of being expressed in the cytoplasm and nucleus of a mammalian host cell in a conformation which is maintained in the absence of a ligand for the binding moieties. The conformation allows the binding moieties subsequently to bind with the ligand, and the polypeptide is capable of transport through the nuclear membrane, wherein the modified virus has an altered tropism conferred by the binding moieties.

29 Claims, 5 Drawing Sheets

OTHER PUBLICATIONS

Anke Krebber, et al.; "Reliable cloning of functional antibody variable domains from hybridomas and spleen cell repertoires employing a reengineered phage display system"; Journal of Immunological Methods 201 (1997) pp. 35-55.

R. Miller, et al.; "Editorial: Towards the use of replicative adenoviral vectors for cancer gene therapy"; Gene Therapy (1996); pp. 557-559.

C. Chartier, et al.; "Efficient Generation of Recombinant Adenovirus Vectors by Homologous Recombination in *Escherichia coli*"; Journal of Virology, Jul. 1996, pp. 4805-4810.

Karl Proba, et al.; "Antibody scFv Fragments Without Disulfide Bonds Made by Molecular Evolution"; J. Mol. Biol. (1998); pp. 245-253.

Ying Tang, et al.; "Selection of Linkers for a Catalytic Single-chain Antibody Using Phage Display Technology"; The Journal of Biological Chemistry; vol. 271, No. 26, Issue of Jun. 28, pp. 15682-15686, 1996.

Alvano, et al.; "PCR-Ligation-PCR Mutagenesis: A Protocol for Creating Gene Fusions and Mutations"; Benchmarks; vol. 18; No. 5; 1995; pp. 746-752.

"Discussion and Preliminary Reports"; pp. 782-783, date not available.

Paul A. Kitts, et al.; "A Method for Producing Recombinant Baculovirus Expression Vectors at High Frequency"; Research Report; vol. 14, No. 5 (1993); pp. 810-817.

Robert McArn Horton, et al.; "Recombination and mutagenesis of DNA sequences using PCR"; R.M. Horton and L.R. Pease; pp. 217-247, date not available.

Pierre Martineau, et al.; "In vitro Folding and Thermodynamic Stablility of an Antibody Fragment Selected in Vivo for High Expression Levels in *Escherichia coli* Cytoplasm"; 1999 Academic Press; Article No. jmbi. 1999.3105; J.Mol. Biol. 1999; pp. 292, 921-929.

Bruce C. Trapnell, et al.; "Gene Therapy using adenoviral vectors" Current Biology Ltd ISSN 0958-1669; PP. 617-625, date not available.

Anotonio Cattaneo, et al.; "The selection of intracellular antibodies"; Tibtech Mar. 1999 (vol. 17); pp. 115-121.

Silvia Biocca, et al.; "Redox State of Single Chain FV Fragments Targeted to the Endoplasmic Reticulum, Cytosol and Mitochondria"; Bio/Technology vol. 13; Oct. 1995; pp. 1110-1115.

Stephen C. Emery, et al.; "Strategies for Humanizing Antibodies"; Antibody Engineering; Chapter 6; pp. 159-183, date not availabe.

Per-Ake Nygren, et al.; "Scaffolds for engineering novel binding sites in proteins"; Current Opinion in Structural Biology 1997, pp. 463-469.

Philip A. Walker, et al.; "Efficient and Rapid Affinity Purification of Proteins Using Recombinant Fusion Proteases"; Bio/Technology, vol. 12 Jun. 1994; pp. 601-605.

Marianne Hansson, et al.; "An in vitro selected vinding protein (affibody) shows conformation-dependent recognition of the respiratory syncytial virus (RSV) G protein"; Immunotechnology 4 (1999); pp. 237-252.

Igor Dmitriev, et al.; "An Adenovirus Vector with Genetically Modified Fibers Demonstrates Expanded Tropism via Utilization of a Coxsackievirus and Adenovirus Receptor-Independent Cell Entry Mechanism"; Journal of Virology, Dec. 1998, pp. 9706-9713.

Nicola Gargano, et al.; "Rescue of a Neutralizing anti-viral antibody fragment from an intracellular polyclonal repertoire expressed in mammalian cells"; FEBS Letters 414, 1997; pp. 537-540.

Bjorn Nilsson, et al.; "A synthetic IgG-binding domain based on staphylococcal protein A"; Protein Engineering; vol. 1, No. 2, 1987; pp. 107-113.

James M. Clark; "Novel non-templated necleotide addition reactions catalyzed by procaryotic and eucaryotic DNA polymerases"; Nucleic Acids Research; vol. 16, No. 20, 1988.

Tim Clakson, et al.; "General applications of PCR to gene cloning and manipulation"; pp. 187-214, date not available.

Carolyn Cohen, et al.; "a-Helical Coiled Coils: More Facts and Better Predictions"; Science, vol. 263; Jan. 28, 1994; pp. 488-489.

George Smith, et al.; "Libraries of Peptides and Proteins Displayed on Filamentous Phage"; Method in Enzymology, vol. 217; pp. 228-259, date not available.

Jacqueline L. Harrisson, et al.; "Screening of Phage Antibody Libraries"; Methods in Enzymology; vol. 267; pp. 83-109, date not available.

Elin Gunneriusson, et al.; "Staphylococcal Surface Display of Immunoglobulin A (IgA) and IgE-Specific In Vitro-Selected Binding Proteins (Affibodies) Based on *Staphylococcus aureus* Protein A"; Applied and Environmental Microbiology, Sep. 1999, pp. 4134-4140.

E. Oosterwijk, et al.; "Monoclonal Antibody G 250 Recognizes a Determinant Present in Renal-Cell Carcinoma and Absent from Normal Kidney"; Int. J. Cancer: 38, 1986; pp. 489-494.

Jeong Shin Hong, et al.; "The Amino Terminus of the Adenovirus Fiber Protein Encodes the Nuclear Localization Signal"; Virology 185; pp. 758-767 (1991).

Tong-Chuan He, et al.; "A Simplified System for Generating Recombinant Adenoviruses"; Proc. Natl. Acad. Sci. USA; vol. 95, pp. 2509-2514, Mar. 1998.

Pehr B. Harbury, et al.; "A Swtich Between Two-, Three, and Four-Stranded Coiled Coils in GCN4 Leucine Zipper Mutants"; Science; vol. 262; Nov. 26, 1993; pp. 1401-1407.

Mo E. Weijtens, et al.; "Single Chain Ig/v Gene-Redirected Human T Lymphocytes Procedure Cytokines, Specifically Lyse Tumor Cells, and Recycle Lytic Capacity"; The Journal of Immunology; 1996; 157; pp. 836-843.

Di Xia, et al.; "Crystal structure of the receptor-binding domain of adenovirus type 5 fiber protein at 1.7 A resolution"; Current Biology Ltd ISSN 0969-2126; pp. 1259-1270, date not available.

Lena Jendeberg, et al.; "Engineering of Fc, and $FC_3$ from human immunoglobulin G to analyse subclass specificity for staphylococcal protein $A^1$"; Jounal of Immunological Methods 201 (1997) pp. 25-34.

J. Chroboczek, et al.; "Adenovirus Fiber"; pp. 163-200, date not available.

* cited by examiner

A. WT Fiber

B. A7 EGF

C. A7 scFv C242

D. A7 scFv G250

E. A7 $Z_{IgG}$

F. A7 Affi IgA

G. A7 $Z_{IgG}/Z_{IgA}$

H. A7 $Z_{IgG}/Z_{IgG}$

I. A7 $Z_{IgG}$ Xa Knob

Wild type fiber:

Recombinant knobless fibers:

New cell-binding ligands:

SEQUENCE LISTING

```
<160> NUMBER OF SEQ ID NOS: 71

<210> SEQ ID NO 1
<211> LENGTH: 1746
<212> TYPE: DNA
<213> ORGANISM: Human adenovirus type 5

<400> SEQUENCE: 1
atgaagcgcg caagaccgtc tgaagatacc ttcaacccg tgtatccata tgacacggaa      60
accggtcctc caactgtgcc ttttcttact cctcccttg tatcccccaa tgggtttcaa    120
gagagtcccc ctggggtact ctctttgcgc ctatccgaac ctctagttac ctccaatggc    180
atgcttgcgc tcaaaatggg caacggcctc tctctggacg aggccggcaa ccttacctcc    240
caaaatgtaa ccactgtgag cccacctctc aaaaaaacca agtcaaacat aaacctggaa    300
atatctgcac ccctcacagt tacctcagaa gccctaactg tggctgccgc cgcacctcta    360
atggtcgcgg caacacact caccatgcaa tcacaggccc cgctaaccgt gcacgactcc    420
aaacttagca ttgccaccca aggaccctc acagtgtcag aaggaaagct agccctgcaa    480
acatcaggcc cctcaccac caccgatagc agtaccctta ctatcactgc ctcacccct    540 ctaactactg ccactggtag cttgggcatt gacttgaaag agcccattta tacacaaaat    600
ggaaaactag gactaaagta cggggctcct ttgcatgtaa cagacgacct aaacactttg    660
accgtagcaa ctggtccagg tgtgactatt aataatactt ccttgcaaac taaagttact    720
ggagccttgg gttttgattc acaaggcaat atgcaactta atgtagcagg aggactaagg    780
attgattctc aaaacagacg ccttatactt gatgttagtt atccgtttga tgctcaaaac    840
caactaaatc taagactagg acagggccct cttttataa actcagccca caacttggat    900
attaactaca acaaaggcct ttacttgttt acagcttcaa caattccaa aaagcttgag    960 gttaacctaa gcactgccaa ggggttgatg tttgacgcta cagccatagc cattaatgca   1020
ggagatgggc ttgaatttgg ttcacctaat gcaccaaaca caaatccct caaaacaaaa   1080 attggccatg gcctagaatt tgattcaaac aaggctatgg ttcctaaact aggaactggc   1140
cttagttttg acagcacagg tgccattaca gtaggaaaca aaaataatga taagctaact   1200
ttgtggacca caccagctcc atctcctaac tgtagactaa atgcagagaa agatgctaaa   1260
ctcactttgg tcttaacaaa atgtggcagt caaatacttg ctacagtttc agttttggct   1320
gttaaaggca gtttggctcc aatatctgga acagttcaaa gtgctcatct tattataaga   1380
```

```
tttgacgaaa atggagtgct actaaacaat tccttcctgg acccagaata ttggaacttt    1440
agaaatggag atcttactga aggcacagcc tatacaaacg gtgttggatt tatgcctaac    1500
ctatcagctt atccaaaatc tcacggtaaa actgccaaaa gtaacattgt cagtcaagtt    1560
tacttaaacg gagacaaaac taaacctgta acactaacca ttacactaaa cggtacacag    1620
gaaacaggag acacaactcc aagtgcatac tctatgtcat ttcatggga ctggtctggc     1680 cacaactaca ttaatgaaat atttgccaca tcctcttaca cttttcata cattgcccaa     1740 gaataa                                                               1746
```

<210> SEQ ID NO 2
<211> LENGTH: 36
<212> TYPE: PRT
<213> ORGANISM: Homo sapiens

<400> SEQUENCE: 2

```
Pro Asp Val Ala Ser Leu Arg Gln Gln Val Glu Ala Leu Gln Gly Gln
 1               5                  10                  15
Val Gln His Leu Gln Ala Ala Phe Ser Gln Tyr Lys Lys Val Glu Leu
            20                  25                  30
Phe Pro Asn Gly
        35
```

<210> SEQ ID NO 3
<211> LENGTH: 355
<212> TYPE: DNA
<213> ORGANISM: Artificial
<220> FEATURE:
<223> OTHER INFORMATION: Recombinant Fiber A1

<400> SEQUENCE: 3

```
gaattcgatg aagcgcgcaa gaccgtctga agataccttc aaccccgtgt atccatatga     60
cacggaaacc ggtcctccaa ctgtgccttt tcttactcct cccttt gtat ccccaatgg    120 gtttcaagag agtcccctg gggtactctc tttgcgccta ccgaacctc tagttacctc     180 caatggcatg cctgacgtag caagcttacg acaacaggta gaagccttgc aagggcaggt    240
acaacactta caggcggcat ttagccaata caaaaaggta gagttgtttc caacggagc     300 caagaagctg aacgacgccc aggcccccaa gagcgaccca tcgatctaac tcgag          355
```

<210> SEQ ID NO 4
<211> LENGTH: 183
<212> TYPE: DNA
<213> ORGANISM: Homo sapiens

<400> SEQUENCE: 4

```
gggaattcat gaactccgac tccgaatgtc cattgtccca cgacggttac tgtttgcacg     60
acggtgtttg tatgtacatc gaagctttgg acaagtacgc ttgtaactgt gttgttggtt    120
acatcggtga agatgtcaa tacagagact tgaagtggtg ggaattgaga tgataagaat     180
tcc                                                                   183
```

<210> SEQ ID NO 5
<211> LENGTH: 39
<212> TYPE: DNA
<213> ORGANISM: Staphylococcus aureus

<400> SEQUENCE: 5

```
gccaagaagc tgaacgacgc ccaggcccca aagagcgac                             39
```

<210> SEQ ID NO 6

<211> LENGTH: 513
<212> TYPE: DNA
<213> ORGANISM: Artificial
<220> FEATURE:
<223> OTHER INFORMATION: Fiber construct A1 EGF

<400> SEQUENCE: 6

```
atgaagcgcg caagaccgtc tgaagatacc ttcaaccccg tgtatccata tgacacggaa    60
accggtcctc caactgtgcc ttttcttact cctccctttg tatcccccaa tgggtttcaa   120
gagagtcccc tgggtact ctctttgcgc ctatccgaac tctagttac ctccaatggc     180
atgcctgacg tagcaagctt acgacaacag gtagaagcct gcaagggca ggtacaacac   240
ttacaggcgg catttagcca atacaaaaag gtagagttgt tccaaacgg agccaagaag   300
ctgaacgacg cccaggcccc caagagcgac ccatcgatca tgaactccga ctccgaatgt   360
ccattgtccc acgacggtta ctgtttgcac gacggtgttt gtatgtacat cgaagctttg   420
gacaagtacg cttgtaactg tgttgttggt tacatcggtg aaagatgtca atacagagac   480
ttgaagtggt gggaattgag atgactcgag ggg                                513
```

<210> SEQ ID NO 7
<211> LENGTH: 811
<212> TYPE: DNA
<213> ORGANISM: Artificial
<220> FEATURE:
<223> OTHER INFORMATION: Fiber construct A7 EGF

<400> SEQUENCE: 7

```
gaattcgatg aagcgcgcaa gaccgtctga agatacctc aaccccgtgt atccatatga    60
cacggaaacc ggtcctccaa ctgtgccttt tcttactcct cctttgtat ccccaatgg    120
gtttcaagag agtcccctg gggtactctc tttgcgccta tccgaacctc tagttacctc   180
caatggcatg cttgcgctca aaatgggcaa cggcctctct ctggacgagg ccggcaacct   240
tacctcccaa aatgtaacca ctgtgagccc acctctcaaa aaaccaagt caaacataaa   300
cctggaaata tctgcacccc tcacagttac ctcagaagcc ctaactgtgg ctgccgccgc   360
acctctaatg gtcgcgggca acacactcac catgcaatca caggccccgc taaccgtgca   420
cgactccaaa cttagcattg ccacccaagg accctcaca gtgtcagaag gaaagctagc   480
ccctgacgta gcaagcttac gacaacaggt agaagcttg caagggcagg tacaacactt   540
acaggcggca tttagccaat acaaaaaggt agagttgtt ccaaacgag ccaagaagct   600
gaacgacgcc caggccccca agagcgaccc atcgatcatg aactccgact ccgaatgtcc   660
attgtcccac gacggttact gtttgcacga cggtgtttgt atgtacatcg aagctttgga   720
caagtacgct tgtaactgtg ttgttggtta catcggtgaa agatgtcaat acagagactt   780
gaagtggtgg gaattgagat gactcgaggg g                                  811
```

<210> SEQ ID NO 8
<211> LENGTH: 1056
<212> TYPE: DNA
<213> ORGANISM: Artificial
<220> FEATURE:
<223> OTHER INFORMATION: G250 single chain antibody construct

<400> SEQUENCE: 8

```
gacattgtga tgacccagtc tcaaagattc atgtccacaa cagtaggaga cagggtcagc    60
atcacctgca aggccagtca gaatgtggtt tctgctgttg cctggtatca acagaaacca   120
ggacaatctc ctaaactact gatttactca gcatccaatc ggtacactgg agtccctgat   180
```

```
cgcttcacag gcagtggatc tgggacagat ttcactctca ccattagcaa tatgcagtct    240
gaagacctgg ctgatttttt ctgtcaacaa tatagcaact atccgtggac gttcggtgga    300
ggcaccaagc tggaaatcaa aggatctggc tctacttccg gtagcggcaa atcctctgaa    360
ggcaaaggta ctagagacgt gaagctcgtg gagtctgggg gaggcttagt gaagcttgga    420
gggtccctga aactctcctg tgcagcctct ggattcactt tcagtaacta ttacatgtct    480
tgggttcgcc agactccaga aagaggctg gagttggtcg cagccattaa tagtgatggt     540
ggtatcacct actatctaga cactgtgaag ggccgattca ccatttcaag agacaatgcc    600
aagaacaccc tgtacctgca aatgagcagt ctgaagtctg aggacacagc cttgttttac    660
tgtgcaagac accgctcggg ctacttttct atggactact ggggtcaagg aacctcagtc    720
accgtctcct catgcccacc gtgcccagca cctgaactcc tagggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgag                             1056

<210> SEQ ID NO 9
<211> LENGTH: 793
<212> TYPE: DNA
<213> ORGANISM: Artificial
<220> FEATURE:
<223> OTHER INFORMATION: C242 single chain antibody Construct

<400> SEQUENCE: 9
gcggcccagc cggccacgaa ttcatcgatg atattgtga tgactcaggc tgcaccctct     60
gtacctgtca ctcctggaga gtcagtatcc atctcctgca ggtctagtaa gagtctcctg    120
catagtaatg caacactta cttgtattgg ttcctgcaga ggccaggcca gtctcctcag    180
ctcctgatat atcggatgtc caaccttgtc tcaggagtcc cagacaggtt cagtggcagt    240
gggtcaggaa ctgctttcac actgagaatc agtagagtgg aggctgagga tgtgggtgtt    300
tattactgtc tgcaacatct agagtatccg ttcacgttcg gtcctgggac caagctggag    360
ctgaaacggc cccggacttt tgttcccccg ccgctagtt tccctgatca ctcccctcgt     420
ggccaggtcc agttggtgca gtctggacct gagctgaaga gcctggaga cagtcaag      480 atctcctgca aggcttctga ttataccttc acatactatg aatgaactg ggtgaagcag    540 gctccgggaa agggttttaaa gtggatgggc tggatagaca ccaccactgg agagccaaca    600
tatgctgaag atttttaaggg acggattgcc ttctctttgg agacctctgc cagcactgcc    660
tatttgcaga tcaaaaacct caaaaatgag gacacggcta catatttctg tgcaagacgg    720
gggccttaca ctggtactt tgatgtctgg ggccaaggga ccacggtcac cgtctcctca    780
ctcgattaac tcg                                                      793

<210> SEQ ID NO 10
<211> LENGTH: 1411
<212> TYPE: DNA
<213> ORGANISM: Artificial
<220> FEATURE:
<223> OTHER INFORMATION: Fiber construct A1 G250

<400> SEQUENCE: 10
```

| | |
|---|---|
| gaattcgatg aagcgcgcaa gaccgtctga agatacccttc aaccccgtgt atccatatga | 60 |
| cacggaaacc ggtcctccaa ctgtgccttt tcttactcct ccctttgtat cccccaatgg | 120 |
| gtttcaagag agtcccctg gggtactctc tttgcgccta tccgaacctc tagttacctc | 180 |
| caatggcatg cctgacgtag caagcttacg acaacaggta gaagccttgc aagggcaggt | 240 |
| acaacactta caggcggcat ttagccaata caaaaaggta gagttgtttc caaacggagc | 300 |
| caagaagctg aacgacgccc aggcccccaa gagcgaccca tcgatcgaca ttgtgatgac | 360 |
| ccagtctcaa agattcatgt ccacaacagt aggagacagg gtcagcatca cctgcaaggc | 420 |
| cagtcagaat gtggttttctg ctgttgcctg gtatcaacag aaaccaggac aatctcctaa | 480 |
| actactgatt tactcagcat ccaatcggta cactggagtc cctgatcgct tcacaggcag | 540 |
| tggatctggg acagatttca ctctcaccat tagcaatatg cagtctgaag acctggctga | 600 |
| ttttttctgt caacaatata gcaactatcc gtggacgttc ggtggaggca ccaagctgga | 660 |
| aatcaaagga tctggctcta cttccggtag cggcaaatcc tctgaaggca aaggtactag | 720 |
| agacgtgaag ctcgtggagt ctgggggagg cttagtgaag cttggagggt ccctgaaact | 780 |
| ctcctgtgca gcctctggat tcactttcag taactattac atgtcttggg ttcgccagac | 840 |
| tccagagaag aggctggagt tggtcgcagc cattaatagt gatggtggta tcacctacta | 900 |
| tctagacact gtgaagggcc gattcaccat ttcaagagac aatgccaaga acaccctgta | 960 |
| cctgcaaatg agcagtctga gtctgaggga cacagccttg tttttactgtg caagacaccg | 1020 |
| ctcgggctac ttttctatgg actactgggg tcaaggaacc tcagtcaccg tctcctcatg | 1080 |
| cccaccgtgc ccagcacctg aactcctagg gggaccgtca gtcttcctct tccccccaaa | 1140 |
| acccaaggac accctcatga tctcccggac ccctgaggtc acatgcgtgg tggtggacgt | 1200 |
| gagccacgaa gaccctgagg tcaagttcaa ctggtacgtg gacggcgtgg aggtgcataa | 1260 |
| tgccaagaca aagccgcggg aggagcagta caacagcacg taccgggtgg tcagcgtcct | 1320 |
| caccgtcctg caccaggact ggctgaatgg caaggagtac aagtgcaagg tctccaacaa | 1380 |
| agccctccca gcccccatcg agtaactcga g | 1411 |

<210> SEQ ID NO 11
<211> LENGTH: 1702
<212> TYPE: DNA
<213> ORGANISM: Artificial
<220> FEATURE:
<223> OTHER INFORMATION: Fiber construct A7 G250

<400> SEQUENCE: 11

| | |
|---|---|
| gaattcgatg aagcgcgcaa gaccgtctga agatacccttc aaccccgtgt atccatatga | 60 |
| cacggaaacc ggtcctccaa ctgtgccttt tcttactcct ccctttgtat cccccaatgg | 120 |
| gtttcaagag agtcccctg gggtactctc tttgcgccta tccgaacctc tagttacctc | 180 |
| caatggcatg cttgcgctca aatgggcaa cggcctctct ctggacgagg ccggcaacct | 240 |
| tacctcccaa aatgtaacca ctgtgagccc acctctcaaa aaaccaagt caaacataaa | 300 |
| cctgaaaata tctgcacccc tcacagttac ctcagaagcc ctaactgtgg ctgccgccgc | 360 |
| acctctaatg gtcgcgggca acacactcac catgcaatca caggccccgc taaccgtgca | 420 |
| cgactccaaa cttagcattg ccaccccaagg acccctcaca gtgtcagaag gaaagctagc | 480 |
| ccctgacgta gcaagcttac gacaacaggt agaagccttg caagggcagg tacaacactt | 540 |
| acaggcggca tttagccaat acaaaaaggt agagttgttt ccaaacggag ccaagaagct | 600 |
| gaacgacgcc caggccccca gagcgaccc atcgatcgac attgtgatga cccagtctca | 660 |

```
aagattcatg tccacaacag taggagacag ggtcagcatc acctgcaagg ccagtcagaa    720
tgtggtttct gctgttgcct ggtatcaaca gaaaccagga caatctccta aactactgat    780
ttactcagca tccaatcggt acactggagt ccctgatcgc ttcacaggca gtggatctgg    840
gacagatttc actctcacca ttagcaatat gcagtctgaa gacctggctg attttttctg    900
tcaacaatat agcaactatc cgtggacgtt cggtggaggc accaagctgg aaatcaaagg    960
atctggctct acttccggta gcggcaaatc tctgaaggc aaaggtacta gagacgtgaa    1020
gctcgtggag tctgggggag cttagtgaa gcttggaggg tccctgaaac tctcctgtgc    1080
agcctctgga ttcactttca gtaactatta catgtcttgg gttcgccaga ctccagagaa    1140
gaggctggag ttggtcgcag ccattaatag tgatggtggt atcacctact atctagacac    1200
tgtgaagggc cgattcacca tttcaagaga caatgccaag aacaccctgt acctgcaaat    1260
gagcagtctg aagtctgagg acacagcctt gttttactgt gcaagacacc gctcgggcta    1320
cttttctatg gactactggg gtcaaggaac ctcagtcacc gtctcctcat gcccaccgtg    1380
cccagcacct gaactcctag ggggaccgtc agtcttcctc ttccccccaa acccaaggac    1440
caccctcatg atctcccgga cccctgaggt cacatgcgtg gtggtggacg tgagccacga    1500
agaccctgag gtcaagttca actggtacgt ggacggcgtg gaggtgcata atgccaagac    1560
aaagccgcgg gaggagcagt acaacagcac gtaccgggtg gtcagcgtcc tcaccgtcct    1620
gcaccaggac tggctgaatg gcaaggagta caagtgcaag gtctccaaca agccctccc    1680 agcccccatc gagtaactcg ag                                            1702

<210> SEQ ID NO 12
<211> LENGTH: 1111
<212> TYPE: DNA
<213> ORGANISM: Artificial
<220> FEATURE:
<223> OTHER INFORMATION: Fiber construct A1 C242

<400> SEQUENCE: 12
gaattcgatg aagcgcgcaa gaccgtctga agataccttc aaccccgtgt atccatatga     60
cacggaaacc ggtcctccaa ctgtgccttt tcttactcct ccctttgtat cccccaatgg    120
gtttcaagag agtcccctg gggtactctc tttgcgccta tccgaacctc tagttacctc     180
caatggcatg cctgacgtag caagcttacg acaacaggta gaagccttgc aagggcaggt    240
acaacactta caggcggcat ttagccaata caaaaggta gagttgtttc caaacggagc     300
caagaagctg aacgacgccc aggcccccaa gagcgaccca tcgatcgata ttgtgatgac    360
tcaggctgca ccctctgtac ctgtcactcc tggagagtca gtatccatct cctgcaggtc    420
tagtaagagt ctcctgcata gtaatggcaa cacttacttg tattggttcc tgcagaggcc    480
aggccagtct cctcagctcc tgatatatcg gatgtccaac cttgtctcag gagtcccaga    540
caggttcagt ggcagtgggt caggaactgc tttcacactg agaatcagta gagtggaggc    600
tgaggatgtg ggtgtttatt actgtctgca acatctagag tatccgttca cgttcggtcc    660
tgggaccaag ctggagctga acggcccccc ggactttgtt ccccccggccg ctagtttccc    720 tgatcactcc cctcgtggcc aggtccagtt ggtgcagtct ggacctgagc tgaagaagcc    780
tggagagaca gtcaagatct cctgcaaggc ttctgattat accttcacat actatggaat    840
gaactgggtg aagcaggctc cgggaaaggg ttttaaagtgg atgggctgga tagacaccac    900
cactggagag ccaacatatg ctgaagattt taagggacgg attgccttct ctttggagac    960
```

```
ctctgccagc actgcctatt tgcagatcaa aaacctcaaa aatgaggaca cggctacata      1020
tttctgtgca agacggggc cttacaactg gtactttgat gtctggggcc aagggaccac      1080
ggtcaccgtc tcctcactcg attaactcga g                                    1111
```

<210> SEQ ID NO 13
<211> LENGTH: 1402
<212> TYPE: DNA
<213> ORGANISM: Artificial
<220> FEATURE:
<223> OTHER INFORMATION: Fiber construct A7 C242

<400> SEQUENCE: 13

```
gaattcgatg aagcgcgcaa gaccgtctga agatacctcc aaccccgtgt atccatatga       60
cacggaaacc ggtcctccaa ctgtgccttt tcttactcct ccctttgtat cccccaatgg      120
gtttcaagag agtcccctg gggtactctc tttgcgccta tccgaacctc tagttacctc       180
caatggcatg cttgcgctca aatgggcaa cggcctctct ctggacgagg ccggcaacct      240
tacctcccaa aatgtaacca ctgtgagccc acctctcaaa aaaccaagt caaacataaa      300 cctggaaata tctgcacccc tcacagttac ctcagaagcc ctaactgtgg ctgccgccgc      360
acctctaatg gtcgcgggca acacactcac catgcaatca caggccccgc taaccgtgca      420
cgactccaaa cttagcattg ccacccaagg acccctcaca gtgtcagaag gaaagctagc      480
ccctgacgta gcaagcttac gacaacaggt agaagccttg caagggcagg tacaacactt      540
acaggcggca tttagccaat acaaaaaggt agagttgttt ccaaacgag ccaagaagct       600 gaacgacgcc caggccccca gagcgaccc atcgatcgat attgtgatga ctcaggctgc      660
accctctgta cctgtcactc ctggagagtc agtatccatc tcctgcaggt ctagtaagag      720
tctcctgcat agtaatggca acacttactt gtattggttc ctgcagaggc caggccagtc      780
tcctcagctc ctgatatatc ggatgtccaa ccttgtctca ggagtcccag acaggttcag      840
tggcagtggg tcaggaactg ctttcacact gagaatcagt agagtggagg ctgaggatgt      900
gggtgtttat tactgtctgc aacatctaga gtatccgttc acgttcggtc tgggaccaa      960 gctggagctg aaacggcccc cggactttgt tccccggcc gctagtttcc ctgatcactc      1020
ccctcgtggc caggtccagt tggtgcagtc tggacctgag ctgaagaagc ctggagagac      1080
agtcaagatc tcctgcaagg cttctgatta taccttcaca tactatggaa tgaactgggt      1140
gaagcaggct ccgggaaagg gtttaaagtg gatgggctgg atagacacca ccactggaga      1200
gccaacatat gctgaagatt ttaagggacg gattgccttc tctttggaga cctctgccag      1260
cactgcctat ttgcagatca aaaacctcaa aaatgaggac acggctacat atttctgtgc      1320
aagacggggg ccttacaact ggtactttga tgtctggggc caagggacca cggtcaccgt      1380
ctcctcactc gattaactcg ag                                              1402
```

<210> SEQ ID NO 14
<211> LENGTH: 174
<212> TYPE: DNA
<213> ORGANISM: Artificial
<220> FEATURE:
<223> OTHER INFORMATION: Affibody ZIgG

<400> SEQUENCE: 14

```
gtagacaaca aattcaacaa agaacaacaa aacgcgttct atgagatctt acatttacct       60
aacttaaacg aagaacaacg aaacgccttc atccaaagtt taaaagatga cccaagccaa      120
agcgctaact tgctagcaga agctaaaaag ctaaatgatg ctcaggcgcc gaaa            174
```

<210> SEQ ID NO 15
<211> LENGTH: 174
<212> TYPE: DNA
<213> ORGANISM: Artificial
<220> FEATURE:
<223> OTHER INFORMATION: Affibody ZIgA

<400> SEQUENCE: 15

```
gtagacaaca aattcaacaa agaaacaata caagcgagtc aagagatcag actattacct      60
aacttaaacg gtagacaaaa gcttgccttc atccacagtt tacttgatga cccaagccaa     120
agcgctaact tgctagcaga agctaaaaag ctaaatgatg ctcaggcgcc gaaa           174
```

<210> SEQ ID NO 16
<211> LENGTH: 820
<212> TYPE: DNA
<213> ORGANISM: Artificial
<220> FEATURE:
<223> OTHER INFORMATION: Recombinant Fiber A7 ZIgG

<400> SEQUENCE: 16

```
gaattcgatg aagcgcgcaa gaccgtctga agataccttc aaccccgtgt atccatatga      60
cacggaaacc ggtcctccaa ctgtgccttt tcttactcct cccttttgtat ccccaatgg     120
gtttcaagag agtccccctg gggtactctc tttgcgccta tccgaacctc tagttacctc    180
caatggcatg cttgcgctca aaatgggcaa cggcctctct ctggacgagg ccggcaacct    240
tacctcccaa aatgtaacca ctgtgagccc acctctcaaa aaaaccaagt caaacataaa    300
cctggaaata tctgcacccc tcacagttac ctcagaagcc ctaactgtgg ctgccgccgc    360
acctctaatg gtcgcgggca acacactcac catgcaatca caggcccccgc taaccgtgca   420
cgactccaaa cttagcattg ccacccaagg acccctcaca gtgtcagaag gaaagctagc   480
ccctgacgta gcaagcttac gacaacaggt agaagccttg caagggcagg tacaacactt   540
acaggcggca tttagccaat acaaaaaggt agagttgttt ccaaacggag ccaagaagct   600
gaacgacgcc caggccccca gagcgaccc atcgatcgta acaacaaat tcaacaaga     660
acaacaaaac gcgttctatg agatcttaca tttacctaac ttaaacgaag aacaacgaaa    720
cgccttcatc aaagtttaa aagatgaccc aagccaaagc gctaacttgc tagcagaagc    780
taaaaagcta aatgatgctc aggcgccgaa ataactcgag                          820
```

<210> SEQ ID NO 17
<211> LENGTH: 820
<212> TYPE: DNA
<213> ORGANISM: Artificial
<220> FEATURE:
<223> OTHER INFORMATION: Recombinant Fiber A7 ZIgA

<400> SEQUENCE: 17

```
gaattcgatg aagcgcgcaa gaccgtctga agataccttc aaccccgtgt atccatatga      60
cacggaaacc ggtcctccaa ctgtgccttt tcttactcct cccttttgtat ccccaatgg     120
gtttcaagag agtccccctg gggtactctc tttgcgccta tccgaacctc tagttacctc    180
caatggcatg cttgcgctca aaatgggcaa cggcctctct ctggacgagg ccggcaacct    240
tacctcccaa aatgtaacca ctgtgagccc acctctcaaa aaaaccaagt caaacataaa    300
cctggaaata tctgcacccc tcacagttac ctcagaagcc ctaactgtgg ctgccgccgc    360
acctctaatg gtcgcgggca acacactcac catgcaatca caggcccccgc taaccgtgca   420
```

```
cgactccaaa cttagcattg ccacccaagg acccctcaca gtgtcagaag gaaagctagc      480
ccctgacgta gcaagcttac gacaacaggt agaagccttg caagggcagg tacaacactt      540
acaggcggca tttagccaat acaaaaaggt agagttgttt ccaaacggag ccaagaagct      600
gaacgacgcc caggccccca gagcgaccc atcgatcgta gacaacaaat tcaacaaaga       660
aacaatacaa gcgagtcaag agatcagact attacctaac ttaaacggta gacaaaagct      720
tgccttcatc cacagtttac ttgatgaccc aagccaaagc gctaacttgc tagcagaagc      780
taaaaagcta aatgatgctc aggcgccgaa ataactcgag                            820
```

```
<210> SEQ ID NO 18
<211> LENGTH: 1003
<212> TYPE: DNA
<213> ORGANISM: Artificial
<220> FEATURE:
<223> OTHER INFORMATION: Recombinant Fiber A7 ZIgG/ZIgA

<400> SEQUENCE: 18
gaattcgatg aagcgcgcaa gaccgtctga agataccttc aaccccgtgt atccatatga       60
cacggaaacc ggtcctccaa ctgtgccttt tcttactcct cccttcgtat cccccaatgg      120
gtttcaagag agtcccctg gggtactctc tttgcgccta tccgaacctc tagttacctc       180
caatggcatg cttgcgctca aatgggcaa cggcctctct ctggacgagg ccggcaacct       240
tacctcccaa aatgtaacca ctgtgagccc acctctcaaa aaaccaagt caaacataaa       300 cctggaaata tctgcacccc tcacagttac ctcagaagcc ctaactgtgg ctgccgccgc      360
acctctaatg gtcgcgggca acacactcac catgcaatca caggcccgc taaccgtgca      420 cgactccaaa cttagcattg ccacccaagg acccctcaca gtgtcagaag gaaagctagc      480
ccctgacgta gcaagcttac gacaacaggt agaagccttg caagggcagg tacaacactt      540
acaggcggca tttagccaat acaaaaaggt agagttgttt ccaaacgag ccaagaagct       600 gaacgacgcc caggccccca gagcgaccc atcgatcgta gacaacaaat tcaacaaaga       660
acaacaaaac gcgttctatg agatcttaca tttacctaac ttaaacgaag aacaacgaaa      720
cgccttcatc caaagtttaa aagatgaccc aagccaaagc gctaacttgc tagcagaagc      780
taaaaagcta aatgatgctc aggcgccgaa agctcgacc gtagcaaca aattcaacaa        840 agaaacaata caagcgagtc aagagatcag actattacct aacttaaacg gtagacaaaa      900
gcttgccttc atccacagtt tacttgatga cccaagccaa agcgctaact tgctagcaga      960
agctaaaaag ctaaatgatg ctcaggcgcc gaaataactc gag                       1003
```

```
<210> SEQ ID NO 19
<211> LENGTH: 1003
<212> TYPE: DNA
<213> ORGANISM: Artificial
<220> FEATURE:
<223> OTHER INFORMATION: Recombinant Fiber A7 ZIgG/ZIgG

<400> SEQUENCE: 19
gaattcgatg aagcgcgcaa gaccgtctga agataccttc aaccccgtgt atccatatga       60
cacggaaacc ggtcctccaa ctgtgccttt tcttactcct cccttcgtat cccccaatgg      120
gtttcaagag agtcccctg gggtactctc tttgcgccta tccgaacctc tagttacctc       180
caatggcatg cttgcgctca aatgggcaa cggcctctct ctggacgagg ccggcaacct       240
tacctcccaa aatgtaacca ctgtgagccc acctctcaaa aaaccaagt caaacataaa       300 cctggaaata tctgcacccc tcacagttac ctcagaagcc ctaactgtgg ctgccgccgc      360
```

```
acctctaatg gtcgcgggca acacactcac catgcaatca caggccccgc taaccgtgca    420
cgactccaaa cttagcattg ccacccaagg acccctcaca gtgtcagaag gaaagctagc    480
ccctgacgta gcaagcttac gacaacaggt agaagccttg caagggcagg tacaacactt    540
acaggcggca tttagccaat acaaaaaggt agagttgttt ccaaacggag ccaagaagct    600
gaacgacgcc caggccccca agagcgaccc atcgatcgta gacaacaaat tcaacaaaga    660
acaacaaaac gcgttctatg agatcttaca tttacctaac ttaaacgaag aacaacgaaa    720
cgccttcatc caaagtttaa aagatgaccc aagccaaagc gctaacttgc tagcagaagc    780
taaaaagcta aatgatgctc aggcgccgaa aagctcgacc gtagacaaca aattcaacaa    840
agaacaacaa aacgcgttct atgagatctt acatttacct aacttaaacg aagaacaacg    900
aaacgccttc atccaaagtt taaagatga cccaagccaa agcgctaact tgctagcaga    960
agctaaaaag ctaatgatg ctcaggcgcc gaaataactc gag                      1003

<210> SEQ ID NO 20
<211> LENGTH: 30
<212> TYPE: DNA
<213> ORGANISM: Artificial
<220> FEATURE:
<223> OTHER INFORMATION: Primer

<400> SEQUENCE: 20
ttcctcgagt tattcttggg caatgtatga                                     30

<210> SEQ ID NO 21
<211> LENGTH: 34
<212> TYPE: DNA
<213> ORGANISM: Artificial
<220> FEATURE:
<223> OTHER INFORMATION: Primer

<400> SEQUENCE: 21
ggggaattcg atgaagcgcg caagaccgtc tgaa                                34

<210> SEQ ID NO 22
<211> LENGTH: 31
<212> TYPE: DNA
<213> ORGANISM: Artificial
<220> FEATURE:
<223> OTHER INFORMATION: Primer

<400> SEQUENCE: 22
gctcgagtta tccgtttgga aacaactcta c                                   31

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
ctcgagtcat ctcaattccc accactt                                        27

<210> SEQ ID NO 24
<211> LENGTH: 28
<212> TYPE: DNA
<213> ORGANISM: Artificial
<220> FEATURE:
<223> OTHER INFORMATION: Primer
```

<400> SEQUENCE: 24
tggcatgcct gacgtagcaa gcttacga                                          28

<210> SEQ ID NO 25
<211> LENGTH: 37
<212> TYPE: DNA
<213> ORGANISM: Artificial
<220> FEATURE:
<223> OTHER INFORMATION: Primer

<400> SEQUENCE: 25
ggggaattca tcgatgcagg tccagttggt gcagtct                                37

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
caggtccagt tggtgcagtc t                                                 21

<210> SEQ ID NO 27
<211> LENGTH: 51
<212> TYPE: DNA
<213> ORGANISM: Artificial
<220> FEATURE:
<223> OTHER INFORMATION: Primer

<400> SEQUENCE: 27
gggggcctgg gcgtcgttca gcttcttggc tccgtttgga acaactcta c                 51

<210> SEQ ID NO 28
<211> LENGTH: 60
<212> TYPE: DNA
<213> ORGANISM: Artificial
<220> FEATURE:
<223> OTHER INFORMATION: Primer

<400> SEQUENCE: 28
ctgaacgacg cccaggcccc caagagcgac ccatcgatca tgaactccga ctccgaatgt       60

<210> SEQ ID NO 29
<211> LENGTH: 36
<212> TYPE: DNA
<213> ORGANISM: Artificial
<220> FEATURE:
<223> OTHER INFORMATION: Primer

<400> SEQUENCE: 29
cccctggagt taaattttct tgtccacctt ggtgct                                 36

<210> SEQ ID NO 30
<211> LENGTH: 46
<212> TYPE: DNA
<213> ORGANISM: Artificial
<220> FEATURE:
<223> OTHER INFORMATION: Primer

<400> SEQUENCE: 30
ggggaattca tcgatggact acaaagatat tgtgatgacg caggct                     46

<210> SEQ ID NO 31
<211> LENGTH: 33

<212> TYPE: DNA
<213> ORGANISM: Artificial
<220> FEATURE:
<223> OTHER INFORMATION: Primer

<400> SEQUENCE: 31
ctacctcgag ttaacactca ttcctgttga agc                          33

<210> SEQ ID NO 32
<211> LENGTH: 31
<212> TYPE: DNA
<213> ORGANISM: Artificial
<220> FEATURE:
<223> OTHER INFORMATION: Primer

<400> SEQUENCE: 32
ggggctagcc cctgacgtag caagcttacg a                            31

<210> SEQ ID NO 33
<211> LENGTH: 33
<212> TYPE: DNA
<213> ORGANISM: Artificial
<220> FEATURE:
<223> OTHER INFORMATION: Primer

<400> SEQUENCE: 33
gggctcgagt tactcgatgg gggctgggag ggc                          33

<210> SEQ ID NO 34
<211> LENGTH: 39
<212> TYPE: DNA
<213> ORGANISM: Artificial
<220> FEATURE:
<223> OTHER INFORMATION: Primer

<400> SEQUENCE: 34
ggcccccgag gcctcgagtg aggagacggt gaccgtggt                    39

<210> SEQ ID NO 35
<211> LENGTH: 46
<212> TYPE: DNA
<213> ORGANISM: Artificial
<220> FEATURE:
<223> OTHER INFORMATION: Primer

<400> SEQUENCE: 35
ggcccagccc acgaattcat cgatggatat tgtgatgacg caggct            46

<210> SEQ ID NO 36
<211> LENGTH: 96
<212> TYPE: DNA
<213> ORGANISM: Artificial
<220> FEATURE:
<223> OTHER INFORMATION: Primer
<220> FEATURE:
<221> NAME/KEY: VARIANT
<222> LOCATION: (23)..(24)  (26)..(27)  (29)..(30)  (32)..(33)
                (35)..(36)  (38)..(39)  (41)..(42)  (44)..(45)
                (47)..(48)  (50)..(51)  (53)..(54)  (56)..(57)
                (59)..(60)  (62)..(63)  (65)..(66)  (68)..(69)
                (71)..(72)  (74).
<223> OTHER INFORMATION: N is A, G, C or T
<220> FEATURE:
<221> NAME/KEY: VARIANT
<222> LOCATION: (22)..(22)  (25)..(25)  (28)..(28)  (31)..(31)
                (34)..(34)  (37)..(37)  (40)..(40)  (43)..(43)
                (46)..(46)  (49)..(49)  (52)..(52)  (55)..(55)
                (58)..(58)  (61)..(61)  (64)..(64)  (67)..(67)
                (70)..(70)  (73).

<223> OTHER INFORMATION: S is A, G, or C

<400> SEQUENCE: 36
agactgcacc aactggacct gsnnsnnsnn snnsnnsnns nnsnnsnnsn nsnnsnnsnn    60
snnsnnsnns nnsnnccgtt tcagctccag cttggt    96

<210> SEQ ID NO 37
<211> LENGTH: 46
<212> TYPE: DNA
<213> ORGANISM: Artificial
<220> FEATURE:
<223> OTHER INFORMATION: Primer

<400> SEQUENCE: 37
ggcaattcca tcgatcgcca ccatggacat tgtgatgacc cagtct    46

<210> SEQ ID NO 38
<211> LENGTH: 33
<212> TYPE: DNA
<213> ORGANISM: Artificial
<220> FEATURE:
<223> OTHER INFORMATION: Primer

<400> SEQUENCE: 38
cccctcgagt taacactcat tcctgttgaa gct    33

<210> SEQ ID NO 39
<211> LENGTH: 42
<212> TYPE: DNA
<213> ORGANISM: Artificial
<220> FEATURE:
<223> OTHER INFORMATION: Primer

<400> SEQUENCE: 39
accacggtca ccgtctcctc agctgatgct gcaccaactg ta    42

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
tgaggagacg gtgaccgtgg t    21

<210> SEQ ID NO 41
<211> LENGTH: 33
<212> TYPE: DNA
<213> ORGANISM: Artificial
<220> FEATURE:
<223> OTHER INFORMATION: Primer

<400> SEQUENCE: 41
gggccatcga tcgtagacaa caaattcaac aaa    33

<210> SEQ ID NO 42
<211> LENGTH: 33
<212> TYPE: DNA
<213> ORGANISM: Artificial
<220> FEATURE:
<223> OTHER INFORMATION: Primer

<400> SEQUENCE: 42
gggctcgagt tatttcggcg cctgagcatc att    33

```
<210> SEQ ID NO 43
<211> LENGTH: 48
<212> TYPE: DNA
<213> ORGANISM: Artificial
<220> FEATURE:
<223> OTHER INFORMATION: Primer

<400> SEQUENCE: 43
tcggtttgga acaactcta cctttttttt cggcgcctga gcatcatt                48

<210> SEQ ID NO 44
<211> LENGTH: 48
<212> TYPE: DNA
<213> ORGANISM: Artificial
<220> FEATURE:
<223> OTHER INFORMATION: Primer

<400> SEQUENCE: 44
aaaaaggtag agttgtttcc aaacggagta gacaacaaat tcaacaaa                48

<210> SEQ ID NO 45
<211> LENGTH: 58
<212> TYPE: PRT
<213> ORGANISM: Artificial
<220> FEATURE:
<223> OTHER INFORMATION: Z-based domain
<220> FEATURE:
<221> NAME/KEY: VARIANT
<222> LOCATION: (9)..(11)  (13)..(14)  (17)..(18)  (24)..(25)
                (27)..(28)  (32)..(32)  (35)..(35)
<223> OTHER INFORMATION: Xaa is any amino acid

<400> SEQUENCE: 45

Val Asp Asn Lys Phe Asn Lys Glu Xaa Xaa Xaa Ala Xaa Xaa Glu Ile
 1               5                  10                  15

Xaa Xaa Leu Pro Asn Leu Asn Xaa Xaa Gln Xaa Xaa Ala Phe Ile Xaa
            20                  25                  30

Ser Leu Xaa Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 46
<211> LENGTH: 58
<212> TYPE: PRT
<213> ORGANISM: Artificial
<220> FEATURE:
<223> OTHER INFORMATION: Z-domain-based, X is any amino acid
<220> FEATURE:
<221> NAME/KEY: VARIANT
<222> LOCATION: (9)..(11)  (13)..(14)  (17)..(25)  (24)..(25)
                (27)..(28)  (32)..(32)  (35)..(35)  (37)..(40)
<223> OTHER INFORMATION: Xaa is any amino acid

<400> SEQUENCE: 46

Val Asp Asn Lys Phe Asn Lys Glu Xaa Xaa Xaa Ala Xaa Xaa Glu Ile
 1               5                  10                  15

Xaa Xaa Xaa Xaa Xaa Xaa Xaa Xaa Xaa Gln Xaa Xaa Ala Phe Ile Xaa
            20                  25                  30

Ser Leu Xaa Asp Xaa Xaa Xaa Xaa Ser Ala Asn Leu Leu Ala Glu Ala
        35                  40                  45

Lys Lys Leu Asn Asp Ala Gln Ala Pro Lys
    50                  55
```

```
<210> SEQ ID NO 47
<211> LENGTH: 816
<212> TYPE: DNA
<213> ORGANISM: Artificial
<220> FEATURE:
<223> OTHER INFORMATION: Anti Beta-galactosidase single chain Fv
                        fragment

<400> SEQUENCE: 47
atggccgagg tgcagctggt ggagtctggg ggaagcctgg tcaagcctgg ggggtccctg     60
agactctcct gtgcagcctc tggattcacc ttcagtaact atagcatgaa ctgggtccgc    120
caggctccag ggaaggggct ggagtggatc tcatccatta gtggtagtag tagatacata    180
tactacgcag acttcgtgaa gggccgattc accatctcca gagacaacgc cacgaactca    240
ctgtacctgc aaatgaacag cctgagagcc gaggacacgg ctgtttatta ctgtgtgaga    300
tccagtatta cgattttttgg tggcggtatg gacgtctggg gcagaggcac cctggtcacc    360
gtctcctcag gtggaggcgg ttcaggcgga ggtggcagcg gcggtggcgg atcgcagtct    420
gtgctgactc agcctgcctc cgtgtctggg tctcctggac agtcgatcac catctccctg    480
gctggaacca gcagtgacgt tggtggttat aactatgtct cctggtacca acaacaccca    540
ggcaaagccc ccaaactcat gatttatgag acagtaagc ggcccctcagg ggtttctaat    600 cgcttctctg gctccaagtc tggcaacacg gcctccctga caatctctgg gctccaggct    660
gaggacgagg ctgattatta ctgcagctca tatacaacca ggagcactcg agttttcggc    720
ggagggacca agctggccgt cctaggtgcg ccgcagaac aaaaactcat ctcagaagag    780
gatctgaatg gggccgcaca tcaccatcat caccat                              816

<210> SEQ ID NO 48
<211> LENGTH: 33
<212> TYPE: DNA
<213> ORGANISM: Artificial
<220> FEATURE:
<223> OTHER INFORMATION: forward primer

<400> SEQUENCE: 48
ctcggatccg atgaagcgcg caagaccgtc tga                                  33

<210> SEQ ID NO 49
<211> LENGTH: 30
<212> TYPE: DNA
<213> ORGANISM: Artificial
<220> FEATURE:
<223> OTHER INFORMATION: reverse primer

<400> SEQUENCE: 49
ttcctcgagt tattcttggg caatgtatga                                      30

<210> SEQ ID NO 50
<211> LENGTH: 54
<212> TYPE: PRT
<213> ORGANISM: Homo sapiens

<400> SEQUENCE: 50

Met Asn Ser Asp Ser Glu Cys Pro Leu Ser His Asp Gly Tyr Cys Leu
 1               5                  10                  15

His Asp Gly Val Cys Met Tyr Ile Glu Ala Leu Asp Lys Tyr Ala Cys
                20                  25                  30

Asn Cys Val Val Gly Tyr Ile Gly Glu Arg Cys Gln Tyr Arg Asp Leu
            35                  40                  45
```

```
Lys Trp Trp Glu Leu Arg
    50

<210> SEQ ID NO 51
<211> LENGTH: 13
<212> TYPE: PRT
<213> ORGANISM: Staphylococcus aureus

<400> SEQUENCE: 51

Ala Lys Lys Leu Asn Asp Ala Gln Ala Pro Lys Ser Asp
1               5                   10

<210> SEQ ID NO 52
<211> LENGTH: 167
<212> TYPE: PRT
<213> ORGANISM: Artificial
<220> FEATURE:
<221> NAME/KEY: PEPTIDE
<223> OTHER INFORMATION: Fiber construct A1 EGF

<400> SEQUENCE: 52

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Pro Asp Val
    50                  55                  60

Ala Ser Leu Arg Gln Gln Val Glu Ala Leu Gln Gly Gln Val Gln His
65                  70                  75                  80

Leu Gln Ala Ala Phe Ser Gln Tyr Lys Lys Val Glu Leu Phe Pro Asn
                85                  90                  95

Gly Ala Lys Lys Leu Asn Asp Ala Gln Ala Pro Lys Ser Asp Pro Ser
            100                 105                 110

Ile Met Asn Ser Asp Ser Glu Cys Pro Leu Ser His Asp Gly Tyr Cys
        115                 120                 125

Leu His Asp Gly Val Cys Met Tyr Ile Glu Ala Leu Asp Lys Tyr Ala
    130                 135                 140

Cys Asn Cys Val Val Gly Tyr Ile Gly Glu Arg Cys Gln Tyr Arg Asp
145                 150                 155                 160

Leu Lys Trp Trp Glu Leu Arg
                165

<210> SEQ ID NO 53
<211> LENGTH: 265
<212> TYPE: PRT
<213> ORGANISM: Artificial
<220> FEATURE:
<223> OTHER INFORMATION: Fiber construct A7 EGF
<220> FEATURE:
<221> NAME/KEY: VARIANT
<222> LOCATION: (265)..(265)
<223> OTHER INFORMATION: Xaa is any  amino acid

<400> SEQUENCE: 53

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30
```

```
Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
 65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
        130                 135                 140

Ala Thr Gln Gly Pro Leu Thr Val Ser Glu Gly Lys Leu Ala Pro Asp
145                 150                 155                 160

Val Ala Ser Leu Arg Gln Val Glu Ala Leu Gln Gly Gln Val Gln
                165                 170                 175

His Leu Gln Ala Ala Phe Ser Gln Tyr Lys Lys Val Glu Leu Phe Pro
        180                 185                 190

Asn Gly Ala Lys Lys Leu Asn Asp Ala Gln Ala Pro Lys Ser Asp Pro
            195                 200                 205

Ser Ile Met Asn Ser Asp Ser Glu Cys Pro Leu Ser His Asp Gly Tyr
        210                 215                 220

Cys Leu His Asp Gly Val Cys Met Tyr Ile Glu Ala Leu Asp Lys Tyr
225                 230                 235                 240

Ala Cys Asn Cys Val Val Gly Tyr Ile Gly Glu Arg Cys Gln Tyr Arg
                245                 250                 255

Asp Leu Lys Trp Trp Glu Leu Arg Xaa
            260                 265

<210> SEQ ID NO 54
<211> LENGTH: 352
<212> TYPE: PRT
<213> ORGANISM: Artificial
<220> FEATURE:
<223> OTHER INFORMATION: G250 construct

<400> SEQUENCE: 54

Asp Ile Val Met Thr Gln Ser Gln Arg Phe Met Ser Thr Thr Val Gly
 1               5                  10                  15

Asp Arg Val Ser Ile Thr Cys Lys Ala Ser Gln Asn Val Val Ser Ala
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
 65                  70                  75                  80

Glu Asp Leu Ala Asp Phe Phe Cys Gln Gln Tyr Ser Asn Tyr Pro Trp
                85                  90                  95

Thr Phe Gly Gly Gly Thr Lys Leu Glu Ile Lys Gly Ser Gly Ser Thr
            100                 105                 110

Ser Gly Ser Gly Lys Ser Ser Glu Gly Lys Gly Thr Arg Asp Val Lys
        115                 120                 125
```

Leu Val Glu Ser Gly Gly Leu Val Lys Leu Gly Ser Leu Lys
    130                 135             140

Leu Ser Cys Ala Ala Ser Gly Phe Thr Phe Ser Asn Tyr Tyr Met Ser
145                 150                 155                 160

Trp Val Arg Gln Thr Pro Glu Lys Arg Leu Glu Leu Val Ala Ala Ile
                165                 170                 175

Asn Ser Asp Gly Gly Ile Thr Tyr Tyr Leu Asp Thr Val Lys Gly Arg
            180                 185                 190

Phe Thr Ile Ser Arg Asp Asn Ala Lys Asn Thr Leu Tyr Leu Gln Met
        195                 200                 205

Ser Ser Leu Lys Ser Glu Asp Thr Ala Leu Phe Tyr Cys Ala Arg His
    210                 215                 220

Arg Ser Gly Tyr Phe Ser Met Asp Tyr Trp Gly Gln Gly Thr Ser Val
225                 230                 235                 240

Thr Val Ser Ser Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

<210> SEQ ID NO 55
<211> LENGTH: 250
<212> TYPE: PRT
<213> ORGANISM: Artificial
<220> FEATURE:
<223> OTHER INFORMATION: C242 construct

<400> SEQUENCE: 55

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Val Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Phe Thr Phe Gly Pro Gly Thr Lys Leu Glu Leu Lys
            100                 105                 110

Arg Pro Pro Asp Phe Val Pro Pro Ala Ala Ser Phe Pro Asp His Ser
        115                 120                 125

Pro Arg Gly Gln Val Gln Leu Val Gln Ser Gly Pro Glu Leu Lys Lys
130                 135                 140

```
Pro Gly Glu Thr Val Lys Ile Ser Cys Lys Ala Ser Asp Tyr Thr Phe
145                 150                 155                 160

Thr Tyr Tyr Gly Met Asn Trp Val Lys Gln Ala Pro Gly Lys Gly Leu
            165                 170                 175

Lys Trp Met Gly Trp Ile Asp Thr Thr Thr Gly Glu Pro Thr Tyr Ala
        180                 185                 190

Glu Asp Phe Lys Gly Arg Ile Ala Phe Ser Leu Glu Thr Ser Ala Ser
            195                 200                 205

Thr Ala Tyr Leu Gln Ile Lys Asn Leu Lys Asn Glu Asp Thr Ala Thr
        210                 215                 220

Tyr Phe Cys Ala Arg Arg Gly Pro Tyr Asn Trp Tyr Phe Asp Val Trp
225                 230                 235                 240

Gly Gln Gly Thr Thr Val Thr Val Ser Ser
            245                 250
```

<210> SEQ ID NO 56
<211> LENGTH: 468
<212> TYPE: PRT
<213> ORGANISM: Artificial
<220> FEATURE:
<223> OTHER INFORMATION: Fiber construct A7 G250
<220> FEATURE:
<221> NAME/KEY: VARIANT
<222> LOCATION: (466)..(466)
<223> OTHER INFORMATION: Xaa is coded for by a stop codon

<400> SEQUENCE: 56

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Pro Asp Val
50                  55                  60

Ala Ser Leu Arg Gln Gln Val Glu Ala Leu Gln Gly Gln Val Gln His
65                  70                  75                  80

Leu Gln Ala Ala Phe Ser Gln Tyr Lys Lys Val Glu Leu Phe Pro Asn
            85                  90                  95

Gly Ala Lys Lys Leu Asn Asp Ala Gln Ala Pro Lys Ser Asp Pro Ser
        100                 105                 110

Ile Asp Ile Val Met Thr Gln Ser Gln Arg Phe Met Ser Thr Thr Val
    115                 120                 125

Gly Asp Arg Val Ser Ile Thr Cys Lys Ala Ser Gln Asn Val Val Ser
130                 135                 140

Ala Val Ala Trp Tyr Gln Gln Lys Pro Gly Gln Ser Pro Lys Leu Leu
145                 150                 155                 160

Ile Tyr Ser Ala Ser Asn Arg Tyr Thr Gly Val Pro Asp Arg Phe Thr
            165                 170                 175

Gly Ser Gly Ser Gly Thr Asp Phe Thr Leu Thr Ile Ser Asn Met Gln
        180                 185                 190

Ser Glu Asp Leu Ala Asp Phe Phe Cys Gln Gln Tyr Ser Asn Tyr Pro
    195                 200                 205

Trp Thr Phe Gly Gly Gly Thr Lys Leu Glu Ile Lys Gly Ser Gly Ser
210                 215                 220

Thr Ser Gly Ser Gly Lys Ser Ser Glu Gly Lys Gly Thr Arg Asp Val
225                 230                 235                 240
```

```
Lys Leu Val Glu Ser Gly Gly Gly Leu Val Lys Leu Gly Gly Ser Leu
                245                 250                 255

Lys Leu Ser Cys Ala Ala Ser Gly Phe Thr Phe Ser Asn Tyr Tyr Met
            260                 265                 270

Ser Trp Val Arg Gln Thr Pro Glu Lys Arg Leu Glu Leu Val Ala Ala
        275                 280                 285

Ile Asn Ser Asp Gly Gly Ile Thr Tyr Tyr Leu Asp Thr Val Lys Gly
    290                 295                 300

Arg Phe Thr Ile Ser Arg Asp Asn Ala Lys Asn Thr Leu Tyr Leu Gln
305                 310                 315                 320

Met Ser Ser Leu Lys Ser Glu Asp Thr Ala Leu Phe Tyr Cys Ala Arg
                325                 330                 335

His Arg Ser Gly Tyr Phe Ser Met Asp Tyr Trp Gly Gln Gly Thr Ser
            340                 345                 350

Val Thr Val Ser Ser Cys Pro Pro Cys Pro Ala Pro Glu Leu Leu Gly
        355                 360                 365

Gly Pro Ser Val Phe Leu Phe Pro Pro Lys Pro Lys Asp Thr Leu Met
    370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Asn Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
    450                 455                 460

Glu Xaa Leu Glu
465

<210> SEQ ID NO 57
<211> LENGTH: 565
<212> TYPE: PRT
<213> ORGANISM: Artificial
<220> FEATURE:
<223> OTHER INFORMATION: Fiber construct A7 G250
<220> FEATURE:
<221> NAME/KEY: VARIANT
<222> LOCATION: (563)..(563)
<223> OTHER INFORMATION: Xaa is coded for by a stop codon

<400> SEQUENCE: 57

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
```

-continued

```
            100                 105                 110
Thr Val Ala Ala Ala Pro Leu Met Val Ala Gly Asn Thr Leu Thr
            115                 120                 125
Met Gln Ser Gln Ala Pro Leu Thr Val His Asp Ser Lys Leu Ser Ile
            130                 135                 140
Ala Thr Gln Gly Pro Leu Thr Val Ser Glu Gly Lys Leu Ala Pro Asp
145                 150                 155                 160
Val Ala Ser Leu Arg Gln Gln Val Glu Ala Leu Gln Gly Gln Val Gln
                    165                 170                 175
His Leu Gln Ala Ala Phe Ser Gln Tyr Lys Lys Val Glu Leu Phe Pro
                    180                 185                 190
Asn Gly Ala Lys Lys Leu Asn Asp Ala Gln Ala Pro Lys Ser Asp Pro
                    195                 200                 205
Ser Ile Asp Ile Val Met Thr Gln Ser Gln Arg Phe Met Ser Thr Thr
            210                 215                 220
Val Gly Asp Arg Val Ser Ile Thr Cys Lys Ala Ser Gln Asn Val Val
225                 230                 235                 240
Ser Ala Val Ala Trp Tyr Gln Gln Lys Pro Gly Gln Ser Pro Lys Leu
                    245                 250                 255
Leu Ile Tyr Ser Ala Ser Asn Arg Tyr Thr Gly Val Pro Asp Arg Phe
            260                 265                 270
Thr Gly Ser Gly Ser Gly Thr Asp Phe Thr Leu Thr Ile Ser Asn Met
            275                 280                 285
Gln Ser Glu Asp Leu Ala Asp Phe Phe Cys Gln Gln Tyr Ser Asn Tyr
            290                 295                 300
Pro Trp Thr Phe Gly Gly Gly Thr Lys Leu Glu Ile Lys Gly Ser Gly
305                 310                 315                 320
Ser Thr Ser Gly Ser Gly Lys Ser Ser Glu Gly Lys Gly Thr Arg Asp
                    325                 330                 335
Val Lys Leu Val Glu Ser Gly Gly Leu Val Lys Leu Gly Gly Ser
            340                 345                 350
Leu Lys Leu Ser Cys Ala Ala Ser Gly Phe Thr Phe Ser Asn Tyr Tyr
            355                 360                 365
Met Ser Trp Val Arg Gln Thr Pro Glu Lys Arg Leu Glu Leu Val Ala
            370                 375                 380
Ala Ile Asn Ser Asp Gly Gly Ile Thr Tyr Tyr Leu Asp Thr Val Lys
385                 390                 395                 400
Gly Arg Phe Thr Ile Ser Arg Asp Asn Ala Lys Asn Thr Leu Tyr Leu
                    405                 410                 415
Gln Met Ser Ser Leu Lys Ser Glu Asp Thr Ala Leu Phe Tyr Cys Ala
                    420                 425                 430
Arg His Arg Ser Gly Tyr Phe Ser Met Asp Tyr Trp Gly Gln Gly Thr
            435                 440                 445
Ser Val Thr Val Ser Ser Cys Pro Pro Cys Pro Ala Pro Glu Leu Leu
            450                 455                 460
Gly Gly Pro Ser Val Phe Leu Phe Pro Pro Lys Pro Lys Asp Thr Leu
465                 470                 475                 480
Met Ile Ser Arg Thr Pro Glu Val Thr Cys Val Val Val Asp Val Ser
                    485                 490                 495
His Glu Asp Pro Glu Val Lys Phe Asn Trp Tyr Val Asp Gly Val Glu
                    500                 505                 510
Val His Asn Ala Lys Thr Lys Pro Arg Glu Glu Gln Tyr Asn Ser Thr
            515                 520                 525
```

```
Tyr Arg Val Val Ser Val Leu Thr Val Leu His Gln Asp Trp Leu Asn
    530                 535                 540

Gly Lys Glu Tyr Lys Cys Lys Val Ser Asn Lys Ala Leu Pro Ala Pro
545                 550                 555                 560

Ile Glu Xaa Leu Glu
            565

<210> SEQ ID NO 58
<211> LENGTH: 368
<212> TYPE: PRT
<213> ORGANISM: Artificial
<220> FEATURE:
<223> OTHER INFORMATION: Fiber construct A1 C242
<220> FEATURE:
<221> NAME/KEY: VARIANT
<222> LOCATION: (366)..(366)
<223> OTHER INFORMATION: Xaa is coded for by a stop codon

<400> SEQUENCE: 58

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Pro Asp Val
    50                  55                  60

Ala Ser Leu Arg Gln Gln Val Glu Ala Leu Gln Gly Gln Val Gln His
65                  70                  75                  80

Leu Gln Ala Ala Phe Ser Gln Tyr Lys Lys Val Glu Leu Phe Pro Asn
                85                  90                  95

Gly Ala Lys Lys Leu Asn Asp Ala Gln Ala Pro Lys Ser Asp Pro Ser
            100                 105                 110

Ile Asp Ile Val Met Thr Gln Ala Ala Pro Ser Val Pro Val Thr Pro
        115                 120                 125

Gly Glu Ser Val Ser Ile Ser Cys Arg Ser Ser Lys Ser Leu Leu His
    130                 135                 140

Ser Asn Gly Asn Thr Tyr Leu Tyr Trp Phe Leu Gln Arg Pro Gly Gln
145                 150                 155                 160

Ser Pro Gln Leu Leu Ile Tyr Arg Met Ser Asn Leu Val Ser Gly Val
                165                 170                 175

Pro Asp Arg Phe Ser Gly Ser Gly Ser Gly Thr Ala Phe Thr Leu Arg
            180                 185                 190

Ile Ser Arg Val Glu Ala Glu Asp Val Gly Val Tyr Tyr Cys Leu Gln
        195                 200                 205

His Leu Glu Tyr Pro Phe Thr Phe Gly Pro Gly Thr Lys Leu Glu Leu
    210                 215                 220

Lys Arg Pro Pro Asp Phe Val Pro Ala Ala Ser Phe Pro Asp His
225                 230                 235                 240

Ser Pro Arg Gly Gln Val Gln Leu Val Gln Ser Gly Pro Glu Leu Lys
                245                 250                 255

Lys Pro Gly Glu Thr Val Lys Ile Ser Cys Lys Ala Ser Asp Tyr Thr
            260                 265                 270

Phe Thr Tyr Tyr Gly Met Asn Trp Val Lys Gln Ala Pro Gly Lys Gly
        275                 280                 285

Leu Lys Trp Met Gly Trp Ile Asp Thr Thr Gly Glu Pro Thr Tyr
```

```
                    290                 295                 300
Ala Glu Asp Phe Lys Gly Arg Ile Ala Phe Ser Leu Glu Thr Ser Ala
305                 310                 315                 320

Ser Thr Ala Tyr Leu Gln Ile Lys Asn Leu Lys Asn Glu Asp Thr Ala
                325                 330                 335

Thr Tyr Phe Cys Ala Arg Arg Gly Pro Tyr Asn Trp Tyr Phe Asp Val
                340                 345                 350

Trp Gly Gln Gly Thr Thr Val Thr Val Ser Ser Leu Asp Xaa Leu Glu
                355                 360                 365

<210> SEQ ID NO 59
<211> LENGTH: 465
<212> TYPE: PRT
<213> ORGANISM: Artificial
<220> FEATURE:
<223> OTHER INFORMATION: fiber construct A7 C242
<220> FEATURE:
<221> NAME/KEY: VARIANT
<222> LOCATION: (463)..(463)
<223> OTHER INFORMATION: Xaa is coded for by a stop codon

<400> SEQUENCE: 59

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Pro Asp
145                 150                 155                 160

Val Ala Ser Leu Arg Gln Gln Val Glu Ala Leu Gln Gly Gln Val Gln
                165                 170                 175

His Leu Gln Ala Ala Phe Ser Gln Tyr Lys Lys Val Glu Leu Phe Pro
            180                 185                 190

Asn Gly Ala Lys Lys Leu Asn Asp Ala Gln Ala Pro Lys Ser Asp Pro
        195                 200                 205

Ser Ile Asp Ile Val Met Thr Gln Ala Ala Pro Ser Val Pro Val Thr
    210                 215                 220

Pro Gly Glu Ser Val Ser Ile Ser Cys Arg Ser Ser Lys Ser Leu Leu
225                 230                 235                 240

His Ser Asn Gly Asn Thr Tyr Leu Tyr Trp Phe Leu Gln Arg Pro Gly
                245                 250                 255

Gln Ser Pro Gln Leu Leu Ile Tyr Arg Met Ser Asn Leu Val Ser Gly
            260                 265                 270
```

```
Val Pro Asp Arg Phe Ser Gly Ser Gly Ser Gly Thr Ala Phe Thr Leu
        275                 280                 285

Arg Ile Ser Arg Val Glu Ala Glu Asp Val Gly Val Tyr Tyr Cys Leu
        290                 295                 300

Gln His Leu Glu Tyr Pro Phe Thr Phe Gly Pro Gly Thr Lys Leu Glu
305                 310                 315                 320

Leu Lys Arg Pro Pro Asp Phe Val Pro Ala Ala Ser Phe Pro Asp
                325                 330                 335

His Ser Pro Arg Gly Gln Val Gln Leu Val Gln Ser Gly Pro Glu Leu
                340                 345                 350

Lys Lys Pro Gly Glu Thr Val Lys Ile Ser Cys Lys Ala Ser Asp Tyr
            355                 360                 365

Thr Phe Thr Tyr Tyr Gly Met Asn Trp Val Lys Gln Ala Pro Gly Lys
        370                 375                 380

Gly Leu Lys Trp Met Gly Trp Ile Asp Thr Thr Thr Gly Glu Pro Thr
385                 390                 395                 400

Tyr Ala Glu Asp Phe Lys Gly Arg Ile Ala Phe Ser Leu Glu Thr Ser
                405                 410                 415

Ala Ser Thr Ala Tyr Leu Gln Ile Lys Asn Leu Lys Asn Glu Asp Thr
            420                 425                 430

Ala Thr Tyr Phe Cys Ala Arg Arg Gly Pro Tyr Asn Trp Tyr Phe Asp
        435                 440                 445

Val Trp Gly Gln Gly Thr Thr Val Thr Val Ser Ser Leu Asp Xaa Leu
    450                 455                 460

Glu
465

<210> SEQ ID NO 60
<211> LENGTH: 58
<212> TYPE: PRT
<213> ORGANISM: Artificial
<220> FEATURE:
<223> OTHER INFORMATION: Affibody ZIgG

<400> SEQUENCE: 60

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 61
<211> LENGTH: 58
<212> TYPE: PRT
<213> ORGANISM: Artificial
<220> FEATURE:
<223> OTHER INFORMATION: Affibody ZIgA

<400> SEQUENCE: 61

Val Asp Asn Lys Phe Asn Lys Glu Thr Ile Gln Ala Ser Gln Glu Ile
1               5                   10                  15

Arg Leu Leu Pro Asn Leu Asn Gly Arg Gln Lys Leu Ala Phe Ile His
                20                  25                  30

Ser Leu Leu Asp Asp Pro Ser Gln Ser Ala Asn Leu Leu Ala Glu Ala
            35                  40                  45
```

-continued

Lys Lys Leu Asn Asp Ala Gln Ala Pro Lys
    50                  55

<210> SEQ ID NO 62
<211> LENGTH: 271
<212> TYPE: PRT
<213> ORGANISM: Artificial
<220> FEATURE:
<223> OTHER INFORMATION: Recombinant Fiber A7 ZIgG
<220> FEATURE:
<221> NAME/KEY: VARIANT
<222> LOCATION: (269)..(269)
<223> OTHER INFORMATION: Xaa is coded for by a stop codon

<400> SEQUENCE: 62

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Pro Asp
145                 150                 155                 160

Val Ala Ser Leu Arg Gln Gln Val Glu Ala Leu Gln Gly Gln Val Gln
                165                 170                 175

His Leu Gln Ala Ala Phe Ser Gln Tyr Lys Lys Val Glu Leu Phe Pro
            180                 185                 190

Asn Gly Ala Lys Lys Leu Asn Asp Ala Gln Ala Pro Lys Ser Asp Pro
        195                 200                 205

Ser Ile Val Asp Asn Lys Phe Asn Lys Glu Gln Gln Asn Ala Phe Tyr
    210                 215                 220

Glu Ile Leu His Leu Pro Asn Leu Asn Glu Glu Gln Arg Asn Ala Phe
225                 230                 235                 240

Ile Gln Ser Leu Lys Asp Asp Pro Ser Gln Ser Ala Asn Leu Leu Ala
                245                 250                 255

Glu Ala Lys Lys Leu Asn Asp Ala Gln Ala Pro Lys Xaa Leu Glu
            260                 265                 270

<210> SEQ ID NO 63
<211> LENGTH: 271
<212> TYPE: PRT
<213> ORGANISM: Artificial
<220> FEATURE:
<223> OTHER INFORMATION: Recombinant Fiber A7 ZIgA
<220> FEATURE:
<221> NAME/KEY: VARIANT
<222> LOCATION: (269)..(269)

<223> OTHER INFORMATION: Xaa is coded for by a stop codon

<400> SEQUENCE: 63

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Pro Asp
145                 150                 155                 160

Val Ala Ser Leu Arg Gln Gln Val Glu Ala Leu Gln Gly Gln Val Gln
                165                 170                 175

His Leu Gln Ala Ala Phe Ser Gln Tyr Lys Lys Val Glu Leu Phe Pro
            180                 185                 190

Asn Gly Ala Lys Lys Leu Asn Asp Ala Gln Ala Pro Lys Ser Asp Pro
        195                 200                 205

Ser Ile Val Asp Asn Lys Phe Asn Lys Glu Thr Ile Gln Ala Ser Gln
    210                 215                 220

Glu Ile Arg Leu Leu Pro Asn Leu Asn Gly Arg Gln Lys Leu Ala Phe
225                 230                 235                 240

Ile His Ser Leu Leu Asp Asp Pro Ser Gln Ser Ala Asn Leu Leu Ala
                245                 250                 255

Glu Ala Lys Lys Leu Asn Asp Ala Gln Ala Pro Lys Xaa Leu Glu
            260                 265                 270
```

<210> SEQ ID NO 64
<211> LENGTH: 332
<212> TYPE: PRT
<213> ORGANISM: Artificial
<220> FEATURE:
<223> OTHER INFORMATION: Recombinant FIber A7 ZIgG/ZigA
<220> FEATURE:
<221> NAME/KEY: VARIANT
<222> LOCATION: (330)..(330)
<223> OTHER INFORMATION: Xaais coded for by a stop codon

<400> SEQUENCE: 64

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
```

```
                50                  55                  60
Lys Met Gly Asn Gly Leu Ser Leu Asp Glu Ala Gly Asn Leu Thr Ser
 65                  70                  75                  80

Gln Asn Val Thr Thr Val Ser Pro Pro Leu Lys Lys Thr Lys Ser Asn
                 85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Pro Asp
145                 150                 155                 160

Val Ala Ser Leu Arg Gln Val Glu Ala Leu Gln Gly Gln Val Gln
                165                 170                 175

His Leu Gln Ala Ala Phe Ser Gln Tyr Lys Lys Val Glu Leu Phe Pro
            180                 185                 190

Asn Gly Ala Lys Lys Leu Asn Asp Ala Gln Ala Pro Lys Ser Asp Pro
        195                 200                 205

Ser Ile Val Asp Asn Lys Phe Asn Lys Glu Gln Gln Asn Ala Phe Tyr
210                 215                 220

Glu Ile Leu His Leu Pro Asn Leu Asn Glu Glu Gln Arg Asn Ala Phe
225                 230                 235                 240

Ile Gln Ser Leu Lys Asp Asp Pro Ser Gln Ser Ala Asn Leu Leu Ala
                245                 250                 255

Glu Ala Lys Lys Leu Asn Asp Ala Gln Ala Pro Lys Ser Ser Thr Val
            260                 265                 270

Asp Asn Lys Phe Asn Lys Glu Thr Ile Gln Ala Ser Gln Glu Ile Arg
        275                 280                 285

Leu Leu Pro Asn Leu Asn Gly Arg Gln Lys Leu Ala Phe Ile His Ser
290                 295                 300

Leu Leu Asp Asp Pro Ser Gln Ser Ala Asn Leu Leu Ala Glu Ala Lys
305                 310                 315                 320

Lys Leu Asn Asp Ala Gln Ala Pro Lys Xaa Leu Glu
                325                 330

<210> SEQ ID NO 65
<211> LENGTH: 332
<212> TYPE: PRT
<213> ORGANISM: Artificial
<220> FEATURE:
<223> OTHER INFORMATION: Recombinant Fiber A7 ZIgG/ZIgG
<220> FEATURE:
<221> NAME/KEY: VARIANT
<222> LOCATION: (330)..(330)
<223> OTHER INFORMATION: Xaa is coded for by a stop codon

<400> SEQUENCE: 65

Met Lys Arg Ala Arg Pro Ser Glu Asp Thr Phe Asn Pro Val Tyr Pro
 1               5                  10                  15

Tyr Asp Thr Glu Thr Gly Pro Pro Thr Val Pro Phe Leu Thr Pro Pro
             20                  25                  30

Phe Val Ser Pro Asn Gly Phe Gln Glu Ser Pro Pro Gly Val Leu Ser
         35                  40                  45

Leu Arg Leu Ser Glu Pro Leu Val Thr Ser Asn Gly Met Leu Ala Leu
    50                  55                  60
```

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Thr Lys Ser Asn
            85                  90                  95

Ile Asn Leu Glu Ile Ser Ala Pro Leu Thr Val Thr Ser Glu Ala Leu
                100                 105                 110

Thr Val Ala Ala Ala Pro Leu Met Val Ala Gly Asn Thr Leu Thr
            115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Pro Asp
145                 150                 155                 160

Val Ala Ser Leu Arg Gln Gln Val Glu Ala Leu Gln Gly Gln Val Gln
                165                 170                 175

His Leu Gln Ala Ala Phe Ser Gln Tyr Lys Lys Val Glu Leu Phe Pro
            180                 185                 190

Asn Gly Ala Lys Lys Leu Asn Asp Ala Gln Ala Pro Lys Ser Asp Pro
            195                 200                 205

Ser Ile Val Asp Asn Lys Phe Asn Lys Glu Gln Gln Asn Ala Phe Tyr
210                 215                 220

Glu Ile Leu His Leu Pro Asn Leu Asn Glu Glu Gln Arg Asn Ala Phe
225                 230                 235                 240

Ile Gln Ser Leu Lys Asp Asp Pro Ser Gln Ser Ala Asn Leu Leu Ala
            245                 250                 255

Glu Ala Lys Lys Leu Asn Asp Ala Gln Ala Pro Lys Ser Ser Thr Val
            260                 265                 270

Asp Asn Lys Phe Asn Lys Glu Gln Gln Asn Ala Phe Tyr Glu Ile Leu
            275                 280                 285

His Leu Pro Asn Leu Asn Glu Glu Gln Arg Asn Ala Phe Ile Gln Ser
            290                 295                 300

Leu Lys Asp Asp Pro Ser Gln Ser Ala Asn Leu Leu Ala Glu Ala Lys
305                 310                 315                 320

Lys Leu Asn Asp Ala Gln Ala Pro Lys Xaa Leu Glu
            325                 330

<210> SEQ ID NO 66
<211> LENGTH: 18
<212> TYPE: PRT
<213> ORGANISM: Artificial
<220> FEATURE:
<223> OTHER INFORMATION: Linker sequence

<400> SEQUENCE: 66

Pro Pro Asp Phe Val Pro Pro Ala Ala Ser Phe Pro Asp His Ser Pro
1               5                   10                  15

Arg Gly

<210> SEQ ID NO 67
<211> LENGTH: 8
<212> TYPE: PRT
<213> ORGANISM: Artificial
<220> FEATURE:
<223> OTHER INFORMATION: Linker peptide

```
<400> SEQUENCE: 67

Lys Lys Val Glu Leu Phe Pro Asn
1               5

<210> SEQ ID NO 68
<211> LENGTH: 13
<212> TYPE: PRT
<213> ORGANISM: Artificial
<220> FEATURE:
<223> OTHER INFORMATION: Staph-A linker peptide

<400> SEQUENCE: 68

Ala Lys Lys Leu Asn Asp Ala Gln Ala Pro Lys Ser Asp
1               5                   10

<210> SEQ ID NO 69
<211> LENGTH: 33
<212> TYPE: DNA
<213> ORGANISM: Artificial
<220> FEATURE:
<223> OTHER INFORMATION: Ad5 WT fiber shaft repeat 17

<400> SEQUENCE: 69
tttacagctt caaacaattc caaaaagctt gag                                 33

<210> SEQ ID NO 70
<211> LENGTH: 37
<212> TYPE: DNA
<213> ORGANISM: Artificial
<220> FEATURE:
<223> OTHER INFORMATION: Ad5 WT fiber shaft repeat 22

<400> SEQUENCE: 70
ggaaacaaaa ataatgataa gctaactttg tgtgacc                             37

<210> SEQ ID NO 71
<211> LENGTH: 18
<212> TYPE: PRT
<213> ORGANISM: Artificial
<220> FEATURE:
<223> OTHER INFORMATION: peptide ligand

<400> SEQUENCE: 71

Pro Pro Asp Phe Val Pro Pro Ala Ala Ser Phe Pro Asp His Ser Pro
1               5                   10                  15

Arg Gly
```

MODIFIED VIRUS COMPRISING ONE OR MORE NON-NATIVE POLYPEPTIDES

This application is a national stage application of PCT/GB0103252, filed Jul. 19, 2001, which claims the benefit of the filing date of Great Britain Application No. 0017720, filed Jul. 19, 2000, in the Great Britain Intellectual Property Office.

FIELD OF THE INVENTION

The present invention relates to novel recombinant viruses suitable for use in gene therapy. Such recombinant viruses exhibit an altered tropism conferred by incorporation of one or more non-native polypeptides into one or more viral components, or the replacement of such components by non-native polypeptides. These non-native polypeptides can comprise elements which mimic the structure of the original viral component so as to permit inclusion of the polypeptide in functional virion particles. These non-native polypeptides can also comprise elements which confer a non-native ligand binding function (i.e. altered tropism) to such virion particles. Essentially, the non-native polypeptides employed in the invention have primary and secondary amino acid structures that enable their correct folding in the nucleus or cytosol of mammalian host cells and their subsequent transport through the nuclear membrane. Such structures permit the assembly of functional recombinant virion particles with an intact non-native binding function and thus an altered tropism.

DESCRIPTION OF THE RELATED ART

Clinical gene therapy was introduced in 1989. The aim at that time was to correct gene defects in the immune system via the in vitro introduction of a healthy gene into the defective cells of the patient and transfusion of the treated cells back to the patient. Since that time, the indications and possible molecular uses of gene therapy have increased dramatically. Today, ten years after its introduction, one can envisage the use of gene therapy to treat e.g. vascular diseases, cancer, inflammatory diseases and infectious diseases such as HIV.

At present, however, gene therapy is still not a useful method in human medicine. One main reason is that gene therapy demands the packaging of the genes to be delivered into gene-carriers, or vectors, which can be administered to patients and which will target the genes only to the intended cells. Such vectors have so far not been available in reliable form.

Several classes of viruses have been considered as vectors for gene therapy applications, the most commonly used being adenoviruses, retroviruses, lentiviruses and adeno-associated viruses.

Ideal vectors for gene therapy would be those which can be administered systemically and yet deliver the desired genetic material specifically to desired cells or tissues. However, the viruses currently considered for human gene therapy applications have a broad tropism, being able to infect many different types of cells in the human body. This limits the potential safety of viral vectors and prohibits their use for systemic administration. For this reason, the development of targeted virus vectors, capable of infecting only selected cells, has been described as the holy grail of gene therapy.

One of the most widely investigated group of vectors for gene therapy applications is the adenoviruses. Human adenoviruses are divided into six hemagglutination groups (A-F) and each hemagglutination group is further subdivided into different serotypes. All in all there exist more than 40 different human adenovirus serotypes. The adenovirus which has been most frequently used for human gene therapy is adenovirus type 5 (Ad5) which belongs to hemagglutination group C.

Adenoviruses (Ad) are DNA viruses without an envelope, shaped as regular icosahedrons with a diameter of 60-85 nm.

The adenoviral capsid comprises 252 capsomeres, 240 hexons and 12 pentons (Ginsberg et al., Virology, 28, 782-83 (1966)). The hexons and pentons are derived from three viral proteins. The hexon comprises three identical proteins of 967 amino acids each, namely polypeptide II. The penton contains a base, which is bound to the capsid, and a fiber, which is non-covalently bound to, and projects from, the penton base. Proteins IX, VI and IIIa also are present in the adenoviral coat and are thought to stabilise the viral capsid.

Cell binding takes place through the fiber proteins, anchored to the virion at the vertices of the icosahedron. The fiber protein is not necessary for assembly and release of intact virions. Assembly of virions take place in the nucleus of infected cells.

The fiber protein, which is a homotrimer of a fiber polypeptide (namely adenoviral polypeptide IV), contains three functionally different parts: an N-terminal tail anchoring the fiber non-covalently to the penton base in the virion and which furthermore contains the nuclear-localization signal; a shaft domain comprising a variable number of repeats of a ~15 amino acid fiber shaft motif, (e.g. which is repeated six times in Ad3 and 22 times in Ad2 and Ad5); and a C-terminal globular domain, the knob, which contains the ligand which binds to the cellular Ad-receptor (Chrobozek et al., Microbiology and Immunology, (1995), p. 163-200). The knob is also functionally responsible for fiber trimerisation (i.e. it incorporates a trimerisation motif).

Each shaft repeat has two three-amino acid regions which form beta-sheets and two amino acid regions which constitute the turns of the native extended fiber shaft. The crystal structure of the trimerised, cell binding domain has been determined and shows a unique topology different from other anti-parallel β-sandwiches (Xia et al., Structure 2: 1259-1270, (1993)). Binding of the fiber to the penton base of the virion can take place also in a cell-free system, i.e. the fiber can bind to fiberless virions (Boudin et al., Virology, 116: 589-604, (1982)).

Efforts to modify adenovirus fibers (e.g. produce recombinant fiber proteins) in order to modify the properties of adenovirus vectors, for example by altering tropism or cell binding, have been made and have been reported in the prior art.

The adenovirus fiber protein performs several biological functions which must be retained in order to produce active virus particles. The following fiber features are deemed to be of key importance in the construction of functional modified fiber proteins:

i) the ability to form parallel homotrimers. This function is mediated by the N-terminal amino acid sequence of the wild type fiber knob.

ii) the ability to bind to the penton base to form penton capsomeres. This function is mediated by the wild type fiber tail.

iii) the ability to express a cell binding ligand allowing for attachment to target cells. In the native situation, this function is mediated by the wild type fiber knob (which binds to the cellular Ad-receptor).

iv) the capability of transport into the nucleus of infected cells, which is vital to virus formation. This function is mainly, but perhaps not exclusively, mediated by the wild type fiber tail.

Previous attempts to change the tropism of adenovirus have involved genetic modification of fibers and knobs. However, this approach has not proved to be very successful. A major problem has been the incorporation of novel ligands in a functional context, which are capable of changing the tropism without interfering with the trimerisation of the fiber. For example, a short peptide ligand has been added C-terminally of the knob (Michael et al., Gene Therapy, 2: 660-8, (1995)) and a nonapeptide has been introduced into one of the knob "loops" (Dmitriev et al., J. Virol., 72(12):9706-9713 (1998)). However, the knob has a very complex structure due to interactions between the three fiber subunits which are necessary to conserve cell binding and trimerisation. Therefore, the knob only tolerates insertion of a few amino acids and no general method for construction of functional, genetically re-targeted adenovirus fibers exists to date.

Attempts have also been made to introduce new ligands into other parts of the adenovirion. By introducing the FLAG tetra-amino acid motif into the Ad penton, it has been shown possible to target Ad to cells normally not infected by Ad. The re-targeting was achieved by targeting with a bi-specific antibody where one specificity was directed against the FLAG peptide and the other against the new target cell (Wickham et al., J. Virol., 70: 6831-6838, (1996)).

A previously unaddressed problem encountered in the production of efficient recombinant viruses for gene therapy, is that of ensuring the functional folding of recombinant components upon expression in the nucleus and cytosol of host cells. This is particularly relevant where the wild-type virus to be engineered employs component expression in these intracellular locations during replication, for example, as in adenovirus. Folded protein structures, particularly those which rely on disulphide bonds in cysteine bridges to maintain a functionally correct conformation, for example those derived from antibodies, can be rendered mis-folded and non-functional when expressed in the reducing environment of the nucleus and cytosol as part of a recombinant viral component. Thus, there exists in the art an unsatisfied and previously unappreciated need for protein structures which can retain a functional conformation when expressed as viral components in these cellular compartments, such that the binding functions which the structures comprise or support retain a binding function, particularly in the absence of the ligand for which binding is desired.

SUMMARY OF THE INVENTION

Disclosed herein is a modified virus comprising one or more non-native polypeptides, which polypeptid(s) comprises one or more framework moieties which possesses a folded three dimensional structure, each framework moiety containing one or more binding moieties, which polypeptide is capable of being expressed in the cytoplasm and nucleus of a mammalian host cell in a conformation which is maintained in the absence of a ligand for the binding moieties, the conformation allowing the binding moieties subsequently to bind with the ligand, and which polypeptide is capable of transport through the nuclear membrane, wherein the modified virus has an altered tropism conferred by the binding moieties. Further disclosed herein is a modified viral protein comprising a non-native polypeptide as described above, as well as a cell containing the modified virus or viral protein.

Further disclosed herein is a method for producing the modified virus described above in cell culture comprising genetically modifying a virus to produce a modified virus comprising one or more non-native polypeptides, which polypeptide comprises one or more framework moieties each containing one or more binding moieties, which polypeptide is capable of being expressed in the cytoplasm and nucleus of a mammalian host cell in a conformation which is maintained in the absence of a ligand for the binding moieties, the conformation allowing the binding moieties subsequently to bind with the ligand, and which polypeptide is capable of transport though the nuclear membrane, wherein the modified virus has an altered tropism conferred by the binding moieties; infecting permissive cells with the modified virus; culturing the cells to produce the virus; and harvesting, and optionally, purifying the modified virus produced.

Further disclosed herein is a method of regulating the replication of the modified virus as comprising: constructing a modified virus such that a cleavage site is positioned between a binding moiety required for cell infection and the remainder of the recombinant viral component of which the binding moiety forms part; and, bringing the recombinant virus into contact with a cleavage agent or cleavage means capable of cleaving the binding moiety from the viral component and thereby preventing the recombinant virus from undergoing further infection cycles.

Further disclosed herein is a method of determining the suitability of a non-native polypeptide for use in the preparation of a viral vector by determining its solubility in a cell system comprising: expressing the non-native polypeptide or a viral component protein comprising the non-native polypeptide in permissive cells; subjecting the cells to lysis to produce a cell lysate; separating the soluble and insoluble fractions of the cell lysate; analysing the soluble and insoluble fractions of the cell lysate for the content of the non-native polypeptide or viral component protein comprising the non-native polypeptide; and comparing the relative content of the non-native polypeptide or viral component protein comprising the non-native polypeptide in the soluble and insoluble fractions.

Further disclosed herein is a method of assaying the solubility of a non-native polypeptide of claim 41, which method comprises: expressing the non-native polypeptide in permissive cells; subjecting the cells to lysis to produce a cell lysate; separating the soluble and insoluble fractions of the cell lysate; analysing the soluble and insoluble fractions of the cell lysate for the content of the non-native polypeptide or viral component protein comprising the non-native polypeptide; and, comparing the relative content of the non-native polypeptide or viral component protein comprising the non-native polypeptide in the soluble and insoluble fractions.

Further disclosed herein is a method of assaying the solubility of a modified viral protein comprising: expressing the viral component protein comprising the non-native polypeptide in permissive cells; subjecting the cells to lysis to produce a cell lysate; separating the soluble and insoluble fractions of the cell lysate; analysing the soluble and insoluble fractions of the cell lysate for the content of the non-native polypeptide or viral component protein comprising the non-native polypeptide; and comparing the relative content of the non-native polypeptide or viral component protein comprising the non-native polypeptide in the soluble and insoluble fractions.

Further disclosed herein is a modified virus for use in therapy and in the preparation of a medicament for the treatment of tumour cells or proliferating cells. Further disclosed herein is a pharmaceutical composition comprising the modified virus and a pharmaceutically acceptable carrier or excipient.

DETAILED DESCRIPTION

Figure 1:
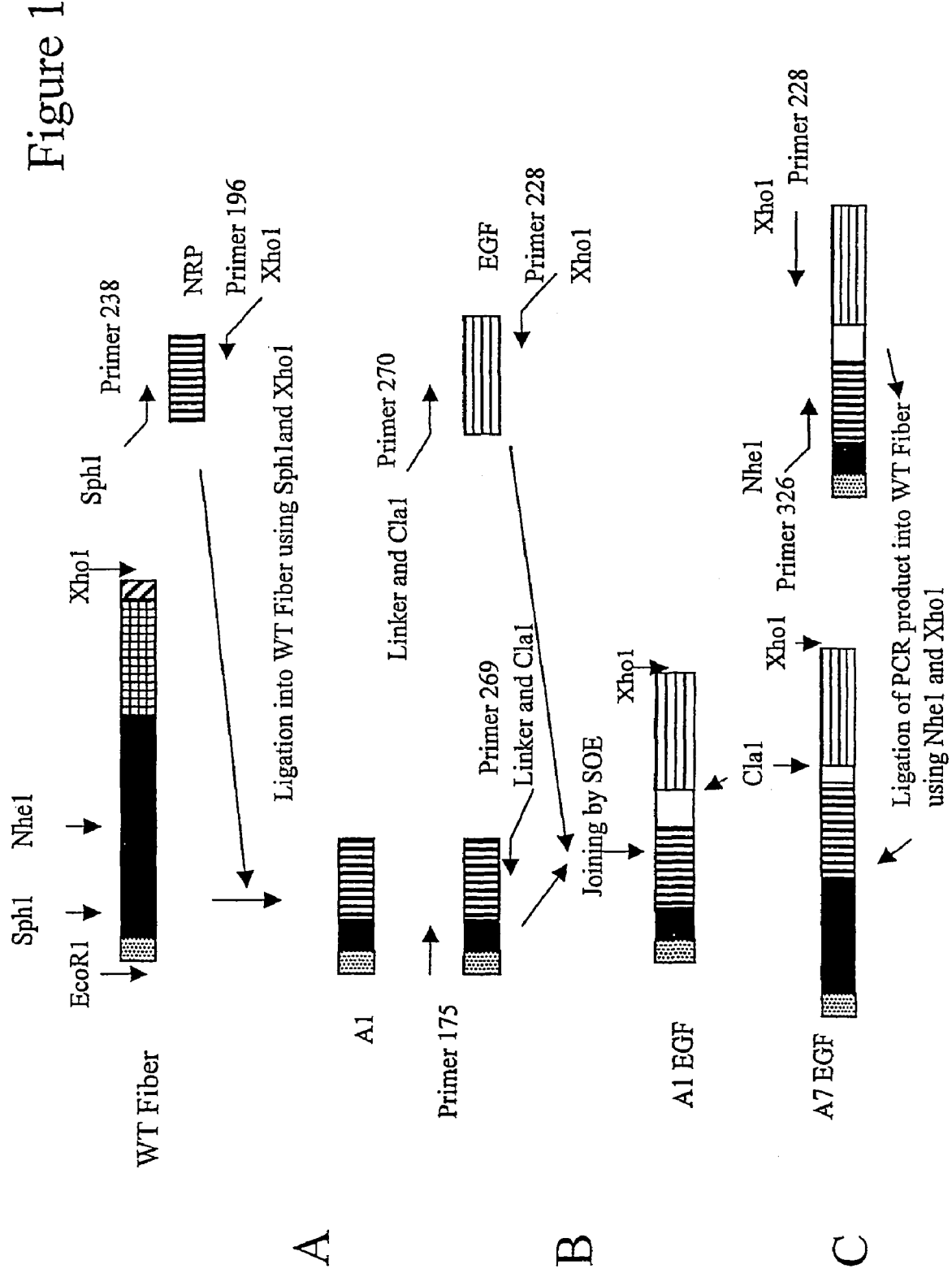
FIG. 1 shows a schematic description of the sequence of construction of different recombinant fibers.

There are therefore major problems associated with the genetic engineering of Adenovirus fibers useful in the construction of recombinant re-targeted adenovirus (Ad-virus) for human gene therapy. These problems are deemed to be particularly important since more patients have been treated with adenovirus vectors than with any other type of vector (Trapnell et al., Biotechnology, 5: 617-625, (1994)). The present invention is directed towards circumventing such problems in the construction of genetically re-targeted viruses for gene therapy, where the new viral tropism has been accomplished by the introduction of a new cell binding ligand into a viral component protein.

The invention described herein relates in part to the production of functional recombinant adenoviral fiber proteins with a new tropism facilitated by removing or ablating (e.g. blocking or inactivating) the native cell binding domain and either replacing it with, or adding, a non-native polypeptide comprising an external cell binding ligand and an external trimerisation motif.

Curiel et al. in WO 99/41359, Wickham et al. in WO 98/54346 and Spooner and Epenetos in U.S. Pat. No. 5,885, 808 disclose various modifications to adenoviral components with the aim of producing recombinant viruses with an altered tropism. None of the these disclosures provide a solution to, or indeed address or even recognise, the problems associated with the expression of functional non-native viral components in the nucleus and cytosol of host cells, a problem solved by the present invention.

Thus, in one aspect the invention provides a modified virus comprising a non-native polypeptide, which polypeptide comprises one or more framework moieties each containing one or more binding moieties, which polypeptide is capable of being expressed in the cytoplasm and nucleus of a mammalian host cell in a conformation which is maintained in the absence of a ligand for said binding moieties, said conformation allowing said binding moieties subsequently to bind with said ligand, and which polypeptide is capable of transport though the nuclear membrane, wherein said modified virus has an altered tropism conferred by said binding moieties.

A "modified" virus according to the invention is thus a virus which differs to a native (i.e. wild-type) virus. Generally speaking, the virus is modified such that a component of the virus is altered structurally over a native or wild-type (i.e. unmodified) component, or such that a structural component or feature is added to the virus, which is not present in the native or wild-type form. Advantageously, according to the present invention, a property or behaviour of the component is altered. In other words, the modified virus, differs functionally over an unmodified (native/wild-type) virus (e.g. by exhibiting an altered tropism). As discussed above (and also further below), the virus is conveniently modified using genetic engineering techniques. Accordingly, a modified virus according to the present invention is advantageously a recombinant virus.

A modified virus according to the invention can be derived from any virus, and in particular any virus which may be used as the basis of a viral vector for gene therapy. Representative viral families include adenoviruses, retroviruses, lentiviruses and adeno-associated viruses and particularly include members of the family Adenoviridae or other virus families where viral structural components are synthesized and/or assembled in the nucleus or cytosol of the host cell, such as Reoviridae, Picornaviridae, Parvoviridae, Papovaviridae and Caliciviridae. In a preferred aspect, modified viruses of the invention are modified forms of adenoviruses, in particular Human adenoviruses and more particularly Human adenovirus type 5.

"Non-native polypeptide" as defined herein is a polypeptide sequence of two or more amino acids, the complete sequence of which is not found in a functionally equivalent position in the amino acid sequence of the wild-type virus, or more particularly in the wild-type viral component protein to be engineered.

In certain preferred embodiments of the invention, the "non-native polypeptide" may also be non-native in the sense of not occurring in nature, i.e. being a synthetically or artificially constructed or prepared polypeptide.

According to the present invention, the conformation of the non-native polypeptide after expression in the intracellular environment and, more importantly, also its conformation in the extracellular environment, should be such that it is capable of binding to a desired ligand, e.g. a receptor or other molecule expressed on the outer surface of a target cell for the modified virus.

As mentioned above, advantageously according to the present invention, the non-native polypeptide, when expressed in the cytoplasm of a mammalian cell has a conformation which may be maintained in the absence of a ligand for the binding moiety(ies) of the polypeptide. Such a conformation is thus a stable conformation. In other words, upon expression in the cytoplasm, the polypeptide assumes a conformation which is maintained in the cytoplasm, and when the polypeptide is transported into the nucleus and incorporated or assembled into a viral particle. Moreover, the conformation is such that the binding moiety or moieties of the polypeptide is or are able to bind to their ligand, when exposed to it.

Thus, an important feature of the non-native polypeptide of the invention is that it is able to fold correctly in the cytoplasm or cytosol of a mammalian cell i.e. assume a tertiary or three-dimensional structure which permits the functionality of the binding moiety(ies) to be retained (i.e. that the binding moieties retain their binding activity towards their ligand). In other words, the binding moiety remains capable of functional binding to its ligand.

The solubility of recombinant proteins is considered a good indicator of their correct folding. Therefore non-native polypeptides of the invention may advantageously be chosen not only on the functionality of binding moieties, stability of conformation and ability to form part of an assembled virion, but also on the basis of solubility within cells in which a non-native polypeptide, or a viral component protein containing or comprising a non-native polypeptide, are expressed. For example, recombinant fiber proteins may be tested for their total expression in eukaryotic (e.g. insect) cells and the proportion recovered in the soluble fraction of the cell lysates determined.

The Inventors have found that phenotypic analysis of fiber-ligand fusion constructs expressed as recombinant proteins in baculovirus-infected insect cells showed that their degree of solubility correlated with the recovery of viable recombinant adenovirus. Therefore, it is preferred that any non-native polypeptide of the invention, or a viral component protein containing or comprising a non-native polypeptide, for example a fiber-ligand fusion construct, is characterised with regard to its solubility and target cell attachment as recombinant protein, prior to the re-insertion of the corresponding gene into the viral, for example adenovirus genome.

Thus the invention also provides a modified virus wherein said non-native polypeptide is selected using a solubility assay of the non-native polypeptide or the viral component protein comprising the non-native polypeptide. The non-native polypeptide is selected such that greater than 25%, preferably greater than 30%, more preferably greater than 50% or even 70%, of the non-native polypeptide or the viral component protein comprising the non-native polypeptide is present in the soluble fraction of cell lysates of cells expressing the non-native polypeptide or viral component protein comprising the non-native polypeptide. A suitable assay is described in the examples herein which may be applied mutatis mutandis to other cell expression systems. Reference herein to a non-native polypeptide or a viral component comprising said non-native polypeptide being soluble in the cellular environment should be interpreted in line with these limits, i.e. when at least 25-30% of the polypeptide is present in the soluble fraction of a cell lysate, the polypeptide can be considered 'soluble'.

Thus, according to a further aspect, the present invention provides a method of determining the suitability of a non-native polypeptide (e.g. a recombinant viral fusion protein) for use in the preparation of a viral vector by determining its solubility in a cell system. More specifically is provided a method of assaying the solubility of a non-native polypeptide or a modified viral protein component of the invention, comprising the steps of i) expressing said non-native polypeptide or a viral component protein comprising said non-native polypeptide in permissive cells; ii) subjecting the cells to lysis to produce a cell lysate; iii) separating the soluble and insoluble fractions of the cell lysate; iv) analysing the soluble and insoluble fractions of the cell lysate for the content of said non-native polypeptide or viral component protein comprising said non-native polypeptide; and, v) comparing the relative content of said non-native polypeptide or viral component protein comprising said non-native polypeptide in the soluble and insoluble fractions to determine the solubility.

A ligand for a binding moiety of the invention may be regarded as the ligand which corresponds to the binding moiety, or in other words, the ligand to which the binding moiety was designed or selected to bind. The ligand is thus capable of binding to the binding moiety. The ligand and its binding moiety may thus be regarded as members of an affinity-binding pair, the ligand being a binding partner for the binding moiety.

The binding moiety thus has a binding specificity for, or is capable of binding specifically to, a desired ligand. By "binding specificity" or "binding specifically" it is meant that the binding moiety is capable of binding to the desired (or "target") ligand in a manner which is distinguished from the binding to non-target molecules or ligands. Thus, the binding moiety either does not bind to non-target molecules or exhibits negligible or substantially-reduced (as compared to the target ligand) e.g. background, binding to non-target molecules. The binding moiety thus specifically recognises the target ligand.

This specificity of binding of the binding moiety thus permits the modified virus to be selectively targeted. In other words, the binding moiety may be designed or selected to enable the modified virus to bind to a desired or "target" cell. A binding moiety may be designed or selected which binds to a ligand expressed by or on a target cell, e.g. on the cell surface.

The ligand may thus be any desired ligand, and advantageously will be a molecule expressed on the surface of a target cell, in which it is desired to achieve expression of the modified virus. The ligand may thus be a cell surface receptor, or a cell-surface antigen. The ligand may conveniently be a protein or polypeptide molecule, but may be of any molecular nature, for example a lipid or carbohydrate.

In this manner, the modified virus may be modified to bind to a desired target cell to which the native (wild-type) virus from which it is derived does not bind, or it may be modified to have a more restricted binding specificity than the wild-type virus, in other words, to bind to only a selected or particular sub-set or type of target cell from among a broader population of target cell types to which the wild-type virus binds. The tropism of the virus is thus altered. Hence, by "altered tropism" it is meant that the modified virus exhibits a target cell binding specificity which is altered, or different, to that of the wild-type virus from which it is derived.

Generally, a non-native polypeptide according to the invention comprises at least one framework moiety and one or more binding moieties and is capable of interacting with other viral components to form a functional and infective virion particle. The ability to form part of a functional virion particle can be facilitated by the presence of one or more sequences within the non-native polypeptide that effect binding to other viral components by the non-native polypeptide itself, or a viral component in which the non-native polypeptide is comprised, in the virion assembly process.

A non-native polypeptide of the invention may replace or be incorporated into any viral component protein which is capable of interacting with a target cell. The modified (e.g. recombinant) viral component possesses a cell binding function either by the nature of a retained native structure of the viral component itself or, by a new structure conferred upon it by the incorporation of the non-native polypeptide and any structures comprised therein. In a preferred aspect of the invention, the non-native polypeptide is introduced or incorporated into or forms a fusion protein with, a viral protein component of the wild type virus, for example, an adenoviral fiber protein, and especially preferably it is incorporated such that the wild-type fiber knob (or at least the cell-binding domain thereof) is removed (i.e. replaced).

However, in an alternative embodiment, a wild-type fiber knob (or cell-binding domain thereof) may be retained, and a further, or additional, cell-binding domain may be added by virtue of the binding moiety(ies) of the non-native polypeptide. It is a feature of the invention that the cell binding functions are altered from those of the wild type virus to be engineered, such that an altered viral tropism is present in the modified virus. Where the wild-type fiber knob (or cell-binding domain thereof) is retained, this altered tropism may be achieved (or facilitated) by modifying the wild-type knob/cell-binding domain thereof to inactivate or block the native or wild-type cell binding function.

As will be discussed further below, it may in certain circumstances be desirable to construct or engineer a modified virus in which control (e.g. temporal control) may be exhibited on the expression of the altered tropism. Thus, in such a modified virus, a native or wild-type tropism may be retained, by retaining the wild-type fiber knob or cell-binding domain thereof, in addition to providing the non-native polypeptide which confers altered tropism. For example, this is desirable for the propagation of a modified virus in conventional cell lines known in the art via the additional presence in the modified virus of a wild type binding function, for example through the controlled expression of a wild type adenoviral fiber gene from an inducible control element (e.g. promoter).

The wild-type tropism may be ablated when desired by controlling (e.g. preventing) expression of the additional wild type viral component genes, or after expression, by removing or inactivating the wild type knob/domain, in such a manner that altered tropism conferred by the non-native polypeptide may be expressed. An "altered tropism" according to the invention thus includes a "potential" altered tropism, i.e. the potential to express an altered tropism. It also includes an altered tropism which is additional to a wild-type tropism.

As mentioned above, the modified virus of the invention is preferably prepared using genetic engineering techniques and in preferred embodiments of the invention, the non-native polypeptide is provided as part of a fusion protein with a viral protein component, preferably as a fusion protein with an adenoviral fiber protein. Such a fusion protein, or more generally, such a modified viral component protein, represents a separate aspect of the present invention. In a preferred embodiment of this aspect of the invention, the modified viral component is a modified adenoviral fiber protein comprising a non-native polypeptide as defined above.

Techniques for preparing such non-native polypeptides and introducing them into viruses or viral components are well known in the art and widely described in the literature. Thus, for example, molecular biology or genetic engineering techniques are readily available, to prepare or construct genetic sequences capable of being expressed as a modified virus, or viral component, according to the present invention. As described further in the Examples below, a nucleic acid molecule or nucleotide sequence encoding a viral component protein, such as the adenoviral fiber protein, may be modified so as to introduce a nucleotide sequence encoding the non-native polypeptide, for example so as to encode a fusion protein comprising all or part of an adenoviral fiber protein and the non-native polypeptide.

Depending upon the viral component protein into which the non-native polypeptide of the invention is incorporated, or which component(s) it replaces, a non-native polypeptide according to the invention can optionally comprise a further element which mimics the native structure or function of the viral component (i.e. is a functional equivalent of the viral component) so as to facilitate the assembly of functional virion particles. In the case of modified adenoviral fibers according to the invention, the functional integrity of the adenoviral fiber with regard to virion assembly, and particularly capsid assembly, is maintained by the presence of external amino acid trimerisation motifs such as the helical amino acid motif derived from the neck region of human lung surfactant protein D (Hoppe et al., FEBS Letters, 344: 191-195 (1994)). This and other trimerisation motifs known in the art can be functionally engineered into the fiber shaft and act as a fiber trimerisation signal to create knob-less fibers. For example, trimerisation motifs suitable for inclusion in modified viruses are described in WO 98/54346 and WO 99/41359. In a preferred embodiment of the invention, the non-native trimerisation motif present in the non-native polypeptide is the neck region peptide from human lung surfactant D.

As described in the Examples below, it may be convenient or necessary for any such additional or external motif or feature to be incorporated into the virus by means of a "linker" sequence. Such construction techniques for incorporation of DNA or amino acid sequences, via attachment to a linker sequence are known in the art and are within the routine skill of a protein/genetic engineer.

A "framework moiety" as defined herein, is a polypeptide (e.g. a protein) structure which retains a functional (e.g. folded) structure (or conformation) in the nuclear and cytosolic cellular environments. Such functional structures are structures which allow a binding moiety attached to, or incorporated within, the framework moiety to retain ligand binding conformation in the absence of the ligand. This facilitates subsequent binding to that ligand, for instance, once the reassembled virion has left the cellular environment.

A framework moiety may thus be regarded as a type of "molecular scaffold" structure, which provides a framework to support or "hold" the binding moiety in an appropriate presentation or conformation to permit binding to its ligand. The framework moiety also provides the intramolecular interactions making a stable conformation in the cytosol possible. The framework moiety may thus be a protein or polypeptide molecule, which assumes a particular conformation or structure, and which tolerates modification in a particular region or regions, for example modification by amino acid sequence addition, insertion, deletion or substitution, or indeed insertion of a polypeptide sequence.

A "binding moiety" as defined herein, is thus a polypeptide structure attached to or comprising part of a framework moiety of the invention and which retains a binding function for a desired (target) ligand after expression of the non-native polypeptide of which it is part in the nucleus and cytosol of a host cell.

The binding moiety may be a contiguous or non-contiguous sequence of amino acids, and may be viewed as providing a binding site for the target ligand. A binding moiety may thus be provided by a region of a protein or polypeptide molecule, for example a surface region, e.g. a number of "surface" amino acid residues.

In certain preferred embodiments of the invention, the framework and binding moieties may be of different origin, e.g. obtained from, or derived, from different sources, (e.g. from different proteins), for example by "grafting" or linking a desired binding moiety onto or to a desired framework. In other preferred embodiments, a binding moiety may be created within a protein "framework" structure, by modifying certain regions or residues of the framework protein, as described further below. In such an embodiment, the framework moiety may be represented by the "constant" or unmodified residues, and the binding moiety by the "variable" or modified residues.

A non-native polypeptide according to the present invention may thus be a combinatorial protein, that is a protein made by randomisation (random mutagenesis) of a particular protein structure, to generate a binding protein with novel, modified or enhanced binding characteristics. Such synthetically constructed "artificial" (in the sense of non-native) proteinaceous affinity binding molecules (i.e. proteins engineered to possess a particular or novel binding function) are known generally in the art.

Such combinatorial proteins can be prepared using various peptides and proteins as starting structures (Nygren and Uhlén, Current Opinion in Structural Biology, 7:463-469, 1997). Such proteins are known in the art, and may typically be prepared by random mutagenesis of a target protein, expression of the full library of these variants, e.g. on the surface of filamentous bacteriophage, followed by selection of a protein exhibiting the desired binding characteristics. This selection may typically involve a binding reaction between the variant protein and a target ligand (binding partner), which conveniently may be immobilised, and may be carried out in vivo or in vitro. The mutagenesis is random in that the resulting amino acid encoded by any particular codon is not generally pre-determined but the positions where mutations are to be introduced are generally identified in advance. The mutagenesis may involve amino acid substitution, deletion, or addition (e.g. insertion).

Preferred combinatorial proteins for use as non-native polypeptides of the invention are proteins known generally in the art as affibodies. The term "affibody" as used herein defines an affinity binding molecule which is derived from a bacterial receptor protein, or binding domain thereof, wherein the binding domain is modified (e.g. by protein/genetic engineering) to modify (e.g. alter or enhance) the binding properties thereof. Advantageously, the affibody is a non-native protein (in the sense of not occurring in nature) and is further preferred to have a novel binding site. Examples and further descriptions of such protein molecules are given in WO 95/19374.

The use of an expression system such as surface display on phage provides a crucial link between genotype and phenotype; there is a self-contained unit which can be selected on the basis of its specific binding interactions and which also carries the nucleic acid encoding for the protein responsible for the observed binding characteristics. This enables expression in useful amounts of the protein selected for its binding characteristics, such expression typically taking place in a transformed bacterial host.

The protein, selected by its ability to bind to a target ligand (e.g. a desired cell surface molecule) may then be used to prepare the modified virus or viral component of the present invention, or more particularly a nucleotide sequence encoding the desired combinatorial protein may be so used.

Techniques for construction of a combinatorial library of protein molecules and subsequent selection to obtain proteinaceous binding molecules having desired binding characteristics are known in the art (Nygren, P. and Uhlén, M. Current Opinion in Structural Biology (1997) 7: 463-469). Generally, a protein molecule, perhaps having intrinsic beneficial properties such as temperature or pH insensitivity, or conformational stability, is used as a "scaffold" or "framework" and a combinatorial library is then constructed via random but targeted amino acid substitutions (or other mutations) of that protein molecule, in order to produce a library of molecules having different binding characteristics. Surface residues are generally targeted for random mutagenesis.

In addition to phage display technology (Smith et al., Meth. Enzym. 217, 228-57, (1993)), other methods for library construction and selection include, for example, ribosomal display (Hanes et al., Proc. Natl., Acad. Sci. USA 94: 4937-4942 (1997)), peptides-on-plasmids (Schatz et al., Methods Enzymol., (1996) 267: 83-109), RNA-protein fusion (Roberts et al., Proc. Natl. Acad. Sci. USA 94: 12297-12302 (1997)) and DNA-protein linkage (STABLE)(Doi et al., FEBS Lett, 457 (2): 227-30, (1999)).

Suitable protein frameworks may simply be linear peptides but preferably the framework will possess a folded three dimensional structure which has the potential for higher affinities and is less susceptible to proteolytic degradation. Although a framework may be designed de novo, naturally existing proteins or domains are usually selected for further engineering. For the avoidance of doubt, it is to be noted that throughout this specification the word "protein" is used to refer to whole protein molecules as well as domains or fragments thereof, polypeptides or peptides.

The choice of protein framework depends on several parameters including an ability to be effectively expressed in a desired host cell (e.g a mammalian cell). The protein should also comprise sufficiently large regions on its surface which are tolerant to substitution (or insertion or deletion etc.) without losing the overall three dimensional structure. If the library is to be produced synthetically, a small overall size is a prerequisite. Where the selected framework protein has a binding function, amino acid residues involved in that interaction may be a target for randomisation. Randomisation may be performed in order to enhance known binding properties or to develop binding molecules with new specificities.

Suitable framework molecules are discussed in Nygren et al. (supra) and include cyclic peptides in a constrained sequence (the number of amino acid residues in such a constrained sequence is not critical and can be 5 or more, e.g. 5 to 10 or more, e.g. 40 or more), immunoglobulin-like scaffolds including Fv or single-chain (scFv) domains, bacterial receptors such as the 58-residue one-domain Staphylococcal protein A (SPA) analogue Z (the "Z Domain" being a derivative of the B domain of SPA), or other domains or analogues of SPA, DNA-binding proteins particularly zinc fingers and protease inhibitors.

Of particular interest is the bacterial receptor domain Z. Nord et al., in Protein Engineering 8(6):601-608 (1995), describe a method of constructing a combinatorial library of protein molecules based on the Z domain, which can be applied to a range of framework molecules. The method described is solid-phase-assisted and based on the stepwise assembly of randomised single-stranded oligonucleotides.

As an alternative to modifying amino acid sequences or residues within a molecule to create a binding moiety, a binding moiety may be introduced to a framework moiety, for example by insertion or addition of a polypeptide constituting or comprising a binding moiety. The binding moiety may thus be attached to a framework moiety. In such a case, a binding moiety may be provided by an affinity binding partner for the desired target ligand.

Preferred binding moieties of the invention may be derived from, but are not limited to, ligands (i.e. binding partners) for cell surface receptors, anti-receptor antibodies (or antibody fragments or derivatives), cell specific peptides, single chain antibodies (ScFv), single domain antibodies, and minimal recognition units of antibodies such as a complementary-determining regions (CDRs) of Fv fragments. A binding moiety may thus be obtained or derived from the antigen-binding site or antigen binding or recognition/region(s) of an antibody, and such an antibody may be natural or synthetic.

Also envisaged within the scope of the invention are binding moieties derived from peptides or polypeptides in any form, including hormones, antibodies, T cell receptors, affibodies and ligands identified from various protein libraries.

As mentioned above, an important feature of the non-native polypeptide is that conformation is maintained in the cytoplasm and nucleus of a mammalian cell, such that the binding function of the binding moiety is retained. As further mentioned above, this is achieved by providing a non-native polypeptide which maintains correct folding in the cytoplasm and nucleus of a mammalian cell. It has been found that such correct folding may be achieved using a non-native polypeptide which does not rely on disulphide bonding for conformation (i.e. which does not contain di-sulphide bonds). As will be discussed in more detail below, a further preferred feature of a non-native polypeptide according to the present invention is the presence of a α-helical structure.

WO 95/19374 describes several framework proteins, which share the beneficial feature of not relying on S—S bonds for their conformation. Such framework proteins are useful as framework moieties according to the invention. These include domains of bacterial receptors such as staphylococcal protein A (ααα type), protein G (IgG binding parts, ββαββ type), protein L (ββαββ type), and protein G (HSA binding parts, αααtype). Framework moieties according to the invention can also be derived from various bacterial receptors, for example, but not limited to those listed in the table 1:

TABLE 1

Examples of G+ bacterial receptors

| Receptor [ligand][a] | Origin |
| --- | --- |
| Fc[IgG] receptor type I | *Staphylococcus aureus* |
| type II | *Staphylococcus pyogenes* [group A] |
| type III | *Streptococcus* group C, G, L |
| type IV | bovine group G streptococci |
| type V | *Streptococcus zooepidemicus* [group C] |
| type VI | *Streptococcus zooepidemicus* S212 |
| Fibronectin receptor + M | *S. aureus*, streptococci |
| protein | *Streptococcus pyogenes* [group A] |
| Plasmin receptor | Streptococci group A |
| Collagen receptor | *S. aureus*, streptococci |
| Fibrinogen receptor | streptococci groups A, C, G |
| Protein L [6 light chains] | *Peptostreptococcus magnus* |
| Protein H [human IgG] | *Streptococcus pyogenes* [group A] |
| Protein B [human IgA, A1] | *Streptococcus agalactiae* [group B] |
| Protein Arp [human IgA] | streptococci group A |
| Serum albumin receptor | streptococci groups A, C, G |

[a]Ligand is indicated when not obvious from receptor name

Framework moieties according to the invention are not restricted to structures from bacterial receptors. Also useful in the invention are other polypeptides comprising α-helical structures, often referred to as α-helical coiled coils, which are known from different sources (Cohen et al., Science 263: 488-489, (1994); Harbury et al., Science 262:1401-1407, (1993)). The coil making up the framework in these peptides consists of repeats of amino acid sequences containing characteristic positioned hydrophobic residues. The structure of α-helical coiled coils is not dependent on intra- or intermolecular disulphide bridges for stability. Examples of α-helical coiled coils are the neck region peptide from human lung surfactant protein D, members or the spectrin superfamily, the leucine zippers and parts of the hemagglutinin in influenza virus.

Particularly preferred as sources of non-native polypeptides according to the present invention are members of the three-helix bundle family (e.g. as exemplified by the Z-domain of staphylococcal protein A).

Thus, in one embodiment, the non-native polypeptide according to the invention comprises a framework moiety which is based on the structure of a domain derived from a bacterial receptor. Preferred structures of the framework moieties of the invention are derived from or based upon the alpha-alpha-alpha (ααα)-three-helix bundle or the beta-beta-alpha-beta-beta (ββαββ) structure classes. Also preferred are structures based upon or derived from the α-helical coiled coil family, particularly a member of any of the 2-, 3- or 4-helical coiled coil families.

In an embodiment of the invention, it is envisaged that the binding moiety is present within one or more of the helical bundles and/or one or more of the loops connecting these bundles.

In a further preferred embodiment of the invention, the framework moiety is based on the structure of a domain derived from staphylococcal protein A, streptococcal protein G or *Peptostreptococcus magnus* protein L.

In a further particularly preferred embodiment of the invention, the framework moiety is a derivative of the immunoglobulin binding Z-domain from staphylococcal protein A (Nord et al., supra).

In such embodiments the binding moiety may be created by combinatorial protein engineering as discussed above. In other embodiments, the domain or protein selected (e.g. the Z-domain) may be used in wild-type form as the non-native polypeptide of the invention.

As mentioned above, through combinatorial protein engineering, e.g. targeted to surface-located residues of the Z-domain, libraries may be constructed from which novel variants (i.e. novel binding molecules) termed Z-domain affibodies, may be selected by binding the desired target ligand (Hansson et al., Immunotechnology 4: 237-52 (1999)).

Preferred Z-domain-based non-native polypeptides may comprise the following amino acid sequences:

VDNKFNKEXXXAXXEIXXLPNLNXXQXXAFIXSLXDDPSQSANLLAEAKKLNDAQAPK;  [SEQ. ID. NO.: 45]

and

VDNKFNKEXXXAXXEIXXXXXXXXXQXXAFIXSLXDXXXXSANLLAEAKKLNDAQAPK,  [SEQ. ID. NO.: 46]

where X is any amino acid.

In the above polypeptides, the conserved (i.e. specified) amino acid residues may be regarded as constituting the framework moiety, and the variable residues X, as together providing the binding moiety.

Furthermore, framework moieties according to the invention need not be dependent on alpha-helices for their stability, provided that the required conformation for ligand binding by the binding moiety is retained after expression of the non-native polypeptide in the nucleus and cytosol of a host cell. Such frameworks for example include frameworks derived from certain antibodies and their derivatives, known in the art, which do not require the presence of disulphide bridges to maintain structure and can therefore be expressed as part of a recombinant viral component in the nucleus or cytosol of a host cell, whilst retaining a functional conformation and functioning as binding moieties for a desired ligand. Other antibody structures within the scope of the invention include antibody structures in which structurally relevant cysteine residues have been replaced with alanine residues, and which retain the binding specificity of the antibody.

Additional framework moieties are also envisaged within the scope of the invention, for example, sequences derived from antibodies (e.g. monoclonal antibodies) and antibodies converted into a single-chain format allowing for the construction of genetic fusions to, or the modification of, viral components. In such a case where an antibody-derived framework moiety is used, then similarly as described above, a binding moiety may be created by protein/genetic engineering techniques (e.g. by modifying certain amino acid residues) or a binding moiety may be introduced (e.g. linked or grafted) to the antibody framework.

Antibody fragments conferring a desired binding activity can be used as binding moieties through the grafting of complementarity determining loops or regions (CDRs) of a an antibody with a desired tropism into a framework moiety capable of productive folding, i.e. capable of retaining the binding specificity(ies) of attached or incorporated binding moieties, in the cytoplasm and subsequent transport into the cell nucleus where the virus assembly takes place. In other words, a binding moiety may be a CDR of an antibody.

Further, according to the invention, certain antibody structure frameworks can be used as framework moieties, for example in conjunction with antibody-based or derived binding moieties e.g. specificity determining loops (CDRs), resulting in the directed construction of antibodies suitable for construction of re-targeted viral components.

An antibody framework may be used as a framework moiety (for example to receive CDR loop(s) as binding moiety (ies)) according to the present invention, provided that it is capable of productive folding in the cytoplasm and subsequent transport into the cell nucleus. Single chain Fv fragments from monoclonal antibodies without disulfide bonds have been produced (Proba et al., J. Mol. Biol., 275: 245-53, (1998)). Such ScFv antibodies provided they meet the functional criterion above, may be used on framework moieties according to the present invention. The binding moiety may be the binding site of the ScFv antibody itself, or it may be further engineered as discussed above.

Intracellular selection of functional antibodies from a polyclonal repertoire has also been achieved (Gargano et al., FEBS Letters 414: 537-40, (1997)). This selection technology may be useful in the identification of antibody fragments suitable for genetic retargeting of adenoviruses, namely suitable for use as framework, and/or binding moieties according to the invention.

Other antibody frameworks which may be used, include those based on camel antibodies which are naturally devoid of light chains, or certain VH regions derived from conventional antibodies.

An example of an antibody framework according to the invention that is capable of productive folding in the cytoplasm, is a particular anti β-galactosidase single chain Fv fragment. This single chain variable chain fragment (VK, linker, VH) reactive with β-galactosidase and capable of being expressed in the cytoplasm has been previously described (Martineau P and Betton J-M: J. Mol. Biol. 292, 921-929 (1999). Thus, the invention also provides a modified virus comprising a framework moiety which comprises a sequence encoding this anti β-galactosidase single chain Fv fragment [SEQ ID. 47.] and functionally equivalent variants thereof.

The invention is not limited to framework moieties based upon antibody and affibody (e.g. receptor) structures, but is extended to include other structures provided these are capable of retaining the binding specificity of attached or incorporated binding moieties when expressed in the cytosol/nucleus of infected cells.

Two or more non-native polypeptides, e.g. having different binding specificities, may be present in a modified virus of the invention, or a non-native polypeptide may incorporate two or more different binding moieties, or indeed two or more different framework/binding moiety constructs.

Accordingly, the invention provides a modified virus which comprises a first non-native polypeptide which binds a target cell and a second non-native polypeptide which binds a production cell or permissive cell.

Non-native polypeptides according to the invention may thus be present in recombinant viral components as comprising bi- or multi functional framework moieties (or framework/binding moiety constructs) constructed through genetic fusion between two or more different framework moieties (framework/binding moiety constructs). Use of such framework moieties (or framework/binding moiety constructs) can, for example confer infectivity of multiple cellular targets to the recombinant virus.

Also provided by the invention is a modified virus in which the non-native polypeptide according to the invention comprises a cleavage site positioned in a location that enables a binding moiety of the non-native polypeptide to be cleaved from the modified virus, for example preceding the binding moiety before the distal end of the fiber relative to the assembled virion. Examples of suitable cleavage sites are sites susceptible to a Factor Xa enzyme or a protease such as the human rhinovirus 3C protease. If cleavage is carried out at the genetic level, for example, within a nucleic acid molecule comprising a part or all of a recombinant adenoviral genome, a cleavage site susceptible to an appropriate restriction enzyme or ribozyme may be used, for example in a particular cell population in which the virus is produced or targetted.

Non-native polypeptides according to the invention are capable of transport through the nuclear membrane. As is known from the art, this is an essential feature of viral components during replication in a host cell where expression of such components takes place in the cytosol, and assembly of such components takes place in the nucleus of the host cell e.g. in adenoviral replication.

The non-native polypeptide of the invention may be viewed as performing a dual role or function, firstly as providing a new binding domain (i.e. conferring altered tropism) and secondly as functioning as a viral component, namely a role as a functional part of a viral component (viral protein e.g. viral capsid protein). The non-native polypeptide may thus contribute to or function as a part of a viral protein. In other words, the non-native polypeptide may play a structural role or function, in the construction or assembly of a virus particle.

Cells comprising, or infected by, the modified virus of the invention also fall within the scope of the invention. Such cells may be of any origin provided that the cell type is capable of harbouring or propagating the virus. Generally, however, such cells will be mammalian cells. Such cells may be transfected with a membrane component (e.g. a membrane protein) that permits infection of the cell by the modified virus and thus permits propagation of a virus which has a non-native tropism in a specific cell line, for example where propagation in conventional cell lines known in the art is prevented by way of the altered tropism of the virus.

Nucleic acid molecules encoding the non-native polypeptides, or modified viral component proteins or modified viruses of the invention are also envisaged. Vectors comprising such nucleic acid molecules, or the nucleotide sequence encoding the non-native polypeptides, or modified viral component proteins or modified virus of the invention, either for propagation of modified virus or further engineering of modified viruses are also included within the scope of the invention.

In a further aspect the invention provides a method for producing a modified virus according to the invention in cell culture. In one embodiment, the method comprises the steps of: genetically modifying a virus to produce a modified (e.g. recombinant) virus containing a non-native polypeptide, which polypeptide comprises one or more framework moieties each containing one or more binding moieties, which polypeptide is capable of being expressed in the cytoplasm and nucleus of a human host cell and there assuming and maintaining a conformation in the absence of a ligand for said binding moieties, which allow said binding moieties to subsequently bind with a said ligand and which polypeptide is capable of transport though the nuclear membrane, wherein said recombinant virus has an altered tropism conferred by said binding moieties; infecting permissive cells with such a virus; culturing said cells to produce the virus (e.g. at a sufficiently high titre), and, harvesting, and optionally, purifying the modified virus produced.

Ad vectors can be made replication competent or incompetent for permissive cells. For tumour therapy, replication competent Ad has the potential advantage that it can replicate and spread within the tumour (Miller et al., Gene Therapy, 3: 557-559). This may theoretically result in an increase of the chosen effector mechanism over that obtainable with replication incompetent vectors. Furthermore, infectious virus may contribute to an anti-tumour effect by cytopathogenic effects in infected cells as well as by evoking an anti-viral immune response which may harm infected cells.

It is desirable that a means of controlling the replication of competent modified virus is available in gene therapy applications.

Other means of controlling the replication of modified adenovirus are within the scope of the present invention For example, the modified virus according to the invention may comprise a gene encoding a viral protein required for viral replication present under the control of an inducible promoter or genetic element. For example, adenovirus pre-terminal protein (pTP), may be present under the regulation of a tetracycline responsive transcription activator (trTA) such that the pTP is only expressed in the presence of doxycycline. Alternatively, the modified virus according to the invention may comprise modifications to the genome such that the virus only replicates in cells which have a defect in the DNA synthesis—apoptosis regulatory pathways.

Conveniently this may be achieved in a modified virus of the invention by introducing the further feature of a cleavage site upstream of the binding moiety, or positioned in any such location that enables the binding moiety to be cleaved from the modified virus, e.g. between the fiber shaft and the binding moiety.

Thus in a further aspect, the invention also provides a method of regulating the replication of a modified virus comprising the steps of: constructing a modified virus such that a cleavage site (e.g. a site susceptible to enzymatic or chemical cleavage) is positioned between a binding moiety required for cell infection and the remainder of the recombinant viral component of which the binding moiety forms part, and, bringing said recombinant virus into contact with a cleavage agent or cleavage means (e.g. an enzyme, chemical or in the case of a photo-labile cleavage site, light) capable of cleaving said binding moiety from said viral component and thereby preventing the recombinant virus from undergoing further infection cycles.

Where the means of cleavage in the method is enzymatic, the cleaving enzyme can be encoded within the genome of the recombinant virus and can be inducible. In a preferred embodiment the cleavage site is cleaved by a Factor Xa enzyme. The use of other proteases known in the art is also envisaged, for example, the human rhinovirus 3C protease, which is available as a fusion protein with GST (Walker et al., Bio/Technology 12:601 (1994)). This protease is active at 4° C., and recognises and cleaves the sequence LEVLFQ//GP.

Non-native polypeptides of the invention can be selected from libraries after screening of such libraries for correct nuclear and cytosolic folding of the peptide and a desired binding function in a manner similar to phage display techniques as known in the art. Such libraries may consist of candidate peptides fused to wild type or modified (e.g. recombinant) viral components according to the invention, for example adenoviral fiber proteins. A fiber fusion library can be expressed on adenovirions and used to select for correct cytosolic and nuclear conformation by observing those candidate fusions which facilitate replication.

Modified virus according to the invention may also be constructed with both wild type and modified viral components present, or encoded in the genome, and if desired, with each component gene under the control of different genetic control elements, for example promoters. Thus, a modified virus according to the invention may comprise a modified viral component (i.e. modified to include or comprise a non-native polypeptide) and an equivalent or corresponding viral component which is unmodified, for example a wild-type fiber, and a modified fiber.

For example, a recombinant adenovirus can be constructed with a wild type fiber and a modified or recombinant fiber (i.e. a modified fiber comprising or incorporating a non-native polypeptide) e.g. a modified fiber derived from a 'fiber-candidate binding peptide' fusion library, which is expressed under control of a different promoter in an E1 deleted adenovirus. For example, the inventors have shown that a recombinant adenovirus fiber gene under the CMV promoter can be cloned into the multiple cloning site of the shuttle vector pAdTrack and that viruses can be produced that express both the WT fiber and the recombinant fiber by homologous recombination using the Ad vector pAdEasy (He T-C, Zhou S, DaCosta L T, Yu J, Kinzler K W and Vogelstein B: A simplified system for generating recombinant adenoviruses. Proc Natl Acad Sci, USA, 95:2509-2514, 1998).

It is also possible to have one or more fiber genes (for example, a wild type gene and a modified gene) present in an adenoviral vector genome under the control of one or more inducible promoters, thus allowing each gene to be switched on or off independently. For example, in a desired Ad construct, the wild type fiber gene, displaced from its normal position and its control by the major late promoter (MLP), can be cloned under control of the hormone inducible MMTV promoter, inducible by dexamethasone. This promoter allows for expression of the wild type fibre in the vector propagating cells. preferably, the modified fiber is cloned in the same Ad vector genome, for example, downstream from a TRE (tetracyclin-responsive element) sequence element that is switched on the in the desired cell line. In cells expressing the tTA protein (a transcriptional activator which binds to TRE), TRE will be activated in the absence of Tc (tetracyclin) or Dox (doxacyclin). Alternatively and more favourably, Ad vector constructs can be propagated in cells which express reverse tTA (rtTA) where TRE, and expression the modified fiber, is activated in the presence of Tc (or Dox).

The recombinant fiber proteins in the library can have the wild-type fiber knob replaced by an external trimerisation motif and one or more members of a peptide library (or other non-native polypeptide). Screening of the recombinant fiber proteins for a desired binding activity can be carried out in a manner analogous to phage display once the recombinant adenovirus has been propagated via expression of the wild type fiber in a culture of propagator cells.

Accordingly, modified virus with an altered tropism will require cells which it is capable of infecting in order to allows its propagation. Thus the invention also provides permissive cells for virus according to the invention which are capable of being cultured to propagate the virus. A replication incompetent virus (which generally comprises a deletion in its genome rendering it incompetent) needs special producer or propagator cells which are able to supply the genetic information that is deleted or missing from the virus, in order to replicate. Such cells or cell lines are known in the art. A modified virus with an altered tropism may be unable to infect such cells as are known in the art. Accordingly the invention includes the modification of such a propagator cell to include a binding partner (ligand) for the binding moieties of the modified virus (e.g. such that the cells express such a ligand on their surface).

Accordingly the invention provides a cell, preferably an in vitro or ex-vivo eukaryotic cell, containing a modified virus or viral component of the invention.

It is also envisaged that modified virus with an altered tropism might propagated in the same cells as the wild type virus by means of positioning the new tropism-altering binding moieties within a viral component which also comprises a wild type binding moiety (i.e. knob), with a cleavable site (e.g. for an enzyme such as Factor Xa or human rhinovirus 3C protease) between such moieties. After propagation in conventional cells via action of the wild type binding moiety, the viral component may be cleaved to remove the wild type binding moiety (e.g. the wild-type knob) and to reveal the new binding moiety and to confer the new tropism. It is also envisaged that the revealed binding moiety can be specific for a ligand which itself possesses a cell binding capability. For example, the binding moiety can be specific for the Fc region of an antibody, thereby permitting the use of an antibody which is cell specific for a desired cell type. Removal of the wild type binding moiety by cleavage and exposure of the virus to a cell specific antibody, allows the antibody to be adsorbed to the virus and thus targets the virus to the cells specified by the antibody.

Non-native polypeptides according to the invention preferably confer an altered tropism to the recombinant virus in comparison with the tropism of the virus to which the non-native polypeptide has been introduced. Such altered tropisms allow recombinant viruses of the invention to be used in treatment of disease in human or animal subjects, either by in vivo treatment of, or ex vivo treatment of cells of, the subject requiring treatment.

The tropism of the modified virus of the invention may be altered such that the virus, via one or more binding moieties targets particular cells. Thus the invention also provides a modified virus wherein a non-native polypeptide comprises a binding moiety capable of binding to a cell specific ligand which may optionally be Prostate Specific Membrane Antigen, EGF receptor, Her-2/Neu, VEGF receptor, CD22, gp120, MHC/peptide complexes or membrane structures or surface molecules expressed or present on proliferating cells, tumor cells or virus infected cells There are many ways in which modified virus exhibiting an altered tropism according to the invention can be used in gene therapy applications. In the case of tumour diseases, the following options exist:

I. Use of vectors to introduce transgenes into tumours, such as:
   - antisense oncogenes
   - suicide genes
   - genes for immune modulatory substances or tumour antigens
   - genes for anti-angiogenic factors Examples of transgenes suitable for inclusion in the modified virus of the invention are antisense oncogenes, suicide genes, genes for immune modulatory substances, genes for tumour antigens, genes for anti-angiogenic factors, cytokines, genes for vascular endothelial growth inhibitors, genes for fusogenic membrane glycoproteins, cytotoxic genes, a gene encoding an enzyme which converts a pro-drug to cytotoxic substance, a gene for cytosine deaminase, a gene for uracil phosphoribosyl transferase. In a preferred embodiment of the invention the modifed virus comprises transgenes encoding cytosine deaminase and uracil phosphoribosyl transferase either as separate genes or, more preferably, together as a bifunctional fusion gene In methods of treatment employing viruses of the invention with the transgenes cytosine deaminase and uracil phosphoribosyl transferase, preferably the virus is present or is co-administrated with one or more inhibitors of dihydropyrimidine dehydrogenase. This has the effect of increasing the toxic effect of the products formed by these transgenes from the pro-drug, 5-Fluorocytosine.

Also provided by the invention is a modified virus of comprising one or more viral components or transgenes present under the control of one or more inducible promoters or genetic elements, which are for example tissue specific or which respond to the presence of an exogenous expression modulating substance.

II. Use of infectious virus. This has the added value over the use of non replicating vectors in that virus can spread from cell to cell within a tumour, thereby multiplying the initial hit, or effect, on the tumour. Tumour cell destruction can occur not only by the cell-destroying mechanism engineered into the vector but also by the cell destruction which is associated with the virus infection per se and by the attack of the body's immune response on the virus infected cells. This principle has already been tested in man through the direct intra-tumoural injection of an adenovirus which has been made gene manipulated to replicate only in p53 mutant tumour cells. The experience from these limited trials on large "head-and-neck" tumours are partially encouraging with a total regress of 2/11 treated tumours which are otherwise resistant to any form of known treatment (Shen Y: Personal communication).

Also provided by the invention is a modified virus wherein the gene encoding adenovirus death protein (ADP) is placed under the control of a promoter permitting over-expression of the protein, such that the lytic capacity of said modified virus is increased.

Thus, for gene therapy the modified virus may further be modified, according to standard techniques, principles and proposals widely described in the literature, to incorporate or comprise a desired therapeutic gene or therapeutic nucleic acid molecule. "Therapeutic" is used broadly herein to include both therapy (in the sense of curative or palliative therapy of a pre-existing or diagnosed condition) and prophylaxis. The gene may encode a desired therapeutic product (e.g. a therapeutic polypeptide or antisense molecule).

In a further aspect of the invention, the modified virus may include a site (e.g. a restriction site) for insertion of a desired therapeutic gene/nucleic acid molecule.

One disadvantage of using a wild type virus in gene therapy, even after modification according to the invention, is that the human or animal subjects to be treated with the virus may possess pre-formed antibodies to components of the wild type virus still present or only partially modified in the modified virus. For example human adenovirus serotype 5 hexon protein is often targetted by pre-formed antibodies. Whilst modification of a single viral component, for example the component containing the non-native polypeptide according to the invention, may be sufficient to reduce the initial immune response to the modified virus via pre-formed antibodies, it may be preferable to modify a further component of the virus to further reduce the immune response of the host.

Thus the invention further provides a modified virus according to the invention which further comprises a viral component which is replaced with an equivalent component or is modified such that binding of said virus by antibodies pre-formed to the wild type virus is reduced. For example, an adenovirus of serotype Ad5 may comprise a hexon protein which is swapped for a hexon protein of a different serotype against which pre-formed antibodies are present at a reduced level compared to serotype Ad5, for example the different serotype may be Ad37. Alternatively, a modified adenovirus may comprise epitope sequences of the hexon protein to which pre-formed antibodies bind which are modified to produce a recombinant hexon lacking immunogenic epitopes.

Furthermore, the modified adenovirus may comprise a hexon protein which further comprises a peptide capable of binding a protein, for example, a non-immune system protein such as human serum albumen, sufficiently to cover the immunogenic epitopes of the hexon which are bound by pre-formed antibodies.

Also provided by the invention is a modified virus according to the invention for use in therapy or in the preparation of a medicament for the treatment of tumour cells or proliferating cells.

Additionally provided by the invention is a pharmaceutical composition comprising a modified virus of the invention and a pharmaceutically acceptable carrier or excipient.

The invention will now be described in more detail with reference to the following non-limiting Examples, in which:

FIG. 1 shows a schematic description of the sequence of construction of different recombinant fibers.
A. The NRP sequence is supplied with flanking Sph1 and Xho1 sites using PCR and ligated into WT fiber which has been supplied with flanking EcoR1 and Xho1 sites. The resulting fiber is called A1 and contains the fiber tail, first shaft repeat and the NRP motif.
B. EGF is joined to the fiber A1 by SOE. In the process an amino acid linker and a Cla1 restriction site is added between the NRP and EGF sequences. The resulting fiber is named A1 EGF. In this fiber, EGF can be substituted for new ligands by ligation using the Cla1 and Xho1 sites.
C. The NRP-Linker-EGF part of fiber A1 EGF is Subjected to PCR. In the process an upstream Nhe1 site is introduced into the sequence in frame with the WT fiber sequence. After AT cloning, the sequence is ligated into WT fiber using Nhe1 and Xho1 to create fiber A7 EGF. A7 differs from A1 in that A7 contains the first seven shaft repeats of the Ad5 fiber. In the A7 EGF construct, EGF can be substituted for new ligands by ligation using the Cla1 and Xho1 sites.

Figure 2:
FIG. 2 shows a schematic representation of the different recombinant fibers used in the present application.
Figure 2:
Figure 2:
Figure 2:
Figure 2:
Figure 2:
Figure 2:
Figure 2:
Figure 2:

FIG. 2 shows a schematic representation of the different recombinant fibers used in the present application.
A. The Ad5 wild type fiber.
B. The fiber A7 EGF described above.
C. The fiber A7 scFv C242 obtained by substituting EGF in fiber A7 EGF for the scFv fragment by ligation as mentioned above.
D. The fiber A7 scFv G250 obtained by substituting EGF in fiber A7 EGF for the scFv fragment by ligation as mentioned above.
E. The fiber A7 Affi IgG where EGF in fiber A7 EGF has been substituted for an IgG binding affibody as mentioned above.
F. The fiber A7 Affi IgA where EGF in fiber A7 EGF has been substituted for an IgA binding affibody as mentioned above.
G. G. The fiber A7 Affi IgG/Affi IgA where EGF in fiber A7 EGF has been substituted for an IgG binding affibody linked to an IgA binding affibody as mentioned above.
H. The fibre A7 ZIgG/ZIgG where EGF in fibre A7 EGF has been substituted for an IgG binding affibody linked to another IgG binding affibody as mentioned above.
I. The fibre A7 ZIgG Xa Knob where EGF in fibre A7 EGF has been substituted for an IgG binding affibody linked to a cleavable wild type fibre knob.

Figure 3:
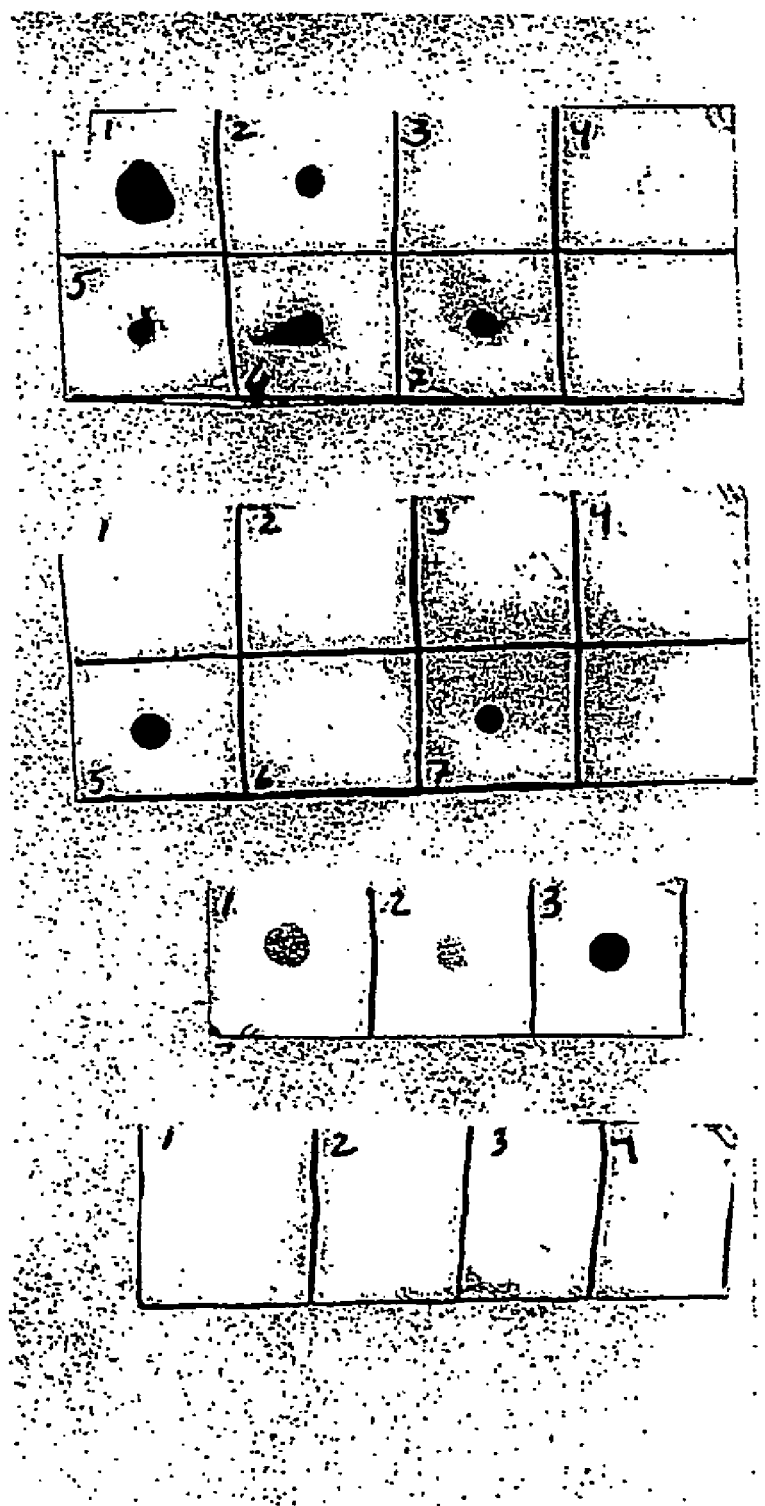
FIG. 3 shows the binding of ZIgG affibody when incorporated into fibers expressed in virions.

FIG. 3 shows the binding of ZIgG affibody when incorporated into fibers expressed on virions.
Panel A. After binding of virus or protein to the membrane, it was incubated with Fc3(1) followed by HRP conjugated anti human IgG and developed. 1=the virus A7 ZIgG Xa Knob; 2=the same virus after cleavage with Xa; 3=WT virus; 4=virus with two fibers e.g. WT and A7 ZIgG; 5=Fc3(1); 6=Protein A; 7=Protein AG.
Panel B. After binding of virus or protein to the membrane, it was incubated with Fc3 followed by HRP conjugated anti human IgG and developed. 1=the virus A7 ZIgG Xa Knob; 2=the same virus after cleavage with Xa; 3=WT virus; 4=virus with two fibers e.g. WT and A7 ZIgG; 5=Fc3; 6=Protein A; 7=Protein AG.
Panel C. Control to show presence of virus on membrane. 1=the virus A7 ZIgG Xa Knob; 2=the same virus after cleavage with Xa; 3=WT virus. After binding of virus the membrane was incubated with HRP conjugated anti Ad5 hexon and developed.
Panel D. Treated as membranes in panel A and B but the incubation with Fc was omitted. 1=the virus A7 ZIgG Xa Knob; 2=WT virus; 3=protein A; 4=protein AG.

Explanatory note: Fc3(1) is known to bind ZIgG and protein A. Fc3 is known to bind protein G (AG) only.

Figure 4:
FIG. 4 shows a schematic representation of the fibers described in Example 11.
Figure 4:
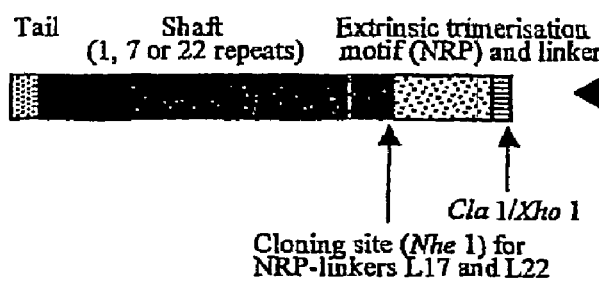
Figure 4:
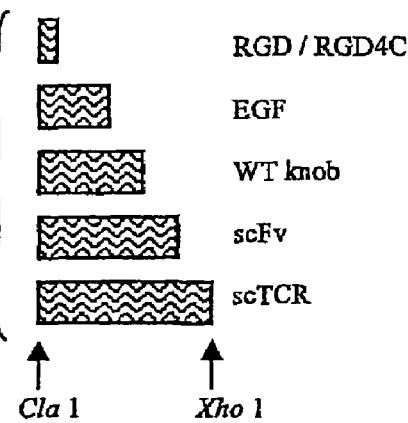

FIG. 4 shows a schematic representation of the fibers described in Example 11. The NRP-linkers were inserted in the Nhe1 site upstream of NRP.

Figure 5:
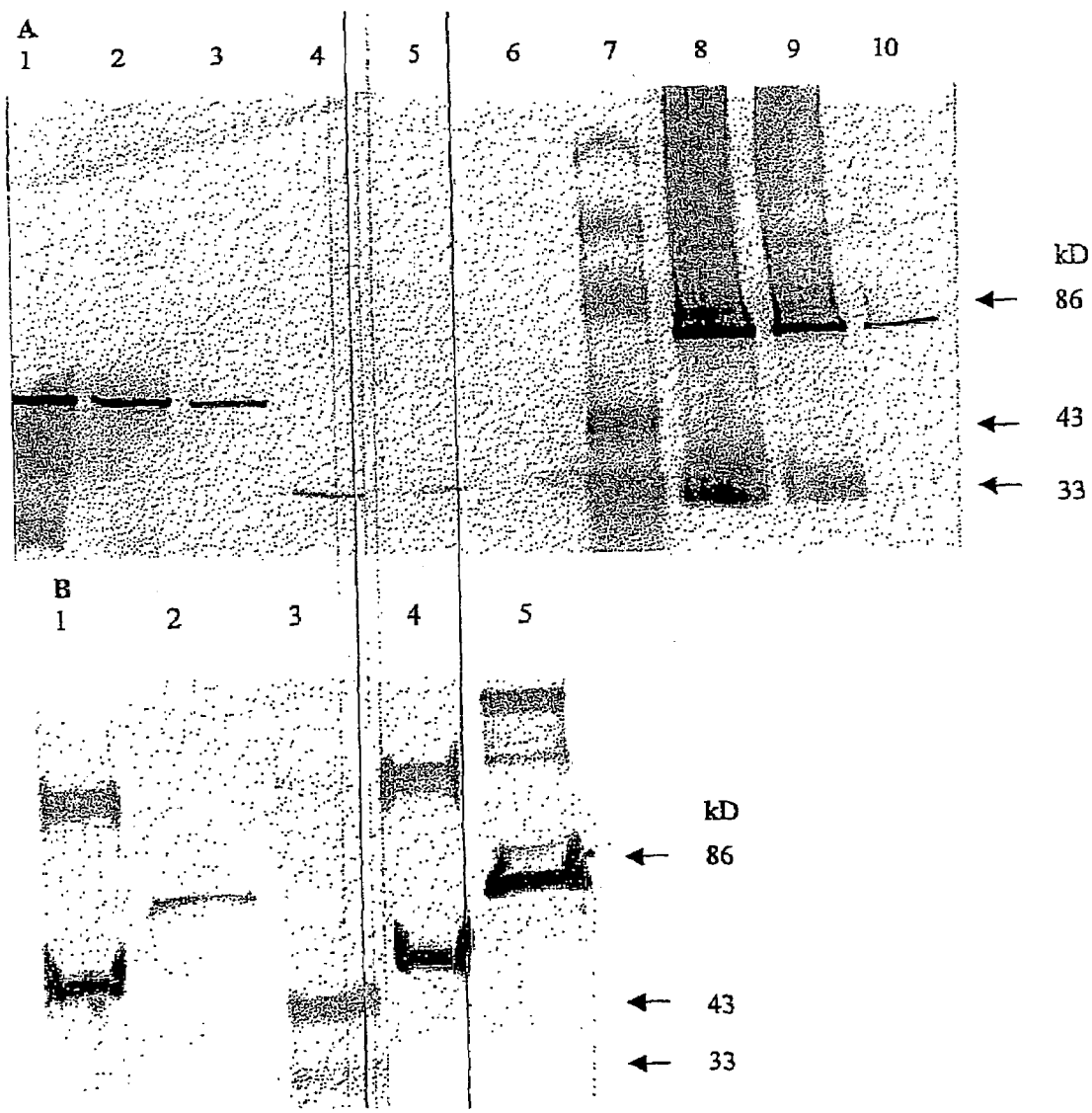
FIG. 5 shows gel photos demonstrating expression and solubility of recombinant fibers in Sf9 cells.

FIG. 5 shows gel photos demonstrating expression and solubility of recombinant fibers in Sf9 cells. (A), whole cell lysate; (B), soluble fraction. Baculovirus-infected cells were harvested at 48 h after infection, lysed in isotonic buffer, and cell lysates divided in two aliquots. One aliquot was centrifuged at 10,000×g for 10 min and supernatant was kept (panel B), whereas the other was analysed as whole cell lysate (panel A). Both aliquots were heat-denatured in SDS-sample buffer, analysed by conventional SDS-PAGE, and blotted. Blots were reacted with 4D2.5 mAb (specific for the fiber tail) and radiolabeled secondary antibody. Immunoblots were quantitated by autoradiogram scanning. Quantitative data, expressed as the percentage of soluble versus total fiber content, are shown in Table 7.

EXAMPLES

General Procedures and Starting Materials

Recombinant adenovirus fibers were constructed using methodologies based on ligation and PCR (Clackson et al., General application of PCR to gene cloning and manipulation, in PCR, A Practical Approach, Eds McPherson M J, Quirke P and Taylor G R, IRL Press, Oxford, page 187, (1992)), i.e. PCR-ligation-PCR (Alvaro et al., BioTechniques 18: 746-750 (1995)) and splicing by overlap extension (SOE) (Horton et al., Recombination and mutagenesis of DNA sequences using PCR, in McPherson M J (ed), Directed Mutagenesis, IRL Press 1991, p 217.). Gene products generated by PCR were generally cloned into the vector pCRII (Invitrogen Corp.) using so called TA cloning (Clark J. M., Nuc. Acids Res. 16: 9677-86, (1988)). Subclonings were performed according to standard methods (Sambrook et al., Molecular cloning. A laboratory manual. Second Edition. Cold Spring Harbor Laboratory Press, (1989)) in the vector pGEX-4T-3 (Amersham Pharmacia Biotech). Genes encoding recombinant fibers were sequenced using the Perkin Elmer ABI Prism sequencing equipment and were expressed in mammalian cells (SV40 transformed African Green monkey kidney cells, COS7, obtained from American Type Culture Collection, VA, USA) using vectors described below, and in insect cells (Sf9 cells from *S. frugiperda* obtained from American Type Culture Collection, VA, USA) using Baculovirus expression (Kitts et al., Biotechniques 14(5): 810-7, (1993)) (virus and vector from Clontech, Palo Alto, Calif., USA) and stained with monoclonal antibodies specific for fiber tail, trimeric fiber and the new cell binding ligand. The following parameters were evaluated by immunostaining:

i) nuclear transportation
ii) functional expression of the new cell binding ligand
iii) ability to form trimers Recombinant fibers were rescued into the Ad genome by a recently developed procedure (as described in Example 7 herein). The plasmid pTG3602 (Chartier et al., J. Virol., 70: 4805-4810, (1996)) containing the entire Ad5 genome as a Pac1-Pac1 fragment was used as starting material. The approximately 9 kb fragment of the genome between Spe1 and Pac1 and containing the wild type fiber gene was cloned separately in pBluescript. From this fragment an approximately 3 kb fragment between Sac1 and Kpn1 was further subcloned. A deletion of the native fiber gene with the exception of the N-terminal nucleotides upstream of the Nde1 site of the fiber was created in the 3 kb fragment and an Xho1 site introduced in its stead allowing for ligation of recombinant fibers into the fiber-deleted 3 kb fragment (the 3 kb fiber shuttle) between Nde1 and Xho1.

The 3 kb fiber shuttle with recombinant fiber was re-introduced into the 9 kb fragment cut with Nhe1 using homologous recombination in *E.coli* (Chartier et al., Supra). The resulting recombinant 9 kb fragment was finally excised from the vector with Spe1 and Pac1 and joined to the isolated 27 kb fragment by Cosmid cloning.

The presence of an insert of the expected properties was verified in all cosmid clones by PCR. Cosmid clones were also restricted with Hind III and the presence of restriction fragments of the expected size verified on gels.

Recombinant Ad genomes were isolated after restriction with Pac 1 and used to transfect suitable cells. The occurrence of plaques was determined by microscopic inspection of the transfected cell cultures.

List of oligonucleotide primer names for the primers used (all given as 5'-3' sequence):

```
[SEQ. ID. NO.: 20] Name 149:  TTCCTCGAGTTATTCTTGGGCAATGTATGA

[SEQ. ID. NO.: 21] Name 175:  GGGGAATTCGATGAAGCGCGCAAGACCGTCTGAA

[SEQ. ID. NO.: 22] Name: 196: GCTCGAGTTATCCGTTTGGAAACAACTCTAC

[SEQ. ID. NO.: 23] Name: 228: CTCGAGTCATCTCAATTCCCACCACTT

[SEQ. ID. NO.: 24] Name: 238: TGGCATGCCTGACGTAGCAAGCTTACGA

[SEQ. ID. NO.: 25] Name: 253: GGGGAATTCATCGATGCAGGTCCAGTTGGTGCAGTCT

[SEQ. ID. NO.: 26] Name: 265: CAGGTCCAGTTGGTGCAGTCT

[SEQ. ID. NO.: 27] Name: 269: GGGGGCCTGGGCGTCGTTCAGCTTCTTGGCTCCGTTTGGAAACAACTCTAC

[SEQ. ID. NO.: 28] Name: 270: CTGAACGACGCCCAGGCCCCCAAGAGCGACCCATCGATCATGAACTCCGACTCCGAATGT

[SEQ. ID. NO.: 29] Name: 273: CCCCTGGAGTTAAATTTTCTTGTCCACCTTGGTGCT

[SEQ. ID. NO.: 30] Name: 274: GGGGAATTCATCGATGGACTACAAAGATATTGTGATGACGCAGGCT

[SEQ. ID. NO.: 31] Name: 275: CTACCTCGAGTTAACACTCATTCCTGTTGAAGC

[SEQ. ID. NO.: 32] Name: 326: GGGGCTAGCCCCTGACGTAGCAAGCTTACGA

[SEQ. ID. NO.: 33] Name: 403: GGG CTC GAG TTA CTC GAT GGG GGC TGG GAG GGC

[SEQ. ID. NO.: 34] Name: 414: GGCCCCCGAGGCCTCGAGTGAGGAGACGGTGACCGTGGT

[SEQ. ID. NO.: 35] Name: 416: GGCCCAGCCCACGAATTCATCGATGGATATTGTGATGACGCAGGCT

[SEQ. ID. NO.: 36] Name: 418: AGA CTG CAC CAA CTG GAC CTG (SNN)$_{18}$CCGTTTCAGCTCCAGCTTGGT
                                 (S is dA, dG or dC and N is dA, dG, dC or dT)

[SEQ. ID. NO.: 37] Name: 473: GGC AAT TCC ATC GAT CGC CAC CAT GGA CAT TGT GAT GAC CCA GTC T

[SEQ. ID. NO.: 38] Name: 474: CCC CTC GAG TTA ACA CTC ATT CCT GTT GAA GCT

[SEQ. ID. NO.: 39] Name: 476: ACC ACG GTC ACC GTC TCC TCA GCT GAT GCT GCA CCA ACT GTA

[SEQ. ID. NO.: 40] Name: 478: TGA GGA GAC GGT GAC CGT GGT

[SEQ. ID. NO.: 41] Name: 503: GGGCCATCGATCGTAGACAACAAATTCAACAAA

[SEQ. ID. NO.: 42] Name: 504: GGGCTCGAGTTATTTCGGCGCCTGAGCATCATT

[SEQ. ID. NO.: 43] Name: 550: TCGGTTTGGAAACAACTCTACCTTTTTTTTCGGCGCCTGAGCATCATT

[SEQ. ID. NO.: 44] Name: 551: AAAAAGGTAGAGTTGTTTCCAAACGGAGTAGACAACAAATTCAACAAA
```

Example 1

Genetic Insertion of a Trimerisation Motif (the Neck Region Peptide from Human Lung Surfactant D) into Adenovirus Fibers The gene encoding Ad 5 WT fiber was obtained from a preparation of Ad5 virus by PCR using an upstream primer (Primer 175) identical to the first six coding triplets of the fiber plus an EcoR1 site and a downstream primer (Primer 149) annealing to the six terminal coding triplets of the fiber plus an Xho1 site. The fiber thus obtained [SEQ. ID. NO.: 1] was cloned into the vector pBluescript using these restriction sites and can be further sub-cloned into other vectors using the same restriction enzymes.

Fiber peptides were made where the knob was replaced with an external trimerisation motif (see below). The purpose behind the introduction of an external trimerisation motif is two-fold: a) to remove the knob containing the native trimerisation signal but also the cell binding part of the fiber, and b) simultaneously to supply the necessary trimerisation signal. In this case one particular amino acid motif have been used, i.e. the 36 aa "Neck Region Peptide"=NRP [SEQ. ID. NO.: 2] from human "Lung Surfactant Protein D" (Hoppe et al., Supra). It should be noted that the sequence used is slightly longer than the actual trimerisation part of NRP in that the eight amino acids (KKVELFPN) following the trimerisation signal in human lung surfactant protein D has been retained in all constructs containing the NRP sequence. The sequence KKVELFPN functions as an efficient linker between the trimerisation signal and the C-terminal carbohydrate domain of the human lung surfactant D and is considered to have the same important function in the recombinant fibers described herein. The DNA sequence coding for the trimerisation motif was synthesized, cloned and verified by sequencing.

In order to introduce the NRP motif into the adenovirus fiber, the NRP sequence was subjected to PCR (Clackson et al., Supra) with the upstream primer 238 containing Sph1 N-terminally of the NRP coding sequence and the downstream reverse primer 196 containing Xho1 C-terminally of the coding sequence. After cutting with Sph1 and Xho1 the NRP sequence was ligated into the WT fiber gene cut with the same enzyme. The resulting recombinant fiber A1 [SEQ. ID. NO.: 3] contains the fiber tail and the first shaft repeat followed by the NRP trimerisation motif. For a schematic representation of the constructions and construction pathways see FIGS. 1 and 2.

To replace the cell binding function of the knob a new cell binding ligand was subsequently introduced into the fiber in addition to the external trimerisation amino acid motif (see below).

Example 2

Assembly of Gene Construct Encoding Recombinant Adenovirus Fibers with Epidermal Growth Factor (EGF) and the External Trimerisation Motif from Human Lung Surfactant D For a schematic representation of the constructions and construction pathways see FIGS. 1 and 2.

The DNA sequence for human EGF [SEQ. ID. NO.: 4] was synthesized, cloned and sequenced in the project. This sequence was then joined to the A1 fiber mentioned above by splicing by overlap extension. In this case the EGF gene was subjected to PCR with an upstream primer (270) (identical to the first seven coding triplets) and containing an overhang with the sequence for an amino acid linker [SEQ. ID. NO.: 5] derived from Staphylococcal protein A and a Cla1 restriction site, and a downstream primer (228) (complementary to the seven terminal triplets of the + strand and containing an Xho1 site). The A1 fiber gene was subjected to PCR with an upstream primer identical to the first six coding triplets of the gene and an EcoR1 site (175) and a downstream primer (269) complementary to the seven terminal coding triplets of the + strand and an overhang complementary to the overhang in Back primer for the EGF sequence. The two PCR products where then joined by PCR under standard SOE conditions (Horton et al., Supra) to produce fiber A1 EGF [SEQ. ID. NO.: 6].

In order to construct a fiber with the first seven shaft repeats, the NRP trimerisation signal, the Staphylococcal linker and EGF, the fiber A1 EGF was subjected to PCR with an upstream primer (326) identical to the first seven 5' triplets of the NRP sequence plus an upstream Nhe1 site and a downstream primer (228) complementary to the seven terminal triplets of the A1 plus strand. After cloning the PCR product was restricted with Nhe1 and Xho1 and ligated into WT Fiber restricted with the same enzymes to obtain Fiber A7 EGF [SEQ. ID. NO.: 7] which is similar to A1 EGF but differs in that it contains the first seven shaft repeats of the Ad5 Fiber.

Example 3

Assembly of Gene Construct Encoding Recombinant Adenovirus Fibers with Single-chain Antibodies and the External Trimerisation Motif from Human Lung Surfactant D Two monoclonal antibody single chain fragments were used to construct recombinant adenovirus fibers. The first is a single chain fragment (scFv) of the monoclonal antibody G250, which with high selectivity has been shown to react with a protein antigen on human renal carcinoma cells (Oosterwijk et al., Int. J. Cancer 38: 489-94, (1986)). The second is a single chain fragment of the monoclonal antibody C242 which reacts with i.a. colorectal and pancreatic carcinomas (Johansson C., Thesis, University of Gteburg, (1991)).

G250 Constructs

The single chain fragment (Variable kappa chain or VK, linker, variable heavy chain or VH, joining sequence and constant heavy domain 2 or CH2) of the antibody G250 was constructed as previously described (Weijtens et al., J. Immunol., 152(2): 836-43, (1996)). This G250 construct is [SEQ. ID. NO.: 8]. To permit cloning into the aforementioned A1 and A7 fiber constructs, the single chain fragment was supplied with an upstream Cla1 site and a downstream Xho1 site by PCR using primers 416 and 403.

C242 Constructs

The single chain fragment of the antibody C242 (Variable kappa, Linker, variable heavy and constant kappa or CK) [SEQ. ID. NO.: 9] was constructed as follows by SOE using cDNA from the antibody producing hybridoma as original templates. VKCK was amplified using primers 274 and 275, VHCH1 was amplified using primers 253 and 273. An scFv (single chain variable fragment) (VK LinkLib VH) was constructed by SOE as follows. VK and VH were amplified separately using primers 416/418 and 265/414 respectively with the above mentioned VKCK and VHCH1 as templates and joined together by SOE using primers 414 and 416. In the construct VK LinkLib VH, the linker between VK and VH is a randomized 18 amino acid sequence as described previously (Tang et al., J. Biol. Chem., 271: 15682-86, (1996)). The nucleotide sequence for this linker is present in primer 418. The construct VK LinkLib VH was cloned into the vector pAK100 (Krebber et al., J. Immunological Methods 201: 35-55, (1997)). Phage display and selection of antigen binders by panning was performed using methods described earlier (Krebber et al., Supra). In the present experiments, the CanAg antigen, reacting with antibody C242, was adsorbed onto biotinylated antibody C241 (which binds another epitope on the antigen than C242) bound to streptavidin coated tubes (CanAg Diagnostics Ltd, Gteburg, Sweden). Several binders were isolated and shown to contain different linkers. A particular VK Linker VH construct shown by sequencing to contain the linker PPDFVPPAASFPDHSPRG (one letter amino acid code) was selected for further work based on antigen binding ability. CK was linked to this construct by SOE to obtain the format C242 VK Link VHCK. In this SOE the VK LinkLib VH was amplified using primers 416 and 478 and the CK amplified with primers 476 and 474. The amplified products were then joined by SOE using primers 416 and 474.

In the PCR reactions mentioned above the gene sequences for the single chain fragments were supplied with an upstream Cla1 site (present in primers 416 and 473) and a downstream Xho1 (present in primers 403 and 474) to allow for ligation into the A1 and A7 fiber constructs mentioned earlier (for a schematic representation of the constructions and construction pathways see FIGS. 1 and 2) to construct the fibers A1 G250, A7 G250, A1 C242 and A7 C242 (FIG. 1 and [SEQ I.D. NOS. 10-13]).

Example 4

Assembly of Gene Constructs Encoding Recombinant Adenovirus Fibers with Affibodies and the External Trimerisation Motif from Human Lung Surfactant D To investigate if mono and divalent antigen binding structures based on the structure of single staphylococcal protein A domains could be functionally expressed when incorporated into recombinant Adenovirus fiber, gene constructs for mammalian and insect cell expression were made. Assembly of gene constructs encoding recombinant adenovirus fibers containing the IgG binding Z domain (ZIgG) derived from staphylococcal protein A (Nilsson B., Prot. Eng. 1:, 107-13, (1987)) [SEQ. ID. NO.: 14] or a Z domain-derived IgA-specific affibody (ZIgA) selected using phage display (Gunneriusson E. et al., App. Env. Micro., 65: 4134-40, (1999)) [SEQ. ID. NO.: 15] was accomplished as follows.

The genes encoding the respective affinity moieties were amplified by PCR using primers 503 and 504 on the following plasmid templates; pEZZmp18 (Tang et al., Supra) for the Z domain construct and pKN1-dZIgA (Clackson et al., Supra) for the ZIgA construct.

In the PCR amplification, the genes for the two different affinity ligands were supplied with an upstream Cla I site and a downstream Xho I site in the appropriate reading frame for subsequent ligation into the above described fiber gene A7 EGF resulting in constructs encoding the recombinant fiber A7 ZIgG [SEQ. ID. NO.: 16] and A7 ZIgA [SEQ. ID. NO.: 17], respectively, which were adapted for later being rescued into the Ad genome (see below) for the production of recombinant viruses carrying the new binding specificities. Furthermore, the fiber A1 ZIgG was constructed by ligation of the modified ZIgG into the aforementioned fiber A1 EGF (see also FIG. 1).

In addition, a third gene construct was assembled encoding a fiber containing both of the above mentioned affinity domains. This construct encodes a fiber containing the fiber tail, the first seven shaft repeats, the NRP sequence, the staphylococcal protein A linker, the IgG binding Z domain, the eight amino acid linker from NRP (KKVELFPN) followed by the IgA binding affibody. To construct this fiber the two different affinity domains were first genetically joined together by SOE using primers 550 and 551 with overhangs complementary to the nucleotide sequence encoding the linker sequence KKVELFPN. In the PCR process an upstream ClaI site and a downstream XhoI site were introduced by the primers allowing for ligation into the vector pGEX-4T-3 containing the Fiber A7 EGF gene construct to obtain Fiber A7 ZIgG/ZIgA [SEQ. ID. NO.: 18].

A further gene construct was also assembled to encode a fiber containing two linked ZIgG domains. This gene codes for the fiber A7 ZIgG/ZIgG [SEQ. ID. NO.: 19] and was assembled exactly as described for A7 ZIgG/ZIgA with the exception that the gene for ZIgG was used instead of ZIgA in the PCR reaction.

For a schematic representation of the constructions and construction pathways see FIGS. 1 and 2.

Example 5

Binding Studies

The genes encoding recombinant fibers were cloned into the vectors pcDNA (which targets proteins for expression in the cytosol) and pSecTag (which targets proteins for expression as secreted products), both from Invitrogen BV, Groningen, The Netherlands, and transfected into COS7 cells using Lipofectamin (Life Technologies Inc, Gaithersburg, Md., USA) as described by the manufacturers.

Expression and cellular localization of recombinant fibers were evaluated by immunostaining using the following primary reagents:

Mouse monoclonal antibody 4D2.5 (anti-Ad5 fiber) (kindly provided by Dr Geoffrey Engler, University of Birmingham, Ala., USA) (Shin Hong et al., Virology 185: 758-767, (1991)).

Mouse monoclonal antibody 2A6.36 (anti-trimerised Ad5 fiber) (kindly provided by Dr Geoffrey Engler, University of Birmingham, Ala., USA) (Shin Hong et al., Supra).

Mouse monoclonal antibody against Epidermal Growth Factor (EGF)=a-EGF (Cambio, Cambridge, UK, Cat no CA 954).

Biotinylated mouse monoclonal anti idiotypic antibody directed against monoclonal antibody C242=a-Id C242 (Lindholm et al., unpublished results).

Biotinylated mouse monoclonal anti idiotypic antibody directed against monoclonal antibody G250=a-Id C250 (Kindly supplied by Reinder Bolhuis, Daniel Den Hoed Cancer Center, Rotterdam, The Netherlands).

Human polyclonal IgG and IgA for evaluation of Affibody activity=HIgG (Sigma-Aldrich Fine Chemicals, Cat no I4506) and HIgA (Sigma-Aldrich Fine Chemicals, Cat no I1010).

Secondary reagents were:
For identification of mouse antibodies: FITC labelled F(ab)2 rabbit anti mouse immunoglobulin (DAKO A/S, Glostrup, Denmark, Cat no F0313)=aMIg.

For identification of human IgG: FITC labeled F(ab)2 rabbit anti human IgG (DAKO A/S, Glostrup, Denmark, Cat no F0315)=aHIgG.

For identification of human IgA: FITC labeled F(ab)2 rabbit anti human IgA (DAKO A/S, Glostrup, Denmark, Cat no F0316)=aHIgA.

For identification of biotinylated antibodies: FITC labeled Streptavidin (DAKO A/S, Glostrup, Denmark, Cat no F0422).

the cytosol and nucleus (affibodies) are small α-helical structures not depending on S—S bridges for their conformation whereas the ligands which were shown not to be properly expressed in the cytosol/nucleus all have a conformation that is dependent on the formation of S—S bridges which are formed very poorly or not at all in the cytosol.

TABLE 2

Expression and functional ligand binding in recombinant adenovirus fibers targeted for secretion in COS cells

| | Detecting reagent | | | | | | |
|---|---|---|---|---|---|---|---|
| Fiber | 4D2+ aMIg | 2A6+ aMIg | a-EGF+ aMIg | a-MIg | a-Id+ aMIg | HigG+ aHIgG | HigA+ aHIgA |
| WT | + | + | ND | ND | ND | ND | ND |
| A7 EGF | + | + | + | ND | ND | ND | ND |
| A7 G250 | + | + | ND | + | + | ND | ND |
| A7 C242 | + | + | ND | + | + | ND | ND |
| A1 ZIgG | + | ND | ND | ND | ND | + | − |
| A7 ZIgG | + | ND | ND | ND | ND | + | − |
| A7 ZIgG/ZIgG | + | ND | ND | ND | ND | + | − |
| A7 ZIgA | + | ND | ND | ND | ND | − | + |
| A7 ZIgG/ZIgA | + | ND | ND | ND | ND | + | + |

TABLE 3

Expression and functionality of ligand binding in the nucleus of COS cells in native and selected recombinant fibers after targeting for expression in the cytosol

| | Detecting reagent | | | | | | |
|---|---|---|---|---|---|---|---|
| Fiber | 4D2+ aMIg | 2A6+ aMIg | a-EGF+ aMIg | a-MIg | a-Id+ aMIga | HigG+ HIgG | HigA+ aHIgA |
| WT | + | + | ND | ND | ND | ND | ND |
| A7 EGF | + | + | − | ND | ND | ND | ND |
| A7 G250 | + | + | ND | + | − | ND | ND |
| A7 C242 | + | + | ND | + | − | ND | ND |
| A1 ZIgG | + | ND | ND | ND | ND | + | − |
| A7 ZIgG | + | + | ND | ND | ND | + | − |
| A7 ZIgG/ZIgG | + | ND | ND | ND | ND | + | − |
| A7 ZIgA | + | + | ND | ND | ND | − | + |
| A7 ZIgG/ZIgA | + | ND | ND | ND | ND | + | + |
| A7 ZIgG Xa Knob | + | ND | ND | ND | ND | + | − |

Briefly, cells were centrifuged onto microscope slides in a Shandon Cytospin2 cytocentrifuge and air-dried over night at room temperature. The preparations were fixed in 3% paraformaldehyde in phosphate buffered saline, pH 7.4 (PBS), permeabilized with 0.1% Triton-X100 in PBS. After washing in PBS, preparations were incubated with primary reagents for 30 minutes at 37° C. in a humid chamber, washed again in PBS and incubated with secondary reagent for 30 minutes at 37° C. in a humid chamber. After washing in PBS, preparations were mounted in PBS with 50% glycerol and viewed in a Zeiss Axophot microscope equipped with appropriate light source and filters for FITC.

The results are shown below in Tables 2 and 3. It is obvious that all of the different ligands show appropriate binding when the corresponding fibers were expressed as secreted products. However, only the affibodies show the expected correct binding when the fibers were expressed in the cytosol and subsequently transported to the nucleus. Therefore, not all ligands can fold correctly in the cytosol and nucleus. It is interesting that the ligands which can withstand the milieu in The results have obvious implications for the construction of those re-targeted virus for human gene therapy where the viral structural components containing the new cell binding ligand are synthesized in the mammalian cell cytosol, i.e. adenovirus. Below are two enabling examples to show how such re-targeted adenovirus can be constructed.

Example 6

Grafting of CDR Loops

Certain single chain constructs of monoclonal antibodies retain their binding specificity even in the mammalian cell cytosol (Cattaneo et al., TIBTECH 17: 115-121, (1999)). This is a function of the so called frame work regions of the antibody variable regions. It is known that the antigen binding CDR loops can be transferred from one antibody to another by recombinant DNA technology thereby creating antibodies with frame work properties from one antibody and binding properties from another (for methodology see Emery et al., Strategies for Humanizing Antibodies, in Antibody Engineering, Carl A. K. Borrebaeck, (ed.), Oxford University Press 1995, page 159).

Such a loop-grafted single chain antibody, based on a variable domain framework capable of folding in the cytosol and subsequent transport to the cell nucleus thus created can subsequently be supplied with appropriate cloning sites at the gene level, ligated into fiber A7 RGD encoding genes and rescued into the adenovirus genome as described below (Example 7).

Example 7

Rescuing of Recombinant Fibers into the Adenovirus Genome

The wild type fiber as encoded in the Ad genome was substituted for recombinant fibers by the following method developed within the project. In the method the wild type Ad5 genome in the plasmid pTG3602 (Emery et al., Supra) was used as receptor for genes encoding the recombinant fibers. This plasmid contains the entire wild-type Ad5 genome joined to the plasmid backbone by Pac1 linkers. The entire genome can be recovered as a linear DNA fragment after cleavage with Pac1 since Pac1 sites are absent from the Ad genome. The resulting linear Ad DNA can then be transfected to susceptible cells to yield virus (Chartier et al., Supra). From this plasmid the Ad genome can also be cleaved as two fragments, one of 27 kb and one of 9 kb, using the enzymes Pac1 and Spe1. The 9 kb fragment has been cloned into pBluescript. From the 9 kb fragment, which contains the fiber, a 3 kb Sac1-Kpn1 fragment containing the fiber gene was further subcloned. The fiber gene was deleted between the Nde1 site in the tail-portion of the fiber and the Mun1 site which is situated just down-stream of the fiber-gene and an adapter containing an Xho1 site and the down-stream sequence was introduced between the Nde1 and Mun1 site to obtain a fiber shuttle vector. Several recombinant fibers have now been ligated between Nde1 and Xho1 of this shuttle vector and thereafter rescued into the 9 kb fragment mentioned above by homologous recombination in E. coli (Chartier et al., Supra). This means that all normal elements regulating fiber-expression have been left intact.

Finally, recombinant 9 kb fragments were separately joined to the 27 kb fragment by cosmid cloning to re-create the complete Ad genome.

The 27 kb fragment may also be derived from another adenovirus genome, such as the Ad-YFG described by He et al (He T-C, Zhou S, DaCosta L T, Yu J, Kinzler K W and Vogelstein B: A simplified system for generating recombinant adenoviruses. Proc Natl Acad Sci, USA, 95:2509-2514, 1998). If the 27 kb fragment is derived from pTG3602 the resulting genome will be WT E1+ whereas the 27 kb fragment from Ad-YFG will render E1 deleted viruses needing e.g. low passage 293 for replication.

The recombinant Ad genome resulting from above manipulations can finally be obtained as a linear fragment by cleaving with Pac1 and used to transfect permissive cell lines which then yield virus plaques if the genome is functional. For these transfections the FuGENE 6 transfection agent (Roche) was used.

Various recombinant fibers were rescued into the Ad genome and subsequently transfected into permissive cells. Results are shown below in table 4. Of the fibers accounted for, only those containing the WT knob and the affibody A7 ZIgG/IgG were capable of rendering functional virions. The results are in complete concordance with those shown in tables 2 and 3.

TABLE 4

Rescuing of recombinant fibers into virions

| Fiber | Transfected cells | Occurrence of virus plaques |
|---|---|---|
| A7 WT Knob | 293 | Yes |
| A7 EGF | A549 | No |
| A7 C242 | Colo 205 | No |
| A7 G250 | A75 | No |
| A7 ZIgG/ZIgG | 293/Fc* | Yes |

*293/Fc cells are 293 cells stably transfected with Fc3(1) from human IgG expressed as a membrane protein.

To create 293/Fc, cloned Fc3(1) from human IgG which reacts with the Z-domain (Jendeberg, L., Nilsson, P., Larsson, A., Nilsson, B., Uhlén, M. and Nygren, P.-Å (1997) "Engineering of Fc1 and Fc3 from human immunoglobulin G to analyse subclass specificity for staphylococcal protein A" J. Imm. Methods 201, 25-34.) was ligated into the vector pDisplay (Invitrogen) in frame with the PDGFR transmembrane domain sequence present in this vector. The coding sequence containing the Fc sequence fused to the PDGFR transmembrane domain sequence was then cleaved from the vector using the restriction enzymes Sfi1 and Not1 and ligated into the vector pSecTag (which carries the Zeocin resistance gene) cleaved with the same enzymes. The reconstituted vector was the transfected into low passage 293 cells using FuGENE and the cells were placed under selection pressure using Zeocin to select for stably transformed cells. Clones were isolated and tested for membrane expression of membrane-bound Fc3(1) using FITC labeled staphylococcal protein A (Sigma). One 293 clone which homogenously expresses membrane bound Fc was used for transfection of the A7 ZIgG/ZIgG containing genome to produce virions.

Example 8

Assembly of Gene Constructs Encoding Recombinant Adenovirus Fibers with an Affibody and a Cleavable Wild Type Knob Cleavable fibers containing both a non-native polypeptide comprising an external ligand, here an affibody, and a C-terminally placed wild type knob were constructed with an activated factor X site situated between the cell binding structures so that the knob can be cleaved off to expose the affibody. This permits virus production in 293 cells with subsequent infection of new target cells as defined by the affibody after proteolytic removal of the knob.

To construct a gene for a cleavable fiber for ligation of different ligands the WT fiber was subjected to PCR with an upstream primer (437) introducing Cla1, Mun1 and the Factor Xa recognition site before the first seven triplets of repeat 22 and the downstream primer 149 which primes at the end of the fiber knob. After cloning and restriction with Cla1 and Xho1 the DNA fragment was cloned into the A7 fiber construct mentioned earlier. The resulting fiber gene contains from the N-terminus the sequence for the tail, the first seven shaft repeats, the NRP trimerisation signal, the linker from staphylococcal protein A, a Cla1 site, a Mun1 site, the Xa cleavage site, repeat 22 and the wild type knob. For ligation into this fiber gene the gene for the affibody ZIgG was supplied with an upstream Cla1 site and a downstream Mun1 site by PCR using primers 503 and 505 and ligated into the aforementioned "Xa fiber" gene. The resulting fiber gene contains from the N-terminus the sequence for the tail, the first seven shaft repeats, the NRP trimerisation signal, the linker from staphylococeal protein A, a Cla1 site, the new linker, a Mun1 site, the Xa cleavage site, repeat 22 and the wild type knob.

The fiber gene was rescued into the adenovirus genome (see Example 7). The recombinant genome was transfected into 293 cells and virions were produced and purified on CsCl gradients. Purified virions were cleaved with activated Factor X (Xa) (Sigma) in 50 mM Tris-Cl pH 8,0; 100 mM NaCl; 5 mM $CaCl_2$ for 48 hours at room temperature. 1 U of Xa was used for 5 µL of virus suspension.

Assay for binding of the ZIgG affibody on the virions was performed essentially as follows. Virus suspensions were blotted onto PVDF membranes (BioRad). After blocking with 3% gelatin in Tris buffered saline, pH 7,4 (TBS) the membranes were incubated with FC 10 µg/mL in 1% gelatin in TBS for 90 minutes at room temperature, washed, incubated with anti-human IgG-HRP (Dakopatts) in TBS/1% gelatin for 90 minutes at room temperature, washed and developed in 4-Chloro Naphtol reagent (BioRad). The results of staining of WT and recombinant viruses are shown in FIG. 3 along with different controls. It is obvious that the recombinant virus binds Fc3(1) which binds to WT Z whereas Fc3 which does not bind to WT Z (Jendeberg, L., Nilsson, P., Larsson, A., Nilsson, B., Uhlén, M. and Nygren, P.-Å. (1997) "Engineering of Fc1 and Fc3 from human immunoglobulin G to analyse subclass specificity for staphylococcal protein A" J. Imm. Methods 201, 25-34) fails to bind to the recombinant virus. WT virus does not bind either Fc preparation.

Example 9

Assay of Non-native Polypeptides for Functional Conformation and Binding Specificity The candidate polypeptide is expressed as part of a viral component protein by means of insertion of the corresponding coding sequence into a suitable construct. The construct, which comprises an entire viral genome in which one or more components have been replaced by the corresponding recombinant component gene, is expressed in a cell line suitable for propagation of the recombinant virus coded for by the recombinant viral genome. There are two main possibilities depending on whether the WT cell-binding function is retained in the recombinant genome or not.

If the WT cell-binding function is retained virus can be produced in normal producer lines such as 293 for adenovirus. The ability of the non-native polypeptide to be expressed in a conformation that allows it to bind to an extracellular ligand and to be part of a functional virion is assayed by binding studies on virions. This approach is exemplified by the strategy employed in Example 8 above where the virus fiber contains both the WT knob and a non-native binding ligand and where the knob can be removed by proteolytic cleavage. The binding function of the non-native polypeptide was demonstrated by standard solid phase immunotechnology. Another strategy to meet the same ends would be to produce virions with WT fibers as well as recombinant fibers, the latter containing the non-native polypeptide as replacement for the native knob.

If the WT cell-binding function has been deleted from the viral genome the virions will depend on the non-native polypeptide for cell binding. Therefore, the cell line must be able to permit entry of the recombinant virus and, if necessary, to supply genetic information that may be missing from the recombinant virus, e.g. the sequence for E1. If the recombinant genome is E1 deleted, one solution is to use an E1 transfected cell line such as 293 and to stably transfect these with a receptor capable of binding the non-native polypeptide coded for by the recombinant viral genome. The ability of the non-native polypeptide to be expressed in a conformation that allows it to bind to the corresponding receptor structure and form part of a functional virion is assayed by screening for plaque formation in the cells following transfection of the viral genome. This strategy was employed in Example 7 above where 293 cells stably expressing membrane bound Fc from human IgG was used to produce virions where the WT binding function was replaced with the affibody ZIgG. The exact binding properties of the non-native polypeptide can further be determined in studies where the virus is allowed to compete for binding with peptides structurally related to the non-native polypeptide responsible for cell-binding.

Example 10

Anti β-galactosidase Single Chain Fv Fragment

In a continuation of the experiments described in Example 3, a single chain variable chain fragment (VK, linker, VH) reactive with β-galactosidase and capable of being expressed in the cytoplasm (Martineau P and Betton J-M: J. Mol. Biol. 292, 921-929 (1999)) was cloned into the aforementioned A7 fiber constructs. This single chain fragment is [SEQ. ID. NO.: 47). To permit cloning into the aforementioned A7 fiber constructs, the single chain fragment was cut with Nco1/EcoR1 from the plasmid pPM163R4 (Martineau P and Betton J-M supra) and ligated into a plasmid containing the aforementioned Fiber R7 EGF supplied with a Cla1-Nco1-EcoR1-Xho1 adapter allowing for in-frame ligation of the single chain fragment.

In a continuation of the experiments described in Example 5, expression and cellular localization of recombinant fibers containing the single chain variable chain fragment (VK, linker, VH) reactive with β-galactosidase were evaluated by immunostaining using the following additional primary reagent: β-galactosidase-biotin (SIGMA, G 5025).

In addition to the results shown in Table 2, results results obtained in equivalent experiments for the Anti β-galactosidase single chain Fv fragment fiber construct are shown Table 5:

TABLE 5

Expression and functional ligand binding in recombinant adenovirus fibers targeted for secretion in COS cells

| Fiber | 4D2+ aMIg | 2A6+ aMIg | β-galactosidase + StrAv-FITC |
|---|---|---|---|
| R7 a-β-galactosidase | + | + | + |

In addition to the results shown in Table 3, results obtained in equivalent experiments for the Anti β-galactosidase single chain Fv fragment fiber construct are shown Table 6:

TABLE 6

Expression and functionality of ligand binding in the nucleus of COS cells in native and selected recombinant fibers after targeting for expression in the cytosol

| Fiber | 4D2+ aMIg | 2A6+ aMIg | β-galactosidase + StrAv-FITC |
|---|---|---|---|
| R7 a-β-galactosidase | + | + | + |

Example 11

Phenotypic Analysis of Fiber Proteins

The following is a further example of modified viruses of the present invention wherein complex polypeptide ligands have been incorporated into a modified adenoviral fibre protein. The example demonstrates the importance for generation of a re-targeted viable and functional Ad vector of two features: (i) the fibre structure modifications should still allow for efficient attachment and cellular entry of the virus, and (ii) ligands inserted into the fibre should be capable of correct folding in the mammalian cell cytoplasm. Solubility is conveniently used to assess correct folding which is typically linked to an absence of disulphide bonds. Preferably the non-native polypeptides described herein will have no more than 2 disulphide bonds, typically no more than 1 and most preferably no disulphide bonds.

Materials and Methods

Cells. HEK-293 cells were obtained from Microbix Inc. (Toronto, Ontario, Canada). Cos7, A431 and Colo205 cells were purchased from the American Type Culture Collection (ATCC; Manassas, Va.) and A75 and G43 cells were obtained from Reinder Bolhuis (Daniel Den Hoed Cancer Center, Rotterdam, The Netherlands). All cells were maintained at 37° C. and 5% $CO_2$ in Iscove's medium (Gibco BRL), supplemented with 10% fetal bovine serum (Sigma-Aldrich) and 50 mg/ml Gentamicin (Gibco BRL). *Spodoptera frugiperda* (Sf9) cells (ATCC) were cultured at 28° C. in TC 100 medium (Gibco BRL) with the same supplements as above.

Antibodies. Monoclonal antibody (mAb) against epidermal growth factor (EGF) was purchased from Cambio Ltd. (Cambridge, UK). Antibodies directed against the Vα and Vβ domains of single chain T-cell receptor (scTCR), and anti-idiotypic antibodies directed against mAb G250 (NUH31 and NUH84) were kindly supplied by Reinder Bolhuis. MAb against fiber tail (4D2.5), and mAb against fiber trimer (2A6.36) were obtained from Jeff Engler (University of Alabama at Birmingham, Ala.). CAR-blocking, fiber knob directed mAb 1D6.14 was supplied by Buck Rogers (UAB at Birmingham, Ala.). The monoclonal antibody RL2, which is specific for O-linked GlcNAc residues, was obtained from Larry Gerace via Jeff Engler. Biotinylated anti-idiotypic antibodies directed against mAb C242 (Id1, Id13 and Id20) were produced from the original hybridomas. Horse radish peroxidase (HRP)-labeled streptavidin, fluorescein isothiocyanate (FITC)-labeled rabbit anti-mouse immunoglobulin G and streptavidin-FITC were purchased from DAKO (Glostrup, DK).

Generation of recombinant knobless fibers and nomenclature. Recombinant fiber genes were constructed using methods based on ligation, PCR, and splicing by overlap extension (SOE). Gene sequences generated by PCR were sequenced before subcloning. The gene encoding the Ad5 WT fiber was obtained from pAB26 (Microbix, Toronto, Canada) by PCR using the forward primer (SEQ ID NO: 48) 5'-CTC GGA TCC GAT GAA GCG CGC AAG ACC GTC TGA A-3' and reverse primer (SEQ ID NO: 49) 5'-TTC CTC GAG TTA TTC TTG GGC AAT GTA TGA-3' introducing an upstream Bam H I and a downstream Xho I site, respectively. In recombinant fibers, the knob domain was deleted and replaced by a 36 amino acid (aa) extrinsic trimerisation motif derived from the neck region peptide (NRP) of human lung surfactant protein D. The NRP sequence (PDVASLRQQ-VAELQGQVQHLQAAFSQYKKVELFPNG) (SEQ ID NO:2), followed by a linker sequence from *Staphylococcus* protein A (Staph-A linker: AKKLNDAQAPKSD), was ligated to the C-terminal end of fiber shaft of different lengths, 1, 7 or 22 repeats.

The resulting constructs were named R1, R7 and R22, respectively. Re-targeting ligands were added to the C-terminal end of the Staph-A linker. For convenient cloning of various ligands, Cla I and Xho I sites were introduced after the linker sequence. All ligands mentioned below were provided with these restriction sites, and the name of the ligand was indicated after the number of shaft repeats in the fiber name. E.g., R1-RGD, R7-EGF, etc (FIG. 4). R7-knob referred to a truncated fiber shaft (repeats 1 to 7), carrying NRP, the Staph-A linker and the natural knob domain, including the last shaft repeat and the shaft-knob junction (FIG. 4). For two R7-knob fiber constructs, an extra linker was inserted into the Nhe I site located on the N-terminal side of NRP. These linkers were derived from the Ad5 WT fiber shaft repeat 17 (L17: TTTACAGCTTCAAACAATTC-CAAAAAGCTTGAG) and fiber shaft repeat 22 (L22 GGAAACAAAAATAAT-GATAAGCTAACTTTGTGTGACC) were named as R7-L17-knob and R7-L22-knob, respectively. The schematic representation of the fibers is shown in FIG. 4.

Targeting ligands. Polypeptide ligands. Double stranded DNA fragments containing the RGD or ACDCRGDCFCG (abbreviated RGD4C) motifs were synthesized as complementary oligonucleotides with single-stranded terminal adapters, and annealed together. The fragment containing the shaft repeat 22, the shaft-knob junction and the entire knob was obtained by PCR from the WT Ad5 fiber gene. The DNA sequence for human EGF was synthesized, cloned and verified by sequencing. The cloned single chain T-cell receptor (which contains disulfide bonds) with specificity towards Mage1/HLA A1 was obtained from Reinder Bolhuis. The scTCR used had the format Vα-Linker-VβCβ.

Monoclonal antibodies. Two mAb single chain fragments (scFv) were used. The first scFv consisted of the variable kappa chain (or VK), a spacing linker, the variable heavy chain (or VH), the joining sequence (JS) and the constant heavy chain domain 2 (or CH2) of mAb G250. MAb G250 has been shown to have a high specificity towards a surface antigen of human renal carcinoma cells.

Affibodies. The second scFv contained the same basic structure VK-linker-JS-VH, and derived from mAb C242, which reacts with colorectal and pancreatic carcinomas. However, to obtain a better selectivity for the designed target cells, a library of C242 scFv-derived affibodies was generated by SOE, using cDNA from the mAb-producing hybridoma cells as the original template. A randomized 18 amino acid peptide ligand $(SNN)_{18}$ was inserted between the VK and VH domains, where S was dA, dG or dC and N was dA, dG, dC or dT. Affibodies were selected by phage display on colorectal carcinoma cells Colo205, and the sequence PPDFVPPAAS-FPDHSPRG was identified for the peptide ligand. The C242 scFv VK-(PPDFVPPAASFPDHSPRG)-VH was then selected for further work based on its antigen binding ability.

Cellular expression and localization of fiber and ligand reactivity. The genes encoding recombinant fibers were cloned into the vectors pcDNA3.1 and pSecTag2 (Invitrogen BV, Groningen, Germany) for intracellular expression and extracellular release, respectively. Vectors were transfected into Cos7 cells using Lipofectamin (Life Technologies Inc., Gaithersburg, Md., USA) following the manufacturers' instructions. Expression, nuclear transport and functional expression of the fibers with the new cell binding ligands were evaluated by immunostaining as follows. Cells were centrifuged onto microscope slides in a Shandon Cytospin2 cytocentrifuge and air-dried over night at room temperature. The preparations were fixed in 3% paraformaldehyde in PBS and permeabilized with 0.1% Triton-X100 in PBS. After washing in PBS, preparations were incubated with primary antibodies (anti-fiber mAb, or anti-ligand mAb) for 30 min at 37° C. in a humid chamber, washed again in PBS and incubated with secondary antibodies labeled with FITC for 30 min at 37° C. in a humid chamber. After washing in PBS, preparations were mounted in PBS with 50% glycerol and viewed in a Zeiss Axioskop microscope equipped with appropriate light source and filters for FITC.

Phenotypic analysis of fiber proteins. Recombinant fiber proteins were expressed in insect cells infected with recombinant baculoviruses, and analysed according to four criteria: (i) solubility, (ii) trimerization, (iii) glycosylation and (iv) assembly with recombinant penton base in vivo to form penton capsomers.

(i) For immunological quantification of soluble versus insoluble recombinant fiber fractions, Sf9 cells were lysed in hypotonic buffer (10 mM Tris-HCl buffer, pH 7.5) at 0° C., and the cell lysates were adjusted to isotonic conditions (150 mM NaCl in 10 mM Tris-HCl, pH 7.5) and subjected to centrifugation at 15,000×g for 10 min. Supernatants and pellets were then analyzed by conventional SDS-PAGE and immunoblotting, using anti-tail 4D2.5 mAb as primary antibody, and [$^{35}$S] SRL-labeled anti-mouse IgG secondary antibody (Amersham Pharmacia Biotech; 100 μCi/ml; 5 μCi per blot). (ii) Oligomerization status of fiber was assayed by means of non-denaturing SDS-PAGE (referred to as NDS-PAGE) and conventional, denaturing SDS-PAGE. NDS-PAGE differed from SDS-PAGE in that the samples were not denatured by boiling in SDS sample buffer prior to electrophoresis. (iii) Glycosylation of recombinant fibers was assessed both by immunoreaction on blots using the monoclonal antibody RL2 and chemical detection using the DIG Glycan Detection Kit (Roche). (iv) Assembly of fiber with penton base was assayed by co-infecting the same Sf9 cells with two recombinant AcNPV, one expressing the penton base, the other expressing the fiber protein.

The presence of penton capsomer was detected in cell lysates after 40 h post-infection, and analysed by PAGE in native conditions, at low voltage overnight with cooling. Immunological quantification of native penton, penton base and fiber proteins was performed as above, using the corresponding primary antibody (anti-penton base or anti-fiber), followed by [$^{35}$S] SRL-labeled anti-mouse or anti-rabbit whole IgG secondary antibody. Blots were exposed to radiographic films (Hyperfilm beta-max, Amersham Pharmacia Biotech), and autoradiograms were scanned at 610 nm, using an automatic densitometer (REP-EDC, Helena Laboratories, Beaumont, Tex.). Alternatively, protein bands were excised from blots and radioactivity measured in a scintillation counter (Beckman LS-6500).

Rescue of recombinant modified fibers into virions. Recombinant fibers were rescued into the Ad5 genome as described above. Briefly, a 9 kb-fragment from the Ad5 genome, spanning map units (mu) 75.4 to 100 and containing the WT fiber gene, was generated by Spe I and Pac I digestion of pTG3602. The plasmid pTG3602 contained the entire WT Ad5 genome bounded by two Pac I sites. The 75.4-100 mu-fragment was then cloned into pBluescript II SK(−) (Stratagene), after addition of a Pac I site in its MCS, generating the plasmid pGAG9. From pGAG9, a Sac I-Kpn I 3 kb-fragment was then subcloned into pBluescript II SK(−). A large deletion downstream of the Nde I site (located within the tail domain of Ad5 fiber) was created in the 3 kb-fragment, and the deleted sequence replaced by a Xho I site-containing linker. This generated the plasmid pGAG3, which was the receiving plasmid for all our fiber gene constructs, inserted between Nde I and Xho I sites. pGAG3-inserted recombinant fibers were re-introduced into pGAG9 digested with Nhe I, using homologous recombination in E. coli BJ5183. The resulting recombinant pGAG9 was then excised from the vector with Spe I and Pac I, and joined to the isolated 27 kb-fragment (0-75.5 mu) representing the left-hand segment of the Ad5 genome by Cosmid cloning (SuperCos 1 Cosmid Vector Kit and Gigapack III Gold Packaging Extract, Stratagene). The presence of the correct recombinant fiber in the cosmid clones were verified by PCR and restriction analysis using Spe I and Hind III.

For virus production, recombinant cosmid genomes were isolated after restriction with Pac I, and transfected into cells expressing the receptors corresponding to the fiber-inserted ligand. In standard transfection reactions, 2 μg DNA and 3 μl FuGENE (Roche) were used per 35-mm well, according to the manufacturer's protocol. Ad5 genomes with fiber gene containing either RGD motifs or the WT fiber knob as ligands were transfected into 293 cells. For the other liganded fibers, Ad5 genomes with the EGF ligand were transfected into A549 cells, scFv-C242 into Colo 205 cells, scFv-G250 into A75 cells and scTCR specific for Mage1/HLA A1 into G43 cells. At least three different transfections were simultaneously performed, each one using a 6-well plate. The occurrence of plaques was determined by microscopic observation of the transfected cell cultures. Verification of recombinant fiber sequence was made by PCR with specific primers for each fiber construct.

Characterization of Recombinant Fiber and Ad5 Virions.

Cellular expression. To evaluate the level of fiber expression, 293 cells were infected with 10 pfu/cell of WT, R7-knob and R7-RGD virus. Cells were harvested and freeze-thawed four times analyzed by SDS-PAGE and western blotting. The blots were reacted with 4D2.5 and revealed with HRP-labeled anti-mouse IgG (DAKO).

Fiber content of Ad5 virions. The fiber copy number of virions was determined, after CsCl purification of Ad5 virions, by SDS-PAGE and western blot analysis as above. The virus loads in acrylamide gels were normalized for equal amounts of infectious particles, determined by virus titration on 293 cells (expressed as plaque forming units/ml; PFU/fml), and for equal amounts of physical particles (PP), determined by protein assay (BioRad). The number of PP was determined by SDS-PAGE analysis and Coomassie blue staining of Ad5 recombinants, co-electrophoresed with a range of standard bovine serum albumin (BSA) samples (2x crystallized, BioRad). Protein content of hexon bands was evaluated by comparison with BSA standard bands, by scanning in an automatic densitometer (REP-EDC, Helena Laboratories, Beaumont, Tex.). The number of Ad5 PP in samples was calculated from the mass of 2.91×10e−16 g per single virion, i.e. 2.91 mg per 10e+13 virions. The infectivity index represented the ratio of infectious to physical particles.

Growth rate of recombinant Ad5. Growth-rate was measured by the production of plaques in 293 cells. In standard assays, virus in PBS was adsorbed to cell monolayers (4×10$^4$ cells per sample) at 37° C. for 1 h. The cells were rinsed once and further incubated in Iscove's medium supplemented with 10% FCS and 50 mg/ml gentamycin at 37° C. Cells were harvested at 24, 48 and 72 h after infection (pi), centrifuged, dissolved in 0.2 ml PBS and freeze-thawed four times. The supernatants were titered on 293 cells, and the titer expressed as plaque forming units per ml. The total Ad protein content was measured by the IDEIA™ Adenovirus kit (DAKO).

Gene transduction efficiency. Monolayers of 293 cells in 24-well plates were infected as described above with 10 pfu/cell of the recombinant viruses. Cells were harvested at 24 h pi, washed with ice-cold PBS followed by fixation in 0.5% glutaraldehyde for 15 min. After three washes in PBS, the cells were analysed for transgene GFP expression, using the FL1 emission channel in a FACScan cytometer (Becton-Dickinson, San Jose, Calif.).

Assay for fiber knob in viral capsids. The presence or absence of accessible knob in virions was assessed by ELISA. Purified virions were diluted with 50 mM carbonate-bicarbonate buffer pH 9.6, to a final concentration of 5×10$^5$ PFU/ml. Aliquots of 100 ml were adsorbed onto ELISA plates overnight at 4° C. Material adsorbed in wells was fixed with 0.5% glutaraldehyde, after which the wells were washed with PBS containing 0.1% Tween-20 (washing buffer), and blocked for 2 h with 200 ml PBS containing 1% BSA. Wells were then washed three times in washing buffer and incubated for 1 h at room temperature with 100 ml of biotinylated anti-knob mAb 1D6.14 at a concentration of 1 mg/ml. Bound antibody was detected using HRP-streptavidin (DAKO) at a dilution of 1:2,000, for 1 h at room temperature. Colour development was obtained with TMB substrate (CanAg Diagnostics, Göteborg, Sweden), and stopped with 0.12 M HCl for 10 min. Plates were read in a microtiter plate reader set at 450 nm.

Rationale for the Construction of Recombinant Fibers.

Knobless fibers with the extrinsic trimerisation motif (NRP) from human lung surfactant protein D were constructed with different numbers of shaft repeats and different ligand structures. The three constitutive elements of these fiber constructs were considered from a structural and functional point of view: (i) the fiber scaffold, (ii) the flexible linker and (iii) the cell ligands.

Fiber scaffold. The fibers were named according to the number of shaft repeats and the ligand present. As an example, R7-EGF contained the fiber tail, the N-terminal 7 shaft repeats, the NRP motif and the C-terminal EGF peptide as the cellular ligand. R1-RGD fiber had only one shaft repeat (the first one) and RGD as the ligand, etc. Of three possible shaft lengths, short (1 repeat), medium (7 repeats) and long (22 repeats) repeats, the intermediate size fiber with 7 repeats (R7) was chosen as the building scaffold for further constructions and studies with different ligands. For reasons discussed below, the rationale for chosing R7 was based on its high solubility as recombinant protein, the maintenance of most of the fiber biological functions, and on the yields of Ad5/FibR7 virus progeny. The study on the comparative advantages of fiber shafts of different lengths was performed with R1-RGD, R7-RGD and R22-RGD fibers, three constructs carrying the same cellular ligand RGD.

Linker. To evaluate the possible advantage of an additional linker in the fiber shaft domain, two R7-NRP-knob fibers were constructed with an extra peptide linker inserted between the shaft domain and the NRP motif. Two virus-derived linkers were thus tested, the Ad5 shaft repeat 17 (L17) and the Ad5 shaft repeat 22 (L22). The resulting recombinant fibers were named R7-L17-knob and R7-L22-knob, respectively.

Cellular ligands. Several ligands were tested and compared for functionality. These ligands were designed to re-targeted Ad5 vectors to cell surface molecules of broad distribution, like integrins or HLA molecules, or to less ubiquitous molecules, like malignant cell specific determinants. They varied in size and complexity from a simple tripeptide motif, like RGD, to more elaborated structures, like scTR or scFv, which consist of several polypeptide domains with requirement for proper folding.

Expression of fibers and ligands in mammalian cells. Recombinant fibers were first transiently expressed in mammalian cells, using plasmid-transfected Cos7 cells. The recombinant fibers were expressed from two different vectors, one designed for intracellular expression of recombinant proteins, the other for their extracellular release via the secretory pathway. Cells were assayed for the level of fiber expression, cellular localization and functionality of their ligands. All the different fibers tested exhibited apparent appropriate ligand binding when recovered as secreted proteins. For fibers synthesized from the intracellular expression vector, nuclear localization was observed in all cases, except for R7-L22-knob. This implied that the cytoplasmic transit and the traverse of the nuclear pore occurred as efficiently for the modified fibers as for WT Ad5 fiber.

However, none of the extrinsic ligands fused to fibers showed the expected binding activity. Even though the intracellularly expressed R7-scTCR fiber could be detected within the nucleus, and was stained with an anti-Va mAb recognizing an epitope independent of the Va domain conformation, no staining could be detected with another, conformation-dependent mAb, directed against the Vb domain. In order to test the possible detrimental effect of the fiber domain on the reactivity of intracellular ligands, our ligands were also expressed as separate constructs from the vector pcDNA. There was no detectable binding of the nonfused intracellular ligands to their specific mAbs, indicating that the ligands behaved similarly when free or fused to the fiber.

There was therefore a profound difference in binding ability between fiber-ligand fusions designed for secretion and designed for cytoplasmic expression. This suggested that fiber-ligand fusion proteins designed to follow the secretory pathway underwent a proper folding and were in the correct conformation. This did not imply that all intracellular fiber-ligand fusion proteins would fold incorrectly, since the cellular environment also seemed to play a major role in this process. A significant difference could be detected between the cytosol of Cos7 and Sf9 cells, in terms of folding pattern and reactivity of fiber-ligand fusion proteins. This was the case for the fiber knob domain of R7-L22-knob, the EGF ligand of R7-EGF and the scFV ligand of R7-G250, which showed some reactivity in Sf9 cells but not in Cos7 cells.

Phenotype of recombinant fibers expressed in insect cells. To further analyze the properties of the liganded fibers, our different constructs were expressed as recombinant proteins in the baculovirus-insect cells system, and assayed for protein solubility, trimerisation, glycosylation and formation of penton by assembly with penton base in vivo in Sf9 cells.

Protein solubility and conformation. The solubility of recombinant proteins is usually considered as a good indicator of their proper folding. We therefore tested all our recombinant fiber proteins for their total expression in insect cells, and determined the proportion recovered in the soluble fraction of the cell lysates. All the fiber recombinants were highly expressed in Sf9 cells, at levels similar to WT Ad5 fiber, although their degree of solubility varied significantly from one to another. We estimated that fibers had a WT-like solubility and thus a proper folding when the soluble fraction contained more than 50% of the total fiber expressed. A fiber could be considered as misfolded when its soluble fraction represented less than 20% of the total. According to these criteria, WT, R7-knob, R7-L17-knob, R7-L22-knob, R1-RGD, R7-RGD and R7-RGD4C fibers were mainly recovered in the soluble fraction (60-95% solubility). In contrast, only 22% of R22-RGD, and less than 15% of R7-EGF, R7-C242 and R7-scTCR fiber was found to be soluble, confirming their incorrect folding suggested by the absence of reactivity with their respective mAbs. The least soluble fiber constructs was R7-G250, which was recovered at 95% in the insoluble fraction (see FIG. 5 and Table 7 below).

TABLE 7

Phenotypic characterization of recombinant fibers expressed in baculovirus infected Sf9 cells (a)
Trimerization (b)

| Fiber | Glycosylation | NDS-PAGE | IF | Assembly (c) with penton base | Solubility (d) (%) |
|---|---|---|---|---|---|
| WT | + | + | + | + | 60 |
| R7-knob | + | + | + | + | 72 |
| R7-L17-knob | + | + | + | + | 70 |
| R7-L22-knob | + | + | + | + | 75 |
| R1-RGD | − | − | + | + | 89 |
| R7-RGD | − | + | + | + | 94 |
| R22-RGD | − | + | + | + | 22 |
| R7-RGD4C | + | + | + | + | 78 |
| R7-EGF | − | ND (e) | + | ND | 13 |
| R7-C242 | − | ND | − | ND | 11 |
| R7-G250 | − | ND | − | ND | 5 |
| R7-scTCR | − | ND | + | ND | 12 |

(a) Baculovirus-infected Sf9 cells were harvested at 48 h after infection and recombinant fibers assayed for different biological functions, solubility, O-GlcNAc glycosylation, trimerisation, and penton capsomer formation.
(b) Trimerisation status of fibers was determined in vitro by electrophoresis of Sf9 cell lysates in SDS-gel without heat denaturation (NDS-PAGE), and in situ, by immunofluorescence staining of fixed cells, using anti-trimer mAb (2A6.36).
(c) The capacity of fibers to assemble with penton base to form penton capsomer was assayed by co-infection of the same Sf9 cells by two different recombinant baculoviruses, one expressing Ad fiber, the other Ad penton base. Sf9 cell lysates were analysed at 48 h after co-infection for the occurrence of penton (base + fiber), by electrophoresis of native proteins in non-denaturing 6% acrylamide gels (Karayan et al., 1994)
(d) Solubility was assayed in single baculovirus-infected Sf9 cells. Cells harvested at 48 h after infection and lysed in isotonic buffer, and cell lysates divided in two aliquots. One aliquot was centrifuged at 10,000 × g for 10 min and supernatant was kept, whereas the other was analysed as whole cell lysate. Both aliquots were denatured at 100° C. in SDS-sample buffer and electrophoresed in denaturing SDS-gel, and blotted. Blots were reacted with anti-fiber-tail mAb 4D2.5, and radiolabeled secondary antibody, as shown in FIG. 5. Immunoblots were quantitated by autoradiogram scanning and the results were expressed as the percentage of soluble versus total fiber content. Average of three determinations; SD was within 15% of the reported value for the mean.
(e) ND, not detectable.

Trimerisation. The ability of the different fibers to self-assemble into trimers were electrophoretically determined in vitro by NDS-PAGE analysis of cell lysates, and immunologically in situ by immunofluorescence staining of fixed cells. According to their electrophoretic patterns, R7-EGF, R7-C242, R7-G250 and R7-scTCR were incapable of forming homotrimers, whereas R7-knob, R7-L17-knob R7-L22-knob, R7-RGD, R22-RGD and R7-RGD4C trimerized at WT levels (Table 7). However, immunofluorescence staining of cells using the anti-trimer mAb 2A6.36 showed that all except R7-C242 and R7-G250 formed trimers (Table 7). The apparent discrepancy likely resided in the method of detection, or in the possibility that R7-EGF, R7-C242, R7-G250 and R7-scTCR fiber trimers became unstable in vitro, or both. Whatever the reason, if fiber trimers formed with a very low efficiency within the cells, immunofluorescence staining was, in this case, more sensitive and more appropriate for trimer detection.

Glycosylation. Likewise, the glycosylation of fibers was analysed by western blotting using RL2, a mAb specific for peptide-linked O-GlcNAc residues. The fiber constructs which reacted with RL2 were, besides the WT, R7-L17-knob, R7-L22-knob, R7-knob and R7-RGD4C (Table 7).

Assembly with penton base. When Sf9 cells were infected with two different baculoviruses, one expressing the Ad fiber, the other the penton base, the two proteins are capable of interacting intracellularly to form penton capsomers. When assayed for this property, the fiber proteins R7-EGF, R7-C242, R7-G250 and R7-scTCR had lost their capacity to assemble with penton base, whereas the other eight recombinant fibers had conserved their assembly function (Table 7).

Rescue of recombinant fiber genes into the viral genome and viability of the viruses. Our recombinant fiber genes were reinserted into the Ad5 viral genome in replacement of the WT fiber gene. Each recombinant viral genome was then introduced by transfection into the corresponding cell line which express the proper receptor for the recombinant fiber. The rescue of viable recombinant viruses was assessed by plaque development. Plaques were observed for the Ad5 genomes harboring the WT fiber, and recombinant fibers R7-knob, R7-L17-knob, R1-RGD, R7-RGD and R7-RGD4C.

Fiber content, infectivity and growth rate of recombinant viruses. The recombinant R7-RGD Ad carrying seven shaft repeats had been selected as the best choice in terms of fiber trimerisation, stability, assembly with penton base and ligand binding. However, this knobless Ad was less efficient in virus assembly and production, compared to WT virus. In this example, the characteristics of the Ad-R7-knob, which carried the knob domain, were compared to those of WT Ad and knobless Ad-R7-RGD. We first assayed for the production of fibers in 293 cells infected with each of the three Ad at different times pi. The production of fiber proteins from R7-knob Ad was comparable to that of the WT Ad, whereas the level of fiber protein from the R7-RGD Ad was significantly lower.

We then compared the fiber content per virion of the R7-knob Ad with that of the WT Ad. The two viruses exhibited similar amounts of fiber content when normalised to the number of physical particles (PP) but there were more fiber protein in the R7-knob Ad when the two virus samples were normalised to the number of infectious particles (PFU). This indicated that R7-knob Ad was less infectious than the WT. This was confirmed by the infectivity index (PFU:PP ratio), which was calculated from the infectious titer (expressed as PFU/ml, as determined by titration on 293 cells), and from the concentration of PP (determined by biochemical methods). The infectivity index of the Ad-R7-knob (1:100 to 1:200) was 2- to 8-fold lower than that of WT Ad5 (1:25-1:50). The infectivity index of Ad-R7-RGD (1:200-1:500) was in a similar range as that of Ad-R7-knob.

The growth rate of the Ad-R7-knob was compared to that of WT virus. Aliquots of cell samples were infected at the same MOI, and infectious virus progeny, determined by plaque assays on 293 cells. The growth curves for the three viruses were similar, but the production of infectious Ad was inferior to the WT for both Ad-R7-knob and Ad-R7-RGD. Virus uptake was also examined for Ad-R7-knob, and estimated from its ability to transduce the GFP reporter gene into 293 cells, as compared to Ad5-GFP carrying WT fibers (Ad-WTFib). The transducing capacity per PP was found to be 6-fold lower for the R7-knob Ad than for Ad-WTFib.

Receptor-binding capacity of recombinant virions. Ad-FibR7-knob was assayed for its receptor binding capacity, as compared to WT virus. Both WT Ad5 and Ad-FibR7-knob virions were found to react with anti-knob mAb in ELISA, suggesting that the knob epitopes were accessible to mAb on both types of virions. However, the knob immunoreactivity was higher for WT Ad than for Ad-FibR7-knob. This suggested that the cell binding determinants of virions were more efficient or/and had a higher affinity when the knob was carried by a 22-shaft-repeat fiber, as in WT Ad5, than by a shorter, 7-repeat fiber.

These results show that the ligands which were found to be improperly folded within the cytosol and the nucleus all had a conformation that was highly dependent on the formation of disulfide bridges. Thus antibodies or fragments thereof should be used which lack disulfide bridges while retaining native or modified epitope binding.

The number of repeats in the shaft portion should preferably be at least about 7, e.g. 6-12. The presence of a wild type knob (e.g. as one of two types of fibre proteins wherein the second is modified for re-targeting) may be beneficial for generation of recombinant viable Ad virons.

The invention claimed is:

1. A modified adenovirus comprising
one or more non-native polypeptides,
each polypeptide comprising one or more framework moieties which possess a folded three dimensional structure, each framework moiety containing one or more binding moieties, wherein each framework moiety is derived from an antibody or a bacterial receptor,
said polypeptide forming part of a recombinant adenoviral fiber protein and being capable of being expressed in a cytoplasm and a nucleus of a mammalian host cell,
wherein said polypeptide folds in a conformation which is maintained in the absence of a ligand for said binding moieties, said conformation allowing said binding moieties to bind with said ligand and wherein said conformation does not rely on di-sulphide bonding for its conformation when expressed in the mammalian host cell cytoplasm, and
said polypeptide being capable of transport through a nuclear membrane, wherein said modified adenovirus has an altered tropism conferred by said binding moieties.

2. The modified adenovirus of claim 1 which is derived from human adenovirus.

3. The modified adenovirus of claim 1 which is derived from human adenovirus serotype 5.

4. The modified adenovirus of claim 1 wherein said non-native polypeptide is soluble in a cellular environment.

5. The modified adenovirus of claim 1 wherein said non-native polypeptide is soluble in a cellular environment.

6. The modified adenovirus of claim 5 wherein greater than 30% of the non-native polypeptide is present in the soluble fraction of cell lysates of cells expressing the non-native polypeptide.

7. The modified adenovirus of claim 1 wherein a wild-type fiber knob or cell binding domain of said recombinant adenoviral fiber protein is removed.

8. The modified adenovirus of claim 1 wherein said non-native polypeptide comprises one or more further elements that mimic a native structure or function of a viral protein component in which said non-native polypeptide is incorporated or which said non-native polypeptide replaces.

9. The modified adenovirus of claim 1 wherein said non-native polypeptide does not contain any di-sulphide bonds.

10. The modified adenovirus of claim 1 wherein said non-native polypeptide comprises one or more α-helical structures.

11. The modified adenovirus of claim 1 wherein said framework moiety is derived from an antibody and comprises one or more binding moieties derived from a CDR of a further antibody.

12. The modified adenovirus of claim 1 wherein said non-native polypeptide comprises a combinatorial protein or an affibody.

13. The modified adenovirus of claim 1 wherein said non-native polypeptide comprises one or more binding moieties which are present within one or more loops of a helical bundle and/or one or more loops connecting said helical bundles.

14. The modified adenovirus of claim 1 wherein said non-native polypeptide comprises one or more framework moieties derived from the immunoglobulin binding Z-domain from staphylococcal protein A or an immunoglobulin binding domain from streptococcal protein G.

15. The modified virus of claim 1 wherein said non-native polypeptide further comprises a non native trimerisation motif.

16. The modified adenovirus of claim 1 wherein said non-native polypeptide further comprises a neck region peptide from a human lung surfactant protein D.

17. The modified adenovirus of claim 1 which comprises two or more different non-native polypeptides.

18. The modified adenovirus of claim 17 which comprises a first non-native polypeptide which binds a target cell and a second non-native polypeptide which binds a production cell or a permissive cell.

19. The modified adenovirus of claim 1 wherein said non-native polypeptide comprises a cleavage site positioned in a location that enables a binding moiety of said non-native polypeptide to be cleaved from said modified virus.

20. The modified adenovirus of claim 1 wherein said adenovirus comprises a modified viral component comprising said non-native polypeptide and a corresponding unmodified viral component.

21. The modified adenovirus of claim 1 wherein said non-native polypeptide comprises a binding moiety capable of binding to a cell specific ligand.

22. The modified adenovirus of claim 1 which further comprises a site for insertion of one or more desired therapeutic genes or nucleic acid molecules.

23. The modified adenovirus of claim 22 which comprises transgenes encoding cytosine deaminase and/or uracil phosphoribosyl transferase either as separate genes or together as a bifunctional fusion gene.

24. The modified adenovirus of claim 1 which further comprises a viral structural protein component which is replaced with an equivalent structural protein component from a different serotype or is modified such that binding of said modified virus by antibodies pre-formed to a wild type component is reduced.

25. The modified adenovirus of claim 24 wherein said viral component is a hexon protein.

26. An isolated cell containing said modified adenovirus of claim 1.

27. An isolated permissive cell comprising said modified adenovirus of claim 1, wherein the isolated permissive cell is capable of being cultured to propagate said modified virus.

28. A method for producing said modified adenovirus of claim 1 in a cell culture, comprising:
    infecting permissive cells with said modified adenovirus of claim 1;
    culturing said cells to produce said modified adenovirus; and
    harvesting, and optionally, purifying said produced modified adenovirus.

29. The modified adenovirus of claim 21, wherein said binding moiety capable of binding to a cell specific ligand is Prostate Specific Membrane Antigen, VEGF receptor, Her-2/Neu, VEGF receptor, CD22, gp120, MHC/peptide complexes or membrane structures or surface molecules expressed or present on proliferating cells, tumor cells or virus infected cells.

* * * * *